(12) United States Patent
Hoshino et al.

(10) Patent No.: US 8,389,249 B2
(45) Date of Patent: Mar. 5, 2013

(54) METHOD FOR PRODUCTION OF L-AMINO ACID

(75) Inventors: Yasushi Hoshino, Kawasaki (JP); Hidetaka Doi, Kawasaki (JP); Masaru Terashita, Kawasaki (JP); Yoshihiro Usuda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 190 days.

(21) Appl. No.: 12/951,187

(22) Filed: Nov. 22, 2010

(65) Prior Publication Data

US 2011/0117613 A1   May 19, 2011

Related U.S. Application Data

(63) Continuation of application No. PCT/JP2009/059408, filed on May 22, 2009.

(30) Foreign Application Priority Data

May 22, 2008 (JP) .................................. 2008-134519

(51) Int. Cl.
*C12P 13/04* (2006.01)
(52) U.S. Cl. ..................................................... 435/106
(58) Field of Classification Search .................... 435/106
See application file for complete search history.

(56) References Cited

U.S. PATENT DOCUMENTS

| | | | |
|---|---|---|---|
| 6,911,332 B2 | 6/2005 | Usuda et al. | |
| 7,026,149 B2 | 4/2006 | Usuda et al. | |
| 7,029,893 B2 | 4/2006 | Usuda et al. | |
| 7,060,475 B2 | 6/2006 | Usuda et al. | |
| 7,192,748 B2 | 3/2007 | Usuda et al. | |
| 7,220,570 B2 | 5/2007 | Usuda et al. | |
| 7,306,933 B2 | 12/2007 | Van Dien et al. | |
| 7,442,530 B2 * | 10/2008 | Rieping et al. | 435/115 |
| 7,468,262 B2 | 12/2008 | Usuda et al. | |
| 7,695,946 B2 | 4/2010 | Usuda et al. | |
| 7,696,315 B2 | 4/2010 | Usuda et al. | |
| 7,833,761 B2 | 11/2010 | Terashita et al. | |
| 2002/0160461 A1 | 10/2002 | Nakai et al. | |
| 2004/0132145 A1 | 7/2004 | Park et al. | |
| 2005/0233308 A1 | 10/2005 | Nishio et al. | |
| 2006/0257979 A1 | 11/2006 | Dusch | |
| 2009/0093029 A1 | 4/2009 | Usuda et al. | |
| 2009/0148915 A1 | 6/2009 | Van Dien et al. | |
| 2009/0203090 A1 | 8/2009 | Ptitsyn et al. | |
| 2009/0239269 A1 | 9/2009 | Tajima et al. | |
| 2009/0246835 A1 | 10/2009 | Iwatani et al. | |
| 2009/0291478 A1 | 11/2009 | Usuda et al. | |
| 2010/0047878 A1 | 2/2010 | Nagai et al. | |
| 2010/0062497 A1 | 3/2010 | Shiraga et al. | |
| 2010/0081180 A1 | 4/2010 | Fukui et al. | |
| 2010/0093044 A1 | 4/2010 | Terashita et al. | |
| 2010/0112647 A1 | 5/2010 | Hara et al. | |
| 2010/0190217 A1 | 7/2010 | Doi et al. | |
| 2010/0221792 A1 | 9/2010 | Nagai et al. | |

FOREIGN PATENT DOCUMENTS

| | | |
|---|---|---|
| JP | 57-068793 | 4/1982 |
| JP | 2002-017363 | 1/2002 |
| JP | 2004-129666 | 4/2004 |
| WO | WO2008/002053 | 1/2008 |

OTHER PUBLICATIONS

International Preliminary Report on Patentability for PCT Patent App. No. PCT/JP2009/059408 (Jan. 20, 2011).
Campbell, J. W., et al., "A new *Escherichia coli* metabolic competency: growth on fatty acids by a novel anaerobic β-oxidation pathway," Mol. Microbiol. 2003;47(3):793-805.
Shiio, I., et al., "Microbial Production of Amino Acids from Hydrocarbons. I. Preliminary Screening of Glutamic Acid Producing Bacteria," J. Gen. Appl. Microbiol. 1963;9(1):23-30.
International Search Report for PCT Patent App. No. PCT/JP2009/059408 (Jul. 21, 2009).

* cited by examiner

*Primary Examiner* — Tekchand Saidha
(74) *Attorney, Agent, or Firm* — Shelly Guest Cermak; Cermak Nakajima LLP

(57) ABSTRACT

An L-amino acid can be produced by culturing a bacterium which belongs to the Enterobacteriaceae family, and has an enhanced ability to use a fatty acid. The bacterium is capable of producing the L-amino acid in a culture medium containing a fatty acid or a hydrolysate of an oil-and-fat as a carbon source, thereby producing and accumulating the L-amino acid in a culture.

6 Claims, No Drawings

METHOD FOR PRODUCTION OF L-AMINO ACID

This application is a continuation under 35 U.S.C. §120 of PCT Patent Application No. PCT/JP2009/059408, filed May 22, 2009, which claims priority under 35 U.S.C. §119 to Japanese Patent Application No. 2008-134519, filed on May 22, 2008, which are incorporated in their entireties by reference. The Sequence Listing in electronic format filed herewith is also hereby incorporated by reference in its entirety (File Name: 2010-11-22T_US-451_Seq_List; File Size: 135 KB; Date Created: Nov. 22, 2010).

BACKGROUND OF THE INVENTION

1. Field of the Invention

The present invention relates to a method for producing an L-amino acid using a microorganism. L-amino acids are used in a variety of fields including, for example, seasonings, food additives, feed additives, chemical products, and pharmaceutical products.

2. Brief Description of the Related Art

L-amino acids, such as L-threonine and L-lysine, have been industrially produced by fermentation using L-amino acid-producing bacteria such as bacteria belonging to the genus of *Escherichia*. Examples of such L-amino acid-producing bacteria include bacterial strains isolated from nature, artificial mutant strains thereof, and genetic recombinant strains having enhanced activity of L-amino acid biosynthetic enzyme. Examples of a method for producing L-threonine include the methods described in Japanese Laid-Open Patent Application No. 5-304969, WO98/04715, Japanese Laid-Open Patent Application No. 5-227977, and US2002-0110876. Examples of a method for producing L-lysine include the methods described in Japanese Laid-Open Patent Application No. 10-165180, Japanese Laid-Open Patent Application No. 11-192088, Japanese Laid-Open Patent Application No. 2000-253879, and Japanese Laid-Open Patent Application No. 2004-129666. Examples of carbon sources used in the fermentation production of L-amino acids include saccharides, such as, glucose, fructose, sucrose, blackstrap molasses, and starch hydrolysates.

Clark, D. P. and Cronan (J. E. Jr. 1996. p. 343-357. In F. D. Neidhardt (ed.), *Escherichia coli* and *Salmonella* Cellular and Molecular Biology/Second Edition, American Society for Microbiology Press, Washington, D.C.) explain that wild type *Escherichia coli* is able to grow using a long-chain fatty acid having a carbon chain with 12 or more carbon atoms as the sole carbon source. Weeks, G. et al. (1969. Control of Fatty Acid Metabolism I. Induction of the Enzymes of Fatty Acid Oxidation in *Escherichia coli*. J. Bacteriol. 97: 827-836) explain that wild type *Escherichia coli* is able to grow in a medium using myristic acid, palmitic acid or oleic acid as a sole carbon source. Additionally, Clark, D. P. and Cronan, J. E. Jr. (1996. p. 343-357. In F. D. Neidhardt (ed.), *Escherichia coli* and *Salmonella* Cellular and Molecular Biology/Second Edition, American Society for Microbiology Press, Washington, D.C.) and Campbell J. W. et al. (2003. A new *Escherichia coli* metabolic competency: growth on fatty acids by a novel anaerobic beta-oxidation pathway. Mol. Microbiol. 47: 793-805) describe that fatty acids are utilized by enzymes encoded by a group of genes including fadL, fadD, fadE, fadB, fadA, fadJ and fadI, via a pathway called beta oxidation, and that such a group of fad genes is subject to repression by a transcription factor encoded by fadR. Furthermore, as shown in Cronan, J. E. Jr. and Subrahmanyam, S. (1998. FadR, transcriptional co-ordination of metabolic expediency. Mol. Microbiol. 29: 937-943), there are some reports about a strain lacking the fadR gene. However, as shown in Vorum, H. et al. (1992. Solubility of long-chain fatty acids in phosphate buffer at pH 7.4. Biochimica et Biophysica Acta, Lipids and Lipid Metabolism 1126: 135-142), the solubility of a fatty acid is, in general, extremely low and so far, there are no examples of production of a substance by a direct fermentation method using a fatty acid as the major carbon source. Thus, in order to use the fatty acid as the carbon source for production of L-amino acids, it is very important that the fatty acid in a medium is physiologically treated so that it is more usable and so that fatty acid utilization by a fermentative bacterium is enhanced. Thus far, there have been no reports that explain the effects of deletion or amplification of genes involved in fatty acid utilization or substance production using fatty acids as carbon sources.

Japanese Laid-Open Patent Application No. 2004-129666 discloses a method for producing L-threonine using a microorganism lacking the fadR gene on its chromosome. Additionally, Japanese Laid-Open Patent Application No. 2002-017363 discloses a method for producing a substance by enhancing a respiratory chain pathway with high-energy acquiring efficiency or deleting a respiratory chain pathway with low-energy acquiring efficiency. However, in both cases the carbon source was glucose. Neither study described any significant effects in cases where fatty acids were used as carbon sources.

SUMMARY OF THE INVENTION

Aspects of the present invention include an efficient and inexpensive method for producing an L-amino acid by using fatty acids or a novel raw material such as an hydrolysate of an oil-and-fat, and using a microorganism with enhanced ability to use such raw materials, instead of a conventional method of fermentative production of L-amino acids using saccharides as the major carbon sources.

These aspects were achieved by finding that L-amino acids are efficiently produced when an L-amino acid producing bacterium, belonging to the Enterobacteriaceae family, with enhanced ability to use fatty acids, is cultured in a medium with fatty acids as a carbon source. Previously, the use of such fatty acids as a fermentation raw material was not considered ideal because it resulted in a slow growth rate of a bacterium.

Accordingly, it is an aspect of the present invention to provide a method for producing an L-amino acid comprising: A) culturing a bacterium belonging to the Enterobacteriaceae family in a medium comprising a fatty acid or a hydrolysate of an oil-and-fat, to produce and accumulate an L-amino acid in the medium or bacterial cells, and B) collecting the L-amino acid from the medium or from the bacterium, wherein said bacterium has an enhanced ability to use a fatty acid, and has an L-amino acid-producing ability.

It is a further aspect of the present invention to provide the method as described above, wherein said ability to use a fatty acid is enhanced by modifying one or more genes involved in the utilization of a fatty acid.

It is a further aspect of the present invention to provide the method as described above, wherein said ability to use a fatty acid is enhanced by attenuating expression of a fadR gene or making the gene deficient.

It is a further aspect of the present invention to provide the method as described above, wherein said ability to use a fatty acid is enhanced by increasing expression of a gene selected from the group consisting of fadI, fadJ, fadL, fadE, fadD, fadB fadA, combinations thereof.

It is a further aspect of the present invention to provide the method as described above, wherein said combination is fadB and fadA.

It is a further aspect of the present invention to provide the method as described above, wherein said combination is the fadI and fadJ.

It is a further aspect of the present invention to provide the method as described above, wherein said ability to use a fatty acid is enhanced by increasing expression of cyoABCDE operon.

It is a further aspect of the present invention to provide the method as described above, wherein said bacterium belongs to the genus of *Escherichia*.

It is a further aspect of the present invention to provide the method as described above, wherein said bacterium is *Escherichia coli*.

It is a further aspect of the present invention to provide the method as described above, wherein said L-amino acid is selected from the group consisting of L-threonine, L-lysine L-tryptophan, and combinations thereof.

According to the present invention, L-amino acids can be produced with high efficiency by using a novel carbon source.

DESCRIPTION OF THE PREFERRED EMBODIMENTS

<1> L-Amino Acid Production Method

According to the presently disclosed subject matter, a method for producing an L-amino acid can include culturing a bacterium belonging to the Enterobacteriaceae family in a medium containing a fatty acid or a hydrolysate of an oil-and-fat to produce and accumulate the L-amino acid in the medium or in the bacterial cells, and collecting the L-amino acid from the medium or from the bacterial cells, wherein the bacterium has an enhanced ability to use a fatty acid and has an L-amino acid-producing ability. Many different types of cultures can be used including, but not limited to, a batch culture, fed-batch culture and continuous culture. Fatty acids or an hydrolysate of an oil-and-fat in the medium can be present in the initial medium, in the feeding medium, or in both.

The fed-batch culture can refer to a culturing method wherein a medium is continuously or intermittently fed into a culture vessel and the medium is not taken out of the vessel until the end of the culturing. Continuous culture can refer to a method wherein a medium is continuously or intermittently fed into a culture vessel and the medium—the amount of which is usually equal to the amount of the medium being fed—is taken out of the vessel. An initial medium can mean a medium, at the time of the starting of the culture, used in the batch culture before adding a feeding medium in the fed-batch culture or continuous culture. A feeding medium can mean a medium to be fed into a fermenter when the fed-batch culture or continuous culture is carried out. The batch culture can refer to a method wherein a fresh medium is provided every time, a bacterial strain is seeded therein, and the medium is not added until collection.

A fatty acid can refer to a monovalent carboxylic acid of long chain hydrocarbon represented by the general formula $C_{13}H_{27}COOH$, where n+1 and m+1 represent the number of carbon atoms and the number of hydrogen atoms, respectively. Generally, it is often the case that a fatty acid with 12 or more carbon atoms is referred to as a long-chain fatty acid. There are a variety of fatty acids with varying numbers of carbons and varying degrees of unsaturation. Fatty acids constitute an oil-and-fat, and different types of an oil-and-fat have different compositions of fatty acids. Myristic acid ($C_{13}H_{27}COOH$) is a saturated fatty acid having 14 carbon atoms and is contained in coconut oil and palm oil. Palmitic acid ($C_{15}H_{31}COOH$) is a saturated fatty acid having 16 carbon atoms and is abundantly present in general vegetable oil-and-fat. Stearic acid ($C_{17}H_{35}COOH$) is a saturated fatty acid having 18 carbon atoms and is abundantly present in animal fats and plant oils. Oleic acid ($C_{17}H_{33}COOH$) is a monovalent unsaturated fatty acid having 18 carbon atoms and is abundantly present in animal fats or vegetable oils. Linoleic acid ($C_{17}H_{31}COOH$) is a multivalent unsaturated fatty acid having 18 carbon atoms and two cis-type double bonds at the $9^{th}$ and $12^{th}$ positions. A mixture of the long-chain fatty acids can be used as fatty acids. When the mixture of the fatty acids is used as a carbon source, any mixing ratio of the fatty acids can be employed as long as it is a concentration ratio at which a bacterium can use it as the carbon source. A mixture of fatty acids obtained by removing glycerol from a hydrolysate of an oil-and-fat can also be used. A hydrolysate of an oil-and-fat can also be used.

An oil-and-fat can mean esters composed of fatty acids and glycerols, and can also be referred to as triglycerides. An oil-and-fat can include fatty oils (oils) which are liquid at normal temperature, and fats which are solid at normal temperature, and any other oil-and-fat, as long as they can be subjected to a hydrolysis reaction. Also, all oil-and-fats derived from plants and animals, including fish can be used. These can be used as one alone and in combinations of two or more. An oil-and-fat used as a raw material can be a pure oil-and-fat or a mixture containing substances other than an oil-and-fat. For example, an oil-and-fat derived from a plant can include a plant extract containing an oil-and-fat or a fraction thereof.

Examples of animal oil-and-fats include, but are not limited to, butter, lard, beef tallow, mutton suet or the like, whale oil, sardine oil, and herring oil and the like. Examples of vegetable oil-and-fats include, but are not limited to, palm oil, olive oil, canola oil, soybean oil, rice bran oil, walnut oil, sesame oil, and peanut oil. Palm oil can be obtained from the fruit of oil palms. It has increasingly been used as biodiesel fuel, and therefore, the amount of production thereof has increased. Oil palms can refer to a collective term classified into the genus of *Elaeis* within the family of Arecaceae. Crude palm oil can refer to an unrefined palm oil commonly produced in an oil mill and can be traded as crude palm oil. Also, some microalgae are known to accumulate an oil-and-fat (Chisti, Y. 2007. Biotechnol Adv. 25: 294-306), and therefore, it is possible to extract the oil-and-fat from an alga body. In addition to an oil-and-fat, other organic substances such as saccharides, proteins and amino acids are contained in the alga body, and a mixture containing these can be hydrolyzed and used as carbon sources.

The oil-and-fats are fatty acid species that can be used as carbon sources by bacteria, are generated by hydrolysis, and have higher contents of such fatty acids. Examples of long-chain fatty acid species, which bacteria having an L-amino acid-producing ability can use, include, but are not limited to, lauric acid, myristic acid, palmitic acid, stearic acid, and oleic acid.

A hydrolysate of an oil-and-fat can refer to one obtained by hydrolyzing the above-described oil-and-fat chemically, or by an enzyme, and can refer to a mixture of fatty acids and glycerols. A method of continuous high temperature hydrolysis, wherein an oil-and-fat is brought into contact with water at high temperatures (250 to 260° C.) and under high pressures (5-6 MPa), is commonly carried out as an industrial method of hydrolysis. Also, a reaction at low temperature (about 30° C.) using an enzyme can be carried out as an industrial method of hydrolysis as well (Jaeger, K. E. et al. 1994. FEMS Microbiol. Rev. 15: 29-63). An example of the above-described enzyme that can be used is a lipase, which catalyzes a hydrolysis reaction of an oil-and-fat. The lipase is an important enzyme industrially and is employed in a variety of industrial applications (Hasan, F. et al. 2006. Enzyme and Microbiol. Technol. 39: 235-251). A hydrolysate of an oil-and-fat can refer to a mixture of fatty acids and glycerols, where a ratio by weight of the glycerol to the fatty acids present in a hydrolysate of a common oil-and-fat, such as palm oil, is about 10%. The hydrolysate of an oil-and-fat is not particularly limited as long as it contains the fatty acids. For instance, the hydrolysate of an oil-and-fat can be used as it is, with part of the fatty acids or glycerols being removed, and with fatty acids or glycerols being added. The ratio by weight of the glycerols to the fatty acids at that time is, for example, 5 to 20:100, and 7.5 to 15:100.

Any amount of a fatty acid or hydrolysate of an oil-and-fat present in a medium can be employed as long as a bacterium can use it as a carbon source. When the fatty acid or hydrolysate of an oil-and-fat is added in a medium as a single carbon source, it can be present, for example, at the concentration of not more than 10 w/v %, not more than 5 w/v %, or not more than 2 w/v %. Also, when it is added in the medium as the sole carbon source, it can be present, for example, at a concentration of not less than 0.2 w/v %, not more than 0.5 w/v %, or not more than 1.0 w/v %.

Also, when it used as a feeding medium, in cases where the fatty acid or hydrolysate of an oil-and-fat is added in the feeding medium as the sole carbon source, it can be present, for example, at a concentration in the medium after the feeding of not more than 5 w/v %, not more than 2 w/v %, or not more than 1 w/v %. Also, in cases where it is added in the medium as the sole carbon source, it can be controlled, for example, at a concentration of not less than 0.01 w/v %, not more than 0.02 w/v %, or not more than 0.05 w/v %.

The concentration of the fatty acid can be measured by gas chromatography (Hashimoto, K. et al. 1996. Biosci. Biotechnol. Biochem. 70:22-30) or HPLC (Lin, J. T. et al. 1998. J. Chromatogr. A. 808: 43-49).

The fatty acid, whether it is added to a medium or present in a hydrolysate of an oil-and-fat, can be used as an alkali metal salt with sodium, potassium, or the like, which is micellized in water. However, there are some instances where even the solubility of a sodium salt or potassium salt of fatty acid is not sufficient for a use of a fermentation raw material. Thus, in order for a bacterium having an L-amino acid-producing ability to more efficiently use the fatty acid as a carbon source, a step to promote homogenization, such as a step of carrying out emulsification, can be included. For example, an emulsifying agent or detergent can be added for emulsification. Examples of the emulsifying agent include, but are not limited to, phospholipids and sterols. Examples of nonionic detergents include, but are not limited to, polyoxyethylene sorbitan fatty acid esters, such as poly(oxyethylene)sorbitan monooleic acid ester (Tween 80); alkylglucosides, such as n-octyl-β-D-glucoside; sucrose fatty acid esters, such as sucrose stearic acid ester; and polyglycerol fatty acid esters, such as polyglycerol stearic acid ester. An example of zwitter ion detergents includes, but is not limited to, N,N-dimethyl-N-dodecyl glycine betaine, which is an alkyl betaine. Apart from the above, detergents commonly used in the field of biology such as Triton X-100, polyoxyethylene(20)cetyl ether (Brij-58), and nonyl phenol ethoxylate (Tergitol NP-40) can be used.

Furthermore, a procedure to promote emulsification and homogenization of a fatty acid is also effective. In fact, any procedure can be employed as long as it is a procedure to promote emulsification and homogenization of fatty acids. Specific examples include, but are not limited to, homogenizer treatments, homomixer treatments, sonication, high-pressure treatments and high temperature treatments. Homogenizer treatments, sonication, and a combination thereof can also be used.

The detergent treatment and homogenizer treatment, as well as sonication can be combined. These treatments can be carried out under alkaline conditions where fatty acids are more stable. The alkaline condition can be, for example, not less than pH 9, or not less than pH 10.

Furthermore, other carbon sources, in addition to a fatty acid or hydrolysate of an oil-and-fat, can be added to a medium. Examples of other carbon sources include, but are not limited to, saccharides, such as glucose, fructose, sucrose, lactose, galactose, blackstrap molasses, starch hydrolysate, and a saccharide solution obtained by hydrolysis of biomass; alcohols, such as ethanol; and organic acids, such as fumaric acid, citric acid and succinic acid. When other carbon sources are used, the ratio of fatty acids or hydrolysates of an oil-and-fat in the total carbon sources can be, for example, not less than 10% by weight, not less than 30% by weight, or not less than 50% by weight.

A fatty acid or hydrolysate of an oil-and-fat can be present at a constant concentration throughout all steps of culture; or can be added only in a feeding medium or initial medium. As long as other carbon sources are sufficiently present, a certain period of time when the fatty acid or hydrolysate of an oil-and-fat can exist. The term "a certain period of time" can mean, for example, 10%, 20%, or up to 30% of the entire period of fermentation during which the fatty acid or hydrolysate of an oil-and-fat is short. An example of where the concentration of the fatty acid is temporarily 0 can be included in the phrase "culturing in a medium containing a fatty acid and hydrolysate of an oil-and-fat," as long as a period of culturing in the medium containing the fatty acid and hydrolysate of an oil-and-fat exists.

Examples of ingredients that can be used, other than carbon sources to be added to a medium include, but are not limited to, nitrogen sources, inorganic ions and, as required, other organic ingredients. Examples of nitrogen sources to be contained in the medium include, but are not limited to, ammonia and ammonium salts or nitrate salts, such as ammonium sulfate, ammonium carbonate, ammonium chloride, ammonium phosphate, ammonium acetate or urea. Ammonia gas or aqueous ammonia, which is used to adjust pH, can also be used as the nitrogen sources. Additionally, peptone, yeast extracts, meat extracts, malt extracts, corn steep liquor, soybean hydrolysates, or the like can be used. In the medium, one of these nitrogen sources can be contained alone, or two or more of them can be contained. These nitrogen sources can be used in both an initial medium and a feeding medium. In addition, the same nitrogen sources can be used in both the initial medium and feeding medium. Alternatively, the nitrogen sources in the feeding medium can be different from the nitrogen sources of the initial medium.

Phosphate sources and sulfur sources, in addition to carbon sources and nitrogen sources, can be present in the medium. Examples of the phosphate sources that can be used include, but are not limited to, potassium dihydrogen phosphate, dipotassium hydrogen phosphate, and phosphate polymer such as pyrophosphoric acid. Also, any source can be used as the sulfur source, as long as it contains a sulfur atom. For example, sulfate salts such as sulfate salts, thiosulfate salts and sulfite salts; and sulfur-containing amino acids such as cysteine, cystine or glutathione. Among them, ammonium sulfate is another example.

In addition, besides the above-described ingredients, growth-promoting factors (nutrients having a growth promoting effect) can be present in the medium. Examples of the growth promoting factors that can be used include, but are not limited to, trace metals, amino acids, vitamins, nucleic acids; as well as peptone, casamino acid, yeast extracts, and soy bean protein hydrolysates, which contain trace metals, amino acids, vitamins, or nucleic acids. Examples of the trace metals include, but are not limited to, ferrum, manganese, magnesium, and calcium. Examples of the vitamins include, but are not limited to, vitamin B1, vitamin B2, vitamin B6, nicotinic acid, nicotinic acid amide, and vitamin B12. These growth promoting factors can be present in an initial medium and in a feeding medium.

Moreover, when an auxotrophic mutant strain is used, which requires an amino acid for growth, a required nutrient can be supplemented to a medium. Since, as described later, it is often the case where, in an L-lysine-producing bacterium, an L-lysine biosynthetic pathway is enhanced and the ability to decompose L-lysine is weakened, one or more of L-threonine, L-homoserine, L-isoleucine and L-methionine can be added. An initial medium and feeding medium can have the same medium composition or a different medium composition. In addition, the initial medium and feeding medium can have the same sulfur concentration or a different sulfur concentration. Furthermore, when feeding of the feeding medium is carried out in multiple steps, each of the feeding mediums can have the same composition or a different one.

An aerobic culture can be carried out at a fermentation temperature of 20 to 45° C., or in particular, at 33 to 42° C. The culture is carried out by adjusting the concentration of oxygen to 5 to 50%, or at about 10%. Also, the aerobic culture can be carried out by controlling the pH at 5 to 9. When the pH decreases during the culture, neutralization can be performed, for example, by adding calcium carbonate or with alkali from ammonia gas, aqueous ammonia or the like. Under such conditions, by culturing for about 10 hours to 120 hours, a significant amount of an L-amino acid is accumulated in the culture solution. As long as it is a concentration at which collection and recovery from the culture medium is feasible, the accumulated L-amino acid can be any concentration, and the concentration can be for example, not less than 50 g/L, not less than 75 g/L, or not less than 100 g/L.

Collection of an L-amino acid from a culture solution after completion of the culture can be carried out in accordance with a known collection method. For instance, the collection can be carried out by removing bacterial cells from the culture solution by centrifugation, and by subsequent concentration crystallization.

In order to keep the accumulation of L-amino acid equal to or more than a certain constant amount, the culture of a bacterium can be carried out by separating the seed culture from the main culture. The seed culture can be carried out by culture under shaking using a flask or the like or batch culture, and the main culture is carried out by fed-batch culture or continuous culture. Both the seed culture and main culture can be carried out by the batch culture.

When a fed-batch culture or continuous culture is carried out, a feeding medium can be intermittently fed such that feeding of fatty acids or other carbon sources temporarily stops. Also, supplying the feeding medium can be, for example, stopped up to 30%, not more than 20%, and not more than 10% of time during which the feeding is carried out. When a fed-batch culture solution is intermittently fed, the feeding medium can be added over a certain period of time; the second and subsequent additions can be controlled so as to begin when an increase in pH or increase in dissolved oxygen concentration occurs. Such an increase occurs when carbon sources in the fermentation medium are becoming depleted when addition is terminated, proceeding a certain stage of addition, can be detected by a computer. The substrate concentration in the fermenter always can be automatically kept at low level (U.S. Pat. No. 5,912,113).

The feeding medium to be used for fed-batch culture can contain fatty acids, hydrolysates of an oil-and-fat and other carbon sources, as well as nutrients having growth-promoting effects (growth promoting factors). The concentration of the fatty acids in the fermentation medium can be controlled so as to be equal to or less than a certain level.

Examples of other carbon sources added to the feeding medium include, but are not limited to, glucose, sucrose and fructose. Examples of the growth promoting factors include, but are not limited to, nitrogen sources, phosphoric acid, and amino acids. Examples of the nitrogen sources include, but are not limited to, ammonia; ammonium salts such as ammonium sulfate, ammonium carbonate, ammonium chloride, ammonium phosphate, ammonium acetate or urea; and nitrate salts. Also, as phosphate sources, potassium dihydrogen phosphate and dipotassium hydrogen phosphate can be used. When an auxotrophic mutant strain is used as the amino acid the required nutrients can be supplemented. The feeding medium can be one kind, or a combination of two or more kinds of media. When two or more of the feeding media are used, those media can be combined and fed from one feed vessel or they can be fed from plural feeding vessels.

When continuous culture is used, removal can be carried out at the same time as feeding, or a partial removal can be carried out before the feeding. Also, it can be a continuous culture wherein L-amino acids and cells are not removed from the culture solution, and bacterial cells are recycled by returning the cells to the fermenter (see France Patent No. 2669935). A method wherein nutrient sources are continuously or intermittently fed can employ the same method as a fed-batch culture.

Continuous culture, wherein bacterial cells are recycled, is a method wherein a fermentation medium is intermittently or continuously removed when a predetermined amino acid concentration is attained, the L-amino acid alone is collected, a filtration residue containing bacterial cells is recirculated to the fermenter, and, for example, carried out in reference to French Patent No. 2669935.

When a fermentation medium is intermittently removed, a predetermined L-amino acid concentration is attained, part of L-amino acids can be removed, and a fresh medium can be fed to carry out culture. Also, the amount of medium to be added can be set so as to be finally equal to the amount of culture solution before the removal. The equal amount herein can mean an amount of 93 to 107% of the amount of culture solution before the removal.

When a fermentation medium is continuously removed, the removal can be started at the same time as feeding of a nutrient medium or after the feeding. For instance, a starting time for the drawing is within 5 hours from the beginning of the feeding, within 3 hours, or within 1 hour. Also, the amount of culture solution to be removed can be equal to the amount to be fed.

<2> Bacterium

A bacterium belonging to the Enterobacteriaceae family, having an enhanced ability to use a fatty acid, and having an L-amino acid-producing ability can be used. Bacteria belonging to the Enterobacteriaceae family include, but are not limited to, bacteria belonging to the genera *Escherichia, Enterobacter, Erwinia, Klebsiella, Pantoea, Photorhabdus, Providencia, Salmonella, Serratia, Shigella, Morganella, Yersinia*. In particular, bacteria classified into the Enterobacteriaceae family based on a classification method used in the database (http://www.ncbi.nlm.nih.gov/Taxonomy/Browser/wwwtax.cgi?id=91347) of NCBI (National Center for Biotechnology Information) can be used.

A bacterium belonging to the genus of *Escherichia* is not particularly limited and can mean that the bacterium is classified into the genus of *Escherichia* by classification known to those skilled in the art of microbiology. An example of the bacterium belonging to the genus of *Escherichia* includes *Escherichia coli* (*E. coli*) but is not limited thereto.

Bacteria belonging to the genus of *Escherichia* are not particularly limited, and include, for example, strains described in Table 1 of Bachmann et al. (Bachmann, B. J. 1996. p. 2460-2488. In F. D. Neidhardt (ed.), *Escherichia coli* and *Salmonella* Cellular and Molecular Biology/Second Edition, American Society for Microbiology Press, Washington, D.C.). Specific examples thereof include *Escherichia coli* W3110 (ATCC 27325) strain derived from a prototype of wild type K12 strain, *Escherichia coli* MG1655 (ATCC 47076) strain and the like.

These bacterial strains can be provided, for example, from American Type Culture Collection (address: P.O. Box 1549, Manassas, Va. 20108, 1, United States of America). That is, each bacterial strain is given an accession number, and can be ordered according to this accession number. The accession number corresponding to each bacterial strain is described in the catalog of American Type Culture Collection.

A bacterium belonging to the genus of *Pantoea* can mean that the bacterium is classified into the genus of *Pantoea* based on classification known to those skilled in the art of microbiology. Examples of representative strains of the genus of *Pantoea* bacteria include, but are not limited to, *Pantoea ananatis, Pantoea stewartii, Pantoea agglomerans*, and *Pantoea citrea*. Certain kinds of *Enterobacter agglomerans* are recently reclassified into *Pantoea agglomerans, Pantoea ananatis, Pantoea stewartii* or others based on analysis of the nucleotide sequence of 16S rRNA (Int. J. Syst. Bacteriol. 1993. 43: 162-173). Bacteria belonging to the genus of *Pantoea* include bacteria, which have been reclassified into the genus of *Pantoea* as described above.

Examples of bacteria belonging to the genus of *Enterobacter* include, but are not limited to, *Enterobacter agglomerans, Enterobacter aerogenes*. Examples of bacteria belonging to the genus of *Erwinia* include, but are not limited to, *Erwinia amylovora, Erwinia carotovora*. An example of bacteria belonging to the genus of *Klebsiella* includes *Klebsiella planticola*.

The phrase "having an enhanced ability to use a fatty acid" can mean the contribution of a fatty acid as a source for supplying carbon. This carbon can constitute a bacterial cell component or L-amino acid in bacterial growth and L-amino acid production can be substantially increased. For instance, when a bacterium cultured in a medium containing a fatty acid exhibits better growth as compared to an unmodified strain, or a higher yield of L-amino acids as compared to the unmodified strain, the ability to use a fatty acid is evaluated as enhanced.

"Enhancing the ability to use a fatty acid" is achieved, for example, by modifying genes involved in fatty acid utilization or the cyoABCDE genes.

"Genes involved in fatty acid utilization" can mean the fadR gene, and a group of genes under the control of fadR (hereinafter, referred to as the fad gene group), and specifically includes fadR, as well as fadA, fadB, fadI, fadJ, fadL, fadE, fadD.

<2-1> Imparting an L-Amino Acid-Producing Ability

A bacterium having an L-amino acid-producing ability can refer to a bacterium which is able to produce and secrete L-amino acid in a medium when cultured in a medium containing a fatty acid or hydrolysate of an oil-and-fat. In addition, it can refer to a bacterium capable of accumulating an L-amino acid of interest not less than 0.5 g/L, or not less than 1.0 g/L. L-amino acids include, but are not limited to, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. L-threonine, L-lysine, L-phenylalanine, L-tryptophan, L-valine, L-leucine, L-isoleucine and L-methionine are particular examples, and L-threonine and L-lysine other particular examples.

As long as a bacterium is capable of using a fatty acid or hydrolysate of an oil-and-fat to produce the L-amino acid by enhancing the ability to use the fatty acid, any L-amino acid-producing bacterium, which has thus far been reported, can be used. Each L-amino acid-producing bacterium that can be used will now be described below.

L-Threonine-Producing Bacteria

Examples of microorganisms having L-threonine-producing ability include bacteria in which one or more activities of L-threonine biosynthesis system enzymes are enhanced. Examples of L-threonine biosynthetic enzymes include aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). The parentheses after the names of the enzymes are the names of the genes coding for the respective enzymes (the same applies throughout this specification). Among these enzymes, aspartate semialdehyde dehydrogenase, aspartokinase I, homoserine kinase, aspartate aminotransferase, and, threonine synthase are particularly preferred. The genes coding for the L-threonine biosynthetic enzymes can be introduced into an *Escherichia* bacterium, which has a reduced ability to decompose threonine. An example of such an *Escherichia* bacterium is the TDH6 strain, which is deficient in threonine dehydrogenase activity (JP 2001-346578 A).

The enzymatic activities of the L-threonine biosynthetic enzymes are inhibited by the end product, L-threonine. Therefore, the genes for the L-threonine biosynthetic enzymes can be modified so that the enzymes are desensitized to feedback inhibition by L-threonine in the L-threonine-producing strains. The above-described thrA, thrB, and thrC genes constitute the threonine operon, which attenuates function. The expression of the threonine operon is inhibited by isoleucine and threonine in the culture medium and also suppressed by this attenuation. Therefore, the threonine operon can be modified by removing the leader sequence or the sequence responsible for attenuation in the attenuation region (refer to Lynn, S. P., Burton, W. S., Donohue, T. J., Gould, R. M., Gumport, R. L, and Gardner, J. F., J. Mol. Biol. 194:59-69 (1987); WO02/26993; WO2005/049808).

The native promoter of the threonine operon is present upstream of the threonine operon, and can be replaced with a non-native promoter (refer to WO98/04715), or a threonine operon which has been modified so that expression of the threonine biosynthesis gene is controlled by the repressor and promoter of λ-phage (EP 0593792). Furthermore, in order to modify a bacterium so that it is desensitized to feedback inhibition by L-threonine, a strain resistant to α-amino-β-hydroxyisovaleric acid (AHV) can be selected.

The copy number of the threonine operon that is modified as described above can be increased so that it is desensitized to feedback inhibition by L-threonine in the host bacterium, or increase expression of such a modified operon by ligating it to a potent promoter. Besides amplification using a plasmid, the copy number can also be increased by transferring the threonine operon to a genome using a transposon, Mu-phage, or the like.

Other than increasing expression of the L-threonine biosynthetic genes, expression of the genes involved in the glycolytic pathway, TCA cycle, or respiratory chain, the genes that regulate the expression of these genes, or the genes involved in sugar uptake can also be increased. Examples of these genes include the genes encoding transhydrogenase (pntAB, EP 733712 B), phosphoenolpyruvate carboxylase (pepC, WO95/06114), phosphoenolpyruvate synthase (pps, EP 877090 B), and pyruvate carboxylase, all of which can be derived from coryneform bacterium or *Bacillus* bacterium (WO99/18228, EP 1092776 A).

Expression of a gene that imparts L-threonine resistance, a gene that imparts L-homoserine resistance, and/or both to the host can be enhanced. Examples of these genes include rhtA (Res. Microbiol., 154:123-135 (2003)), rhtB (EP 0994190 A), rhtC (EP 1013765 A), yfiK, and yeaS (EP 1016710 A). The methods for imparting L-threonine resistance to a host are described in EP 0994190 A and WO90/04636.

Examples of parent strains which can be used to derive the L-threonine-producing bacteria include, but are not limited to, strains belonging to the genus *Escherichia*, such as *E. coli* TDH-6/pVIC40 (VKPM B-3996) (U.S. Pat. No. 5,175,107, U.S. Pat. No. 5,705,371), *E. coli* 472T23/pYN7 (ATCC 98081) (U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), and *E. coli* VL643 and VL2055 (EP 1149911 A), and the like.

The TDH-6 strain is deficient in the thrC gene, as well as being sucrose-assimilative, and the ilvA gene has a leaky mutation. This strain also has a mutation in the rhtA gene, which imparts resistance to high concentrations of threonine or homoserine. The B-3996 strain contains pVIC40, which was obtained by inserting the thrA*BC operon which includes a mutant thrA gene into a RSF1010-derived vector. This mutant thrA gene encodes aspartokinase homoserine dehydrogenase I which is substantially desensitized to feedback inhibition by threonine. The B-3996 strain was deposited on Nov. 19, 1987 in the All-Union Scientific Center of Antibiotics (Nagatinskaya Street 3-A, 117105 Moscow, Russian Federation) under the accession number RIA 1867. This strain was also deposited in the Russian National Collection of Industrial Microorganisms (VKPM) (Russia, 117545 Moscow 1, Dorozhny proezd. 1) on Apr. 7, 1987 under the accession number B-3996.

*E. coli* VKPM B-5318 (EP 0593792B) can also be used to derive the L-threonine-producing bacteria. The B-5318 strain is prototrophic with regard to isoleucine, and a temperature-sensitive lambda-phage C1 repressor and PR promoter replaces the regulatory region of the threonine operon in plasmid pVIC40. The VKPM B-5318 strain was deposited in the Russian National Collection of Industrial Microorganisms (VKPM) on May 3, 1990 under accession number of VKPM B-5318.

The sequence of the thrA gene of *Escherichia coli*, which encodes aspartokinase homoserine dehydrogenase I, has been identified (nucleotide positions 337 to 2799, GenBank accession NC_000913.2, gi: 49175990). The thrA gene is located between the thrL and thrB genes on the chromosome of *E. coli* K-12. The nucleotide sequence of the thrB gene of *Escherichia coli*, which encodes homoserine kinase, has been elucidated (nucleotide positions 2801 to 3733, GenBank accession NC_000913.2, gi: 49175990). The thrB gene is located between the thrA and thrC genes on the chromosome of *E. coli* K-12. The nucleotide sequence of the thrC gene of *Escherichia coli*, which encodes threonine synthase, has been elucidated (nucleotide positions 3734 to 5020, GenBank accession NC_000913.2, gi: 49175990). The thrC gene is located between the thrB gene and the yaaX open reading frame on the chromosome of *E. coli* K-12. All three genes function together as a single threonine operon. To enhance the expression of the threonine operon, the attenuator region, which affects the transcription, can be removed from the operon (WO2005/049808, WO2003/097839).

The mutated thrA gene which encodes feedback-resistant aspartokinase homoserine dehydrogenase I, as well as the thrB and thrC genes, can be obtained as one operon from the well-known plasmid pVIC40. This plasmid is present in the threonine producing *E. coli* strain VKPM B-3996, and is described in detail in U.S. Pat. No. 5,705,371.

The rhtA gene is at 18 min on the *E. coli* chromosome close to the glnHPQ operon, which encodes components of the glutamine transport system. The rhtA gene is identical to ORF1 (ybiF gene, nucleotide positions 764 to 1651, GenBank accession number AAA218541, gi:440181), and is located between the pexB and ompX genes. The sequence expressing a protein encoded by the ORF1 has been designated the rhtA gene (rht: resistance to homoserine and threonine). Also, the rhtA23 mutation is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457, EP 1013765 A).

The nucleotide sequence of the asd gene of *E. coli* has already been elucidated (nucleotide positions 3572511 to 3571408, GenBank accession NC_000913.1, gi:16131307), and can be obtained by PCR (polymerase chain reaction; refer to White, T. J. et al., Trends Genet., 5, 185 (1989)) by utilizing primers based on the nucleotide sequence of the gene. The asd genes from other microorganisms can be obtained in a similar manner.

Also, the nucleotide sequence of the aspC gene of *E. coli* has already been elucidated (nucleotide positions 983742 to 984932, GenBank accession NC_000913.1, gi:16128895), and can be obtained by PCR. The aspC genes from other microorganisms can be obtained in a similar manner.

L-Lysine-Producing Bacteria

Examples of L-lysine-producing bacteria belonging to the genus *Escherichia* can include mutants having resistance to an L-lysine analogue. The L-lysine analogue inhibits growth of bacteria belonging to the genus *Escherichia*, but this inhibition is fully or partially desensitized when L-lysine is present in a medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 can be used as an L-lysine producing bacterium of *Escherichia coli*. This bacterial strain was bred by conferring AEC resistance to the strain W3110, which was derived from *Escherichia coli* K-12. The resulting strain was designated *Escherichia coli* AJ13069 strain and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

Examples of parent strains which can be used to derive L-lysine-producing bacteria can also include strains in which expression of one or more genes encoding an L-lysine biosynthetic enzyme are enhanced. Examples of the enzymes involved in L-lysine biosynthesis include, but are not limited to, dihydrodipicolinate synthase (dapA), aspartokinase (lysC), dihydrodipicolinate reductase (dapB), diaminopimelate decarboxylase (lysA), diaminopimelate dehydrogenase (ddh) (U.S. Pat. No. 6,040,160), phosphoenolpyrvate carboxylase (ppc), aspartate semialdehyde dehydrogenease (asd), and aspartase (aspA) (EP 1253195 A). In addition, the parent strains can have increased expression of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), and combinations thereof.

Examples of parent strains for deriving L-lysine-producing bacteria also include strains having decreased or eliminated activity of an enzyme that catalyzes a reaction for generating a compound other than L-lysine by branching off from the biosynthetic pathway of L-lysine. Examples of the enzymes that catalyze a reaction for generating a compound other than L-lysine by branching off from the biosynthetic pathway of L-lysine include homoserine dehydrogenase (WO 95/23864), lysine decarboxylase (U.S. Pat. No. 5,827,698), and the malic enzyme (WO2005/010175).

An example of an L-lysine producing strain is *E. coli* WC196 Δ cadA Δ ldc/pCABD2 (WO2006/078039). This strain was obtained by introducing the pCABD2 plasmid (U.S. Pat. No. 6,040,160) into the WC1-96 strain, in which the cadA and ldcC genes coding for lysine decarboxylase are disrupted. The pCABD2 plasmid contains the dapA gene derived from *Escherichia coli*, which has been mutated to encode dihydrodipicolinate synthase (DDPS) which is desensitized to the feedback inhibition by L-lysine, the lysC gene derived from *Escherichia coli*, which has been mutated to encode aspartokinase III, which is desensitized to feedback inhibition by L-lysine, the dapB gene derived from *Escherichia coli* coding for dihydrodipicolinate reductase, and the ddh gene derived from *Brevibacterium lactofermentum* coding for diaminopimelate dehydrogenase.

L-Cysteine-Producing Bacteria

Examples of parent strains which can be used to derive L-cysteine-producing bacteria include, but are not limited to, strains belonging to the genus *Escherichia*, such as *E. coli* JM15 which has been transformed with different cysE alleles coding for feedback-resistant serine acetyltransferases (U.S. Pat. No. 6,218,168, Russian patent application 2003121601), *E. coli* W3110 which over-expresses genes which encode proteins suitable for secreting toxic substances (U.S. Pat. No. 5,972,663), *E. coli* strains with decreased cysteine desulfohydrase activity (JP11155571A2); and *E. coli* W3110 with increased activity of a positive transcriptional regulator for the cysteine regulon encoded by the cysB gene (WO01/27307A1).

L-Leucine-Producing Bacteria

Examples of parent strains which can be used to derive L-leucine-producing bacteria can include, but are not limited to, strains belonging to the genus *Escherichia*, such as *E. coli* strains resistant to leucine (for example, the strain 57 (VKPM B-7386, U.S. Pat. No. 6,124,121)) or leucine analogs including β-2-thienylalanine, 3-hydroxyleucine, 4-azaleucine, 5,5,5-trifluoroleucine (JP 62-34397 B and JP 8-70879 A); and *E. coli* strains obtained by the genetic engineering method described in WO96/06926; *E. coli* H-9068 (JP 8-70879 A), and the like.

The bacterium can be improved by enhancing the expression of one or more genes involved in L-leucine biosynthesis. Examples of these genes include those of the leuABCD operon, which include a leuA gene, which has been mutated so that it encodes isopropylmalate synthase, which is resistant to feedback inhibition by L-leucine (U.S. Pat. No. 6,403,342). In addition, the bacterium can be improved by enhancing the expression of one or more genes coding for proteins that excrete L-amino acids from the bacterial cell. Examples of such genes include the b2682 and b2683 genes (ygaZH genes) (EP 1239041 A2).

L-Histidine-Producing Bacteria

Examples of parent strains which can be used to derive L-histidine-producing bacteria can include, but are not limited to, strains belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP1085087); *E. coli* AI80/pFM201 (U.S. Pat. No. 6,258,554) and the like.

Examples of parent strains for deriving L-histidine-producing bacteria also include strains in which expression of one or more genes encoding an L-histidine biosynthetic enzyme are enhanced. Examples of these L-histidine-biosynthetic enzymes include ATP phosphoribosyltransferase (hisG), phosphoribosyl AMP cyclohydrolase (hisI), phosphoribosyl-ATP pyrophosphohydrolase (hisIE), phosphoribosylformimino-5-aminoimidazole carboxamide ribotide isomerase (hisA), amidotransferase (hisH), histidinol phosphate aminotransferase (hisC), histidinol phosphatase (hisB), histidinol dehydrogenase (hisD), and so forth.

The genes encoding the L-histidine biosynthetic enzyme (hisG, hisBHAFI) are inhibited by L-histidine, and therefore, the L-histidine-producing ability can also be efficiently enhanced by introducing a mutation that induces resistance to the feedback inhibition into ATP phosphoribosyltransferase (hisG) (Russian Patent Nos. 2003677 and 2119536).

Specific examples of strains having an L-histidine-producing ability include *E. coli* FERM-P 5038 and 5048 which have been transformed with a vector carrying a DNA encoding an L-histidine-biosynthetic enzyme (JP 56-005099 A), *E. coli* strains transformed with rht, a gene for an amino acid-export (EP1016710A), *E. coli* 80 strain imparted with sulfaguanidine, DL-1,2,4-triazole-3-alanine, and streptomycin-resistance (VKPM B-7270, Russian Patent No. 2119536).

L-Glutamic Acid-Producing Bacteria

Examples of parent strains which can be used to derive L-glutamic acid-producing bacteria can include, but are not limited to, strains belonging to the genus *Escherichia*, such as *E. coli* VL334thrC+ (EP 1172433). *E. coli* VL334 (VKPM B-1641) is auxotrophic for L-isoleucine and L-threonine and is mutated in the thrC and ilvA genes (U.S. Pat. No. 4,278, 765). A wild-type allele of the thrC gene was transferred by general transduction using a bacteriophage P1 grown on the wild-type *E. coli* strain K12 (VKPM B-7). As a result, an L-isoleucine auxotrophic strain VL334thrC+ (VKPM B-8961) was obtained.

Examples of L-glutamic acid-producing bacteria and parent strains which can be used to derive L-glutamic acid-producing bacteria include, but are not limited to, strains in which expression of one or more genes encoding an L-glutamic acid biosynthetic enzyme is enhanced. Examples of such genes include the genes encoding glutamate dehydrogenase (gdhA), glutamine synthetase (glnA), glutamate synthetase (gltAB), isocitrate dehydrogenase (icdA), aconitate hydratase (acnA, acnB), citrate synthase (gltA), methyl citrate synthase gene (prpC), phosphoenolpyruvate carboxylase (ppc), pyruvate dehydrogenase (aceEF, 1pdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), and so forth. Among these enzymes, glutamate dehydrogenase, citrate synthase, phosphoenolpyruvate carboxylase, and methyl citrate synthase are particular examples.

Examples of strains which have been modified so that expression of the citrate synthetase gene, the phosphoenolpyruvate carboxylase gene, and/or the glutamate dehydrogenase gene is enhanced, include those disclosed in EP 1078989 A, EP 955368 A, and EP 952221A.

Examples of parent strains which can be used to derive the L-glutamic acid-producing bacteria can also include strains that have a decreased or eliminated activity of an enzyme that catalyzes synthesis of a compound other than L-glutamic acid, and branches off from the L-glutamic acid biosynthesis pathway. Examples of such enzymes include 2-oxoglutarate dehydrogenase (α-ketoglutarate dehydrogenase) (sucA), isocitrate lyase (aceA), phosphotransacetylase (pta), acetate kinase (ack), acetohydroxy acid synthase (ilvG), acetolactate synthase (ilvI), formate acetyltransferase (pfl), lactate dehydrogenase (ldh), and glutamate decarboxylase (gadAB). *Escherichia* bacteria without α-ketoglutarate dehydrogenase activity or with reduced α-ketoglutarate dehydrogenase activity and methods to obtain such bacteria are described in U.S. Pat. Nos. 5,378,616 and 5,573,945.

Specific examples include the followings:
*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is obtained by disrupting the 2-oxoglutarate dehydrogenase gene (sucA gene) of *E. coli* W3110. This strain is completely deficient in 2-oxoglutarate dehydrogenase.

Other examples of L-glutamic acid-producing bacterium include *Escherichia* bacteria that are resistant to an aspartic acid antimetabolite. These strains can also be deficient in α-ketoglutarate dehydrogenase activity and include, for example, *E. coli* AJ13199 (FERM BP-5807) (U.S. Pat. No. 5,908,768), FERM P-12379, which additionally is unable to decompose L-glutamic acid (U.S. Pat. No. 5,393,671); AJ13138 (FERM BP-5565) (U.S. Pat. No. 6,110,714), and so forth.

An example of an L-glutamic acid-producing bacterium that belongs to the genus *Pantoea ananatis* is, but is not limited to, the *Pantoea ananatis* AJ13355 strain. This strain was isolated from soil in Iwata-shi, Shizuoka-ken, Japan, and was identified as being able to proliferate in a medium containing L-glutamic acid and a carbon source at a low pH. The *Pantoea ananatis* AJ13355 strain was deposited at the National Institute of Advanced Industrial Science and Technology, International Patent Organism Depositary (Tsukuba Central 6, 1-1, Higashi 1-Chome, Tsukuba-shi, Ibaraki-ken, 305-8566, Japan) on Feb. 19, 1998 and received an accession number of FERM P-16644. It was then converted to an international deposit under the provisions of Budapest Treaty on Jan. 11, 1999 and received an accession number of FERM BP-6614. This strain was originally identified as *Enterobacter agglomerans* when it was isolated, and deposited as *Enterobacter agglomerans* AJ13355. However, it was recently re-classified as *Pantoea ananatis* on the basis of nucleotide sequencing of 16S rRNA and so forth.

Furthermore, the α-ketoglutarate dehydrogenase (α KGDH) activity can be eliminated or reduced in bacteria belonging to the genus *Pantoea*. Examples of such a strain include AJ13356 (U.S. Pat. No. 6,331,419), which was derived by deleting the α KGDH-E1 subunit gene (sucA) in AJ13355, and the SC17sucA strain (U.S. Pat. No. 6,596,517), which also does not have the sucA gene, and was selected from AJ13355 for its low phlegm production properties. The AJ13356 strain was deposited at the National Institute of Bioscience and Human-Technology, Agency of Industrial Science and Technology, Ministry of International Trade and Industry (currently, the independent administrative agency, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566)) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. Although the AJ13355 and AJ13356 strains were deposited at the aforedescribed depository as *Enterobacter agglomerans*, they are referred to as *Pantoea ananatis* in this specification. The SC17sucA strain was assigned the private number of AJ417, and deposited at the National Institute of Advanced Industrial Science and Technology, International Patent Organism Depositary on Feb. 26, 2004, under an accession number of FERM BP-08646.

Examples of L-glutamic acid-producing *Pantoea ananatis* bacteria further include SC17sucA/RSFCPG+pSTVCB, AJ13601, NP106, and NA1. The SC17sucA/RSFCPG+pSTVCB strain was obtained by introducing the plasmid RSFCPG containing the citrate synthase gene (gltA), phosphoenolpyruvate carboxylase gene (ppsA), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain was selected from the SC17sucA/RSFCPG+pSTVCB strain for its resistance to high concentrations of L-glutamic acid at a low pH. Furthermore, the NP106 strain was derived from the AJ13601 strain by eliminating the RSFCPG+pSTVCB plasmid as described in the examples. The AJ13601 strain was deposited at the National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Aug. 18, 1999, and assigned accession number FERM P-17516. Then, the deposit was converted into an international deposit under the provisions of the Budapest Treaty on Jul. 6, 2000, and assigned an accession number FERM BP-7207.

L-Phenylalanine-Producing Bacteria

Examples of L-phenylalanine-producing bacteria and parent strains which can be used to derive L-phenylalanine-producing bacteria can include, but are not limited to, Escherichia bacterial strains, such as E. coli AJ12739 (tyrA::Tn10, tyrR) (VKPM B-8197) which lacks chorismate mutase-prephenate dehydrogenase and the tyrosine repressor (WO03/044191), E. coli HW1089 (ATCC 55371) which contains the pheA34 gene coding for chorismate mutase-prephenate dehydratase which has been mutated to be desensitized to feedback inhibition (U.S. Pat. No. 5,354,672), E. coli MWEC101-b (KR8903681), E. coli NRRL B-12141, NRRL B-12145, NRRL B-12146, and NRRL B-12147 (U.S. Pat. No. 4,407,952). Also, the following strains can be used to derive L-phenylalanine producing bacteria: E. coli K-12 [W3110(tyrA)/pPHAD] (FERM BP-3566) which contains genes coding for chorismate mutase-prephenate dehydratase, which has been mutated to be desensitized to feedback inhibition, E. coli K-12 [W3110(tyrA)/pPHAD] (FERM BP-12659), E. coli K-12 [W3110(tyrA)/pPHATerm] (FERM BP-12662), and E. coli K-12 [W3110(tyrA)/pBR-aroG4, pACMAB] (also known as AJ12604 (FERM BP-3579) (EP 488424 B1). Furthermore, Escherichia L-phenylalanine-producing bacteria with enhanced activity of the protein encoded by the yedA gene or the yddG gene can also be used (U.S. Patent Published Applications Nos. 2003/0148473 A1 and 2003/0157667 A1, WO03/044192).

L-Tryptophan-Producing Bacteria

Examples of parent strains which can be used to derive the L-tryptophan-producing bacteria can include, but are not limited to, strains belonging to the genus Escherichia, such as E. coli JP4735/pMU3028 (DSM10122) and JP6015/pMU91 (DSM10123) deficient in the tryptophanyl-tRNA synthetase encoded by mutant trpS gene (U.S. Pat. No. 5,756,345); E. coli SV164 (pGH5) having a serA allele encoding phosphoglycerate dehydrogenase resistant to feedback inhibition by serine and a trpE allele encoding anthranilate synthase resistant to feedback inhibition by tryptophan (U.S. Pat. No. 6,180,373); E. coli AGX17 (pGX44) (NRRL B-12263) and AGX6(pGX50)aroP(NRRL B-12264) deficient in the enzyme tryptophanase (U.S. Pat. No. 4,371,614); E. coli AGX17/pGX50,pACKG4-pps in which a phosphoenolpyruvate-producing ability is enhanced (WO9708333, U.S. Pat. No. 6,319,696), and the like. Furthermore, L-tryptophan producing bacteria belonging to the genus Escherichia which have an enhanced activity of the protein encoded by the yedA gene or the yddG gene can also be used (U.S. patent applications 2003/0148473 A1 and 2003/0157667 A1).

Examples of L-tryptophan-producing bacteria and parent strains which can be used to derive L-tryptophan-producing bacteria can also include strains in which one or more activities of the following enzymes are enhanced: anthranilate synthase (trpE), phosphoglycerate dehydrogenase (serA), 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), chorismate synthase (aroC), prephenate dehydratase, chorismate mutase, and tryptophan synthase (trpAB). Prephenate dehydratase and chorismate mutase are encoded by the pheA gene as a bifunctional enzyme (CM-PD). Among these enzymes, phosphoglycerate dehydrogenase, 3-deoxy-D-arabinoheptulosonate-7-phosphate synthase, 3-dehydroquinate synthase, shikimate dehydratase, shikimate kinase, 5-enolpyruvylshikimate-3-phosphate synthase, chorismate synthase, prephenate dehydratase, and chorismate mutase-prephenate dehydratase are especially preferred. Anthranilate synthase and phosphoglycerate dehydrogenase both suffer from feedback inhibition by L-tryptophan and L-serine, and therefore a mutation desensitizing feedback inhibition can be introduced into the genes encoding these enzymes. Specific examples of strains having such a mutation include E. coli SV164 and a transformant strain obtained by introducing pGH5 (WO94/08031) into SV164, resulting in feedback-desensitized phosphoglycerate dehydrogenase due to a mutant serA gene.

Examples of parent strains which can be used to derive the L-tryptophan-producing bacteria also include strains transformed with the tryptophan operon which contains a gene encoding desensitized anthranilate synthase (JP 57-71397 A, JP 62-244382 A, U.S. Pat. No. 4,371,614). Moreover, L-tryptophan-producing ability can be imparted by enhancing expression of a gene that encodes tryptophan synthase, among tryptophan operons (trpBA). The tryptophan synthase consists of α and β subunits, which are encoded by trpA and trpB, respectively. In addition, L-tryptophan-producing ability can be improved by enhancing expression of the isocitrate lyase-malate synthase operon (WO2005/103275).

L-Proline-Producing Bacteria

Examples of parent strains which can be used to derive L-proline-producing bacteria can include, but are not limited to, strains belonging to the genus Escherichia, such as E. coli 702ilvA (VKPM B-8012), which is deficient in the ilvA gene and is able to produce L-proline (EP 1172433).

The bacterium can be improved by enhancing the expression of one or more genes involved in L-proline biosynthesis. Examples of genes for L-proline producing bacteria include the proB gene coding for glutamate kinase which is desensitized to feedback inhibition by L-proline (DE Patent 3127361). In addition, the bacterium can be improved by enhancing the expression of one or more genes coding for proteins excreting L-amino acid from the bacterial cell. Such genes include the b2682 and b2683 genes (ygaZH genes) (EP1239041 A2).

Examples of bacteria belonging to the genus Escherichia which have an activity to produce L-proline include, but are not limited to the following E. coli strains: NRRL B-12403 and NRRL B-12404 (GB Patent 2075056), VKPM B-8012 (Russian patent application 2000124295), plasmid mutants described in DE Patent 3127361, and plasmid mutants described by Bloom F. R. et al (The 15th Miami winter symposium, 1983, p. 34).

L-Arginine-Producing Bacteria

Examples of parent strains which can be used to derive L-arginine-producing bacteria can include, but are not limited to, strains belonging to the genus Escherichia, such as E. coli strain 237 (VKPM B-7925) (U.S. Patent Application 2002/058315 A1) and its derivative strains harboring mutant N-acetylglutamate synthase (Russian Patent Application No. 2001112869), E. coli strain 382 (VKPM B-7926) (EP1170358A1), and an arginine-producing strain into which the argA gene encoding N-acetylglutamate synthetase is introduced (EP1170361A1).

Examples of parent strains which can be used to derive L-arginine producing bacteria also include strains in which expression of one or more genes encoding an L-arginine biosynthetic enzyme are enhanced. Examples of the L-arginine biosynthetic enzymes include N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-Valine-Producing Bacteria

Example of parent strains which can be used to derive L-valine-producing bacteria can include, but are not limited to, strains which have been modified to overexpress the ilvGMEDA operon (U.S. Pat. No. 5,998,178). It is desirable to remove the region of the ilvGMEDA operon, which is required for attenuation so that expression of the operon is not attenuated by the L-valine that is produced. Furthermore, the ilvA gene in the operon is desirably disrupted so that threonine deaminase activity is decreased.

Examples of parent strains which can be used to derive L-valine-producing bacteria can also include mutants of amino-acyl t-RNA synthetase (U.S. Pat. No. 5,658,766). For example, E. coli VL1970, which has a mutation in the ileS gene encoding isoleucine tRNA synthetase, can be used. E. coli VL1970 has been deposited in the Russian National Collection of Industrial Microorganisms (VKPM) (Russia, 113545 Moscow, 1 Dorozhny Proezd.) on Jun. 24, 1988 under accession number VKPM B-4411.

Furthermore, mutants requiring lipoic acid for growth and/or lacking H$^+$-ATPase can also be used (WO96/06926).

L-Isoleucine-Producing Bacteria

Examples of parent strains which can be used to derive L-isoleucine producing bacteria can include, but are not limited to, mutants having resistance to 6-dimethylaminopurine (JP 5-304969 A), mutants having resistance to an isoleucine analogue such as thiaisoleucine and isoleucine hydroxamate, and mutants additionally having resistance to DL-ethionine and/or arginine hydroxamate (JP 5-130882 A). In addition, recombinant strains transformed with genes encoding proteins involved in L-isoleucine biosynthesis, such as threonine deaminase and acetohydroxate synthase, can also be used (JP 2-458 A, FR 0356739, and U.S. Pat. No. 5,998,178).

L-Methionine-Producing Bacteria

Examples of parent strains which can be used to derive the L-methionine-producing bacteria can include, but not limited to, L-threonine-auxotrophic strain and norleucine-resistant strain (JP2000-139471). Moreover, examples of parent strains which can be used to derive the L-methionine-producing bacteria can also include methionine repressor-deficient strain and recombinant strains transformed with a gene encoding a protein involved in L-methionine biosynthesis, such as homoserine transsuccinylase and cystathionine γ-synthase (JP2000-139471).

When the aforedescribed L-amino acid-producing bacteria are bred by genetic recombination, the genes are not limited to the genes having the genetic information cited herein or genes having known sequences. Variants of these genes, that is, genes having conservative mutations such as homologues or artificially modified genes, can also be used so long as the functions of the encoded proteins are not degraded. That is, genes are encompassed which encode variants of the known amino acid sequence, in that they can contain one or several substitutions, deletions, insertions, additions, or the like, of one or several amino acid residues at one or several positions. The description on the "conservative variant" about genes involved in fatty acid utilization in the section described below is also applied to the enzymes and genes described above.

<2-2> Enhancing the Ability to Use Fatty Acid

The bacterium can be obtained by modifying the above-described bacterium having an L-amino acid-producing ability such that ability thereof to use a fatty acid is enhanced. It can refer to a bacterium modified such that expression is attenuated, fadR gene is deficient, expression of fadI gene is enhanced, expression of fadJ gene is enhanced, expression of fadL gene is enhanced, expression of fadE gene is enhanced, expression of fadD gene is enhanced, expression of fadB gene is enhanced, expression of fadA gene is enhanced, expression of fadBA operon is enhanced, expression of fadIJ operon is enhanced, and/or expression of cyoABCDE is enhanced.

The term "fadR gene" can mean a gene encoding transcription factor FadR having ability to bind DNA which is found the Enterobacteriaceae family and controls fatty acid metabolism (DiRusso, C. C. et al. 1992. J. Biol. Chem. 267: 8685-8691; DiRusso, C. C. et al. 1993. Mol. Microbiol. 7: 311-322). Specifically, as fadR gene of Escherichia coli, a gene having the nucleotide sequence shown in SEQ ID NO: 1, which is located in nucleotide 1234161 to nucleotide 1234880 of Escherichia coli genomic sequence (GenBank Accession No. U00096) is exemplified. SEQ ID NO: 2 shows the amino acid sequence encoded by the above gene.

A decrease in an activity of FadR as a transcription factor can be attained by attenuating expression of fadR gene or deleting the gene. Specifically, it can be achieved by deleting a gene encoding FadR on the chromosome, specifically a part or the entire region of the coding region of fadR gene; and by modifying an expression regulatory sequence such as a promoter or Shine-Dalgarno (SD) sequence thereof. Also, the level of expression of the gene can be decreased by modifying a non-translation region other than the expression regulatory region. Furthermore, the whole gene can be deleted together with a sequence in the vicinity of the gene on the chromosome. In addition, it can be achieved by introducing amino acid substitution in the region encoding FadR on the chromosome (missense mutations) by gene recombination and introducing a termination codon (nonsense mutations); or by introducing frameshift mutations in which one to two bases are added or deleted (Wang, J. P. et al. 2006. J. Agric. Food Chem. 54: 9405-9410; Winkler, W. C. 2005. Cum Opin. Chem. Biol. 9: 594-602; Qiu, Z. and Goodman, M. F. 1997. J. Biol. Chem. 272: 8611-8617; Wente, S. R. and Schachman, H. K. 1991. J. Biol. Chem. 266: 20833-20839).

Transcription regulatory activity of FadR in cells can be decreased by using homologous recombination, by deleting a part or the entire region of the expression regulatory sequence of the gene for example a promoter region, or the coding region or the noncoding region on the chromosome; or by inserting the other sequences into these regions. However, as long as it is modification to decrease the transcription regulatory activity, a usual mutation treatment by irradiation with X ray or ultra violet ray, or by a mutagenesis agent such as N-methyl-N'-nitro-N-nitrosoguanidine can be employed.

An expression regulatory sequence can be modified by not less than one nucleotide, not less than two nucleotides, or not less than 3 nucleotides. When a coding region is deleted, as long as the function of generated FadR to regulate transcription thereof is decreased or deleted, the region to be deleted can be any of the N terminus region, an internal region or the C terminus region. Although it is desirable that a DNA binding domain be included, the entire coding region can be deleted. Usually, the longer the deleted region, inactivation of the gene can be achieved with more certainty. In addition, reading frames upstream and downstream of the region to be deleted do not need to be identical.

When other sequences are inserted into a coding region, the insertion can be carried out in any region of a gene. The longer the sequence to be inserted, inactivation of a gene encoding a transcription factor can be achieved with more certainty.

Reading frames upstream and downstream of the region to be inserted do not need to be identical. Other sequences are not particularly limited as long as insertion thereof leads to a decrease in or deletion of the function of the transcription factor. Examples include antibiotic resistance genes, and transposons carrying genes useful for L-amino acid production.

Modification of a gene on the chromosome described above can be achieved, for example, by preparing a deletion-type gene lacking a partial sequence of the gene which is modified such that normally functioning enzyme proteins are not generated; transforming cells with DNA containing such a gene; allowing homologous recombination to take place between the deletion-type gene and the gene on the chromosome; and replacing the gene on the chromosome with the deletion-type gene. A transcriptional factor encoded by the deletion-type gene has, even when generated, a different spatial structure from a wild type transcriptional factor and function thereof is decreased or lost. This kind of gene disruption by gene substitution using homologous recombination can be carried out by methods using linear DNA, such as a Red driven integration method or a combination method of the Red driven integration and an excision system derived from λ phage, methods using a plasmid containing temperature-sensitive replication origin or plasmid capable of conjugative transfer; and a method using a suicide vector which does not have a replication origin in a host (U.S. Pat. No. 6,303,383 or Japanese Laid-Open Patent Application No. 05-007491). Attenuated expression of fadR gene can be confirmed by Northern hybridization, RT-PCR or the like. Deletion of fadR gene can be confirmed by Southern blotting or the like (Sambrook, J. and Russell, D. W. 2001. Molecular Cloning A Laboratory Manual/Third Edition. Cold Spring Harbor Laboratory Press, New York).

The above-described description on decreased activity of the transcriptional factor can be applied to "decrease in activity" of other enzymes described above or "disruption" of other genes.

The term "fadL gene" can mean a gene encoding a transporter of the outer membrane capable of taking up a long chain fatty acid, which is found in the Enterobacteriaceae family (Kumar, G. B. and Black, P. N. 1993. J. Biol. Chem. 268: 15469-15476; Stenberg, F. et al. 2005. J. Biol. Chem. 280: 34409-34419).

Increase in the FadL activity by increasing expression of fadL gene can be confirmed by comparing the activity of a bacterium to take up long-chain fatty acids before and after amplifying the fadL gene. For instance, the activity to take up oleic acid can be measured in accordance with, for example, the method of Kumar and Black (Kumar, G. B. and Black, P. N. 1993. J. Biol. Chem. 268: 15469-15476). Cells collected after culturing are allowed to react with $^3$H labeled oleic acid and measurement can be carried out by comparing the radioactivity taken up after washing. The activity to take up is expressed with the amount of $^3$H oleic acid taken up (nM) per minute per whole cell protein. It is desirable that the activity to take up increases 1.5 folds or more, 2 folds or more, or 3 folds or more as compared with a parent or unmodified strain. Activity of FadL to bind with the long-chain fatty acid can also be measured. Expression of FadL protein can be confirmed by a method such as Western blotting (Kumar, G. B. and Black, P. N. 1993. J. Biol. Chem. 268: 15469-15476). Also, by Northern hybridization, RT-PCR or the like (Sambrook, J. and Russell, D. W. 2001. Molecular Cloning A Laboratory Manual/Third Edition. Cold Spring Harbor Laboratory Press, New York), an increase in the amount of mRNA of fadL gene can be confirmed.

A specific example of a gene encoding FadL includes a gene located as fadL gene of *Escherichia coli* at nucleotide 2459322 to nucleotide 2460668 of *Escherichia coli* genomic sequence (Genbank Accession No. U00096) and having the nucleotide sequence shown in SEQ ID NO: 3. SEQ ID NO: 4 shows the amino acid sequence encoded by the above gene.

The term "fadD gene" can mean a gene encoding an enzyme having fatty acyl-CoA synthetase activity which generates fatty acyl-CoA from a long chain fatty acid as well as taking up it through the inner membrane, which is found in the Enterobacteriaceae family (Dirusso, C. C. and Black, P. N. 2004. J. Biol. Chem. 279: 49563-49566; Schmelter, T. et al. 2004. J. Biol. Chem. 279: 24163-24170).

A fatty acyl-CoA synthetase activity can refer to an activity to catalyze the following reaction (EC 6.2.1.3).

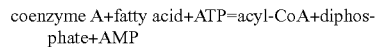
coenzyme A+fatty acid+ATP=acyl-CoA+diphosphate+AMP

Increase in FadD activity by increasing expression of fadD gene can be confirmed by comparing the activity of a bacterium to take up long-chain fatty acids before and after the amplification of fadD gene. For instance, the activity to take up oleic acid can be measured in accordance with, for example, the method of Schmelter et al. (Schmelter, T. et al. 2004. J. Biol. Chem. 279: 24163-24170). The measurement can be carried out by preparing inner membrane vesicles from cells collected after culturing, adding $^3$H labeled oleic acid thereto after trapping ATP and coenzyme A, and comparing the radioactivity taken up after washing. The activity to take up is expressed with the amount of $^3$H oleic acid taken up (nM) per minute per whole cell protein. It is desirable that the activity to take up increases 1.5 folds or more, 2 folds or more, or 3 folds or more as compared with a parent or unmodified strain. An increase in fatty acyl-CoA synthetase activity for the long-chain fatty acid can also be measured. An increase in expression of the protein can be confirmed by a method such as Western blotting. Also, by Northern hybridization, RT-PCR or the like, an increase in the amount of mRNA of fadD gene can be confirmed.

A specific example of a gene encoding FadD includes a gene located as fadD gene of *Escherichia coli* at nucleotide 1887770 to nucleotide 1886085 (complementary strand) of *Escherichia coli* genomic sequence (GenBank Accession No. U00096) and having the nucleotide sequence shown in SEQ ID NO: 5. SEQ ID NO: 6 shows the amino acid sequence encoded by the above gene.

The term "fadE gene" can mean a gene encoding an enzyme having acyl-CoA dehydrogenase activity which oxidizes fatty acyl-CoA, which is found in the Enterobacteriaceae family (O'Brien, W. J. and Frerman, F. E. 1977. J. Bacteriol. 132: 532-540; Campbell, J. W. and Cronan, J. E. 2002. J. Bacteriol. 184: 3759-3764).

An acyl-CoA dehydrogenase activity can refer to an activity to catalyze the following reaction (EC 1.3.99.3).

acyl-CoA+FAD=FADH$_2$+Δ2-enoyl-CoA

Increase in the FadE activity by increasing expression of fadE gene can be confirmed by comparing the oxidative activity of a bacterium before and after amplification of fadE gene. For instance, the activity to oxidize oleyl CoA can be measured in accordance with, for example, the method of Brien and Frerman (O'Brien, W. J. and Frerman, F. E. 1977. J. Bacteriol. 132: 532-540). The activity measurement can be carried out by preparing a crude enzyme extract solution from cells collected after culturing, adding the extract solution to a reaction solution containing MTT (3-(4,5-dimethylthiazol-2-yl)-2,5-diphenyltetrazolium bromide) and oleyl CoA, and measuring absorbance at 546 nm for the amount of reduced MTT. The acyl-CoA dehydrogenase activity is expressed with the amount of oxidization of oleyl CoA (nM) per minute per protein of the crude enzyme extract solution. It is desirable that the FadE activity increases 1.5 folds or more, 2 folds or more, or 3 folds or more, as compared with a parent or unmodified strain. Expression of the protein can be confirmed by a method such as Western blotting. Also, by Northern hybridization, RT-PCR or the like, an increase in the amount of mRNA of fadE gene can be confirmed.

A specific example of a gene encoding FadE includes a gene located as fadE gene of *Escherichia coli* at nucleotide 243303 to nucleotide 240859 (complementary strand) of *Escherichia coli* genomic sequence (GenBank Accession No. U00096) and having the nucleotide sequence shown in SEQ ID NO: 7. SEQ ID NO: 8 shows the amino acid sequence encoded by the above gene.

The term "fadB gene" can mean a gene encoding an enzyme which is the α component of a fatty acid oxidation complex and catalyzes four activities of enoyl-CoA hydratase, 3-hydroxyacyl-CoA dehydrogenase, 3-hydroxyacyl-CoA epimerase and Δ 3-cis-Δ 2-trans-enoyl-CoA isomerase, the gene being found in the Enterobacteriaceae family (Pramanik, A. et al. 1979. J. Bacteriol. 137: 469-473; Yang, S. Y. and Schulz, H. 1983. J. Biol. Chem. 258: 9780-9785).

An enoyl-CoA hydratase activity can refer to an activity to catalyze the following reaction (EC 4.2.1.17).

H$_2$O+trans-2-enoyl-CoA=L-3-hydroxyacyl-CoA 3-hydroxyacyl-CoA dehydrogenase activity can refer to an activity to catalyze the following reaction (EC 1.1.1.35).

NAD+L-3-hydroxyacyl-CoA=NADH+3-ketoacyl-CoA 3-hydroxyacyl-CoA epimerase activity can refer to an activity to catalyze the following reaction (EC 5.1.2.3).

D-3-hydroxyacyl-CoA=L-3-hydroxyacyl-CoA

Δ 3-cis-Δ 2-trans-enoyl-CoA isomerase activity can refer to an activity to catalyze the following reaction (EC 5.3.3.8).

cis-3-enoyl-CoA=trans-2-enoyl-CoA

An increase in the FadB activity by increasing expression of fadB gene can be confirmed, for example, by comparing hydration activity of crotonyl CoA and reduction activity of acetoacetyl CoA in a bacterium before and after the amplification of fadB gene. Four activities of FadB can be measured in accordance with, for example, the method of Binstock and Schulz (Binstock, J. F. and Schulz, H. 1981. Methods Enzymol. 71 (Pt C): 403-411).

The measurement of enoyl-CoA hydratase activity can be carried out by preparing a crude enzyme extract solution from cells collected after culturing, adding the extract solution to a reaction solution containing crotonyl CoA, and measuring absorbance at 263 nm for the amount of hydrated crotonyl CoA.

The enoyl-CoA hydratase activity is, for example, expressed with the amount of hydration of crotonyl CoA (nM) per minute per protein of the crude enzyme extract solution.

In addition, the measurement of 3-hydroxyacyl-CoA dehydrogenase activity can be carried out by preparing a crude enzyme extract solution from cells collected after culturing, adding the extract solution to a reaction solution containing acetoacetyl CoA and NADH, and measuring absorbance at 340 nm for the amount of dehydrogenated NADH.

The 3-hydroxyacyl-CoA dehydrogenase activity is expressed with the amount of oxidation of NADH (nM) per minute per protein of the crude enzyme extract solution.

It is desirable that the FadB activity increases 1.5 folds or more, 2 folds or more, or 3 folds or more, as compared with a parent or unmodified strain. Expression of the protein can be confirmed by a method such as Western blotting. Also, by Northern hybridization, RT-PCR or the like, an increase in the amount of mRNA of fadB gene can be confirmed.

A specific example of a gene encoding FadB includes a gene located as fadB gene of *Escherichia coli* at nucleotide 4028994 to nucleotide 4026805 (complementary strand) of *Escherichia coli* genomic sequence (GenBank Accession No. U00096) and having the nucleotide sequence shown in SEQ ID NO: 9. SEQ ID NO: 10 shows the amino acid sequence encoded by the above gene.

The term "fadA gene" can mean a gene encoding an enzyme which is the β component of a fatty acid oxidation complex and catalyzes a 3-ketoacyl-CoA thiolase activity, the gene being found in the Enterobacteriaceae family (Pramanik, A. et al. 1979. J. Bacteriol. 137: 469-473).

3-ketoacyl-CoA thiolase activity can refer to an activity to catalyze the following reaction (EC 2.3.1.16).

3-ketoacyl-CoA+coenzyme A=acyl-CoA+acetyl-CoA

Increase in FadA activity by increasing expression of fadA gene can be confirmed, for example, by comparing thiolase activity of acetoacetyl CoA in a bacterium before and after the amplification of fadA gene. The FadA activity can be measured in accordance with, for example, the method of Binstock and Schulz (Binstock, J. F. and Schulz, H. 1981. Methods Enzymol. 71 (Pt C): 403-411).

The measurement of 3-ketoacyl-CoA thiolase activity can be carried out by preparing a crude enzyme extract solution from cells collected after culturing, adding the extract solution to a reaction solution containing acetoacetyl CoA, magnesium and CoA, and measuring absorbance at 303 nm for the amount of decrease in a complex of magnesium ion and enol acid, which is a substrate. The 3-ketoacyl-CoA thiolase activity is expressed with the amount of decrease in acetoacetyl CoA (nM) per minute per protein of the crude enzyme extract solution. It is desirable that the FadA activity increases 1.5 folds or more, 2 folds or more, or 3 folds or more, as compared with a parent or unmodified strain. Expression of the protein can be confirmed by a method such as Western blotting. Also, by Northern hybridization, RT-PCR or the like, an increase in the amount of mRNA of fadA gene can be confirmed.

A specific example of a gene encoding FadA includes a gene located as fadA gene of *Escherichia coli* at nucleotide 4026795 to nucleotide 4025632 (complementary strand) of *Escherichia coli* genomic sequence (GenBank Accession No. U00096) and having the nucleotide sequence shown in SEQ ID NO: 11. SEQ ID NO: 12 shows the amino acid sequence encoded by the above gene.

FadB and FadA form a complex in a fatty acid oxidation complex found in the Enterobacteriaceae family and also as a gene, forms fadBA operon (Yang, S. Y. et al. 1990. J. Biol. Chem. 265: 10424-10429). Thus, as fadBA operon, the whole operon can be amplified.

The term "cyoABCDE" can mean a group of genes encoding corresponding subunits of a cytochrome bo terminal oxidase complex which is one of the terminal oxidases found in the Enterobacteriaceae family. cyoB is a gene encoding the subunit I; cyoA is a gene encoding the subunit II; cyoC is a gene encoding the subunit III; cyoD is a gene encoding the subunit IV; and cyoE is a gene encoding an enzyme catalyzing a heme O synthase activity (Gennis, R. B. and Stewart, V.

1996. p. 217-261. In F. D. Neidhardt (ed.), *Escherichia coli* and *Salmonella* Cellular and Molecular Biology/Second Edition, American Society for Microbiology Press, Washington, D.C; Chepuri et al. 1990. J. Biol. Chem. 265: 11185-11192).

Terminal oxidase of a cytochrome bo terminal oxidase complex can refer to the following reactions (EC 1.10.2.- and 1.10.3.-), which show activity to oxidize oxygen with electrons received from ubiquinols as well as function as a proton pump effluxing two molecules of protons per electron (Puustinen, A. et al. 1991. Biochemistry 30: 3936-3942).

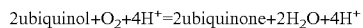

2ubiquinol+$O_2$+4$H^+$=2ubiquinone+2$H_2O$+4$H^+$

Increase in terminal oxidase activity by increasing expression of cyoABCDE gene can be confirmed, for example, by comparing ubiquinol oxidase activity in a bacterium before the increase with that in the bacterium after the increase. The ubiquinol oxidase activity can be measured in accordance with, for example, the method of Kita et al. (Kita, K. et al. 1986. Methods Enzymol. 126: 94-113). The measurement can be carried out by preparing a crude enzyme extract solution from cells collected after culturing, adding the extract solution to a reaction solution containing ubiquinol, and measuring the amount of decrease in oxygen, which also serves as a substrate, by an oxygen electrode. The ubiquinol oxidase activity is expressed with the amount of decrease in ubiquinol (nM) per minute per protein of the crude enzyme extract solution. It is desirable that the ubiquinol oxidase activity increases 1.5 folds or more, 2 folds or more, or 3 folds or more, compared with a parent or unmodified strain. Expression of each protein can be confirmed by a method such as Western blotting. Also, by Northern hybridization, RT-PCR or the like, an increase in the amount of mRNA of each gene can be confirmed.

A specific example of a gene encoding cyoA includes a gene located as cyoA gene of *Escherichia coli* at nucleotide 450834 to nucleotide 449887 (complementary strand) of *Escherichia coli* genomic sequence (GenBank Accession No. U00096) and having the nucleotide sequence shown in SEQ ID NO: 13. SEQ ID NO: 14 shows the amino acid sequence encoded by the above gene.

A specific example of a gene encoding cyoB includes a gene located as cyoB gene of *Escherichia coli* at nucleotide 449865 to nucleotide 447874 (complementary strand) of *Escherichia coli* genomic sequence (GenBank Accession No. U00096) and having the nucleotide sequence shown in SEQ ID NO: 15. SEQ ID NO: 16 shows the amino acid sequence encoded by the above gene.

A specific example of a gene encoding cyoC includes a gene located as cyoC gene of *Escherichia coli* at nucleotide 447884 to nucleotide 447270 (complementary strand) of *Escherichia coli* genomic sequence (GenBank Accession No. U00096) and having the nucleotide sequence shown in SEQ ID NO: 17. SEQ ID NO: 18 shows the amino acid sequence encoded by the above gene.

A specific example of a gene encoding cyoD includes a gene located as cyoD gene of *Escherichia coli* at nucleotide 447270 to nucleotide 446941 (complementary strand) of *Escherichia coli* genomic sequence (GenBank Accession No. U00096) and having the nucleotide sequence shown in SEQ ID NO: 19. SEQ ID NO: 20 shows the amino acid sequence encoded by the above gene.

A specific example of a gene encoding cyoE includes a gene located as cyoE gene of *Escherichia coli* at nucleotide 446929 to nucleotide 446039 (complementary strand) of *Escherichia coli* genomic sequence (GenBank Accession No. U00096) and having the nucleotide sequence shown in SEQ ID NO: 21. SEQ ID NO: 22 shows the amino acid sequence encoded by the above gene.

The term "fadJ gene" can mean a gene having homology with fadB gene and encoding an enzyme which is the a component of a fatty acid oxidation complex functioning under anaerobic conditions and aerobic conditions (Campbell, J. W. et al. 2003. Mol. Microbiol. 47(3): 793-805), and catalyzes four activities of enoyl-CoA hydratase, 3-hydroxyacyl-CoA dehydrogenase, 3-hydroxyacyl-CoA epimerase and Δ 3-cis-Δ 2-trans-enoyl-CoA isomerase (Pramanik, A. et al. 1979. J. Bacteriol. 137: 469-473; Yang, S. Y. and Schulz, H. 1983. J. Biol. Chem. 258: 9780-9785).

Enoyl-CoA hydratase activity can refer to an activity to catalyze the following reaction (EC 4.2.1.17).

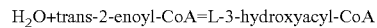

$H_2O$+trans-2-enoyl-CoA=L-3-hydroxyacyl-CoA 3-hydroxyacyl-CoA dehydrogenase activity can refer to an activity to catalyze the following reaction (EC 1.1.1.35).

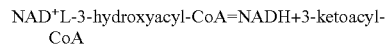

$NAD^+$L-3-hydroxyacyl-CoA=NADH+3-ketoacyl-CoA 3-hydroxyacyl-CoA epimerase activity can refer to an activity to catalyze the following reaction (EC 5.1.2.3).

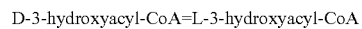

D-3-hydroxyacyl-CoA=L-3-hydroxyacyl-CoA

Δ 3-cis-Δ 2-trans-enoyl-CoA isomerase activity can refer to an activity to catalyze the following reaction (EC 5.3.3.8).

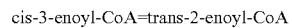

cis-3-enoyl-CoA=trans-2-enoyl-CoA

An increase in the FadJ activity by increasing expression of fadJ gene can be confirmed, for example, by comparing hydration activity of crotonyl CoA and reduction activity of acetoacetyl CoA in a bacterium before and after the amplification of fadJ gene. Four activities of FadJ can be measured in accordance with, for example, the method of Binstock and Schulz (Binstock, J. F. and Schulz, H. 1981. Methods Enzymol. 71 (Pt C): 403-411).

The measurement of enoyl-CoA hydratase activity can be carried out by preparing a crude enzyme extract solution from cells collected after culturing, adding the extract solution to a reaction solution containing crotonyl CoA, and measuring absorbance at 263 nm for the amount of hydrated crotonyl CoA.

The enoyl-CoA hydratase activity is, for example, expressed with the amount of hydration of crotonyl CoA (nM) per minute per protein of the crude enzyme extract solution.

In addition, the measurement of 3-hydroxyacyl-CoA dehydrogenase activity can be carried out by preparing a crude enzyme extract solution from cells collected after culturing, adding the extract solution to a reaction solution containing acetoacetyl CoA and NADH, and measuring absorbance at 340 nm for the amount of dehydrogenated NADH.

The 3-hydroxyacyl-CoA dehydrogenase activity is expressed with the amount of oxidation of NADH (nM) per minute per protein of the crude enzyme extract solution.

It is desirable that the FadJ activity increases 1.5 folds or more, 2 folds or more, or 3 folds or more, as compared with a parent or unmodified strain. Expression of the protein can be confirmed by a method such as Western blotting. Also, by Northern hybridization, RT-PCR or the like, an increase in the amount of mRNA of fadJ gene can be confirmed.

A specific example of a gene encoding FadJ includes a gene located as fadJ gene of *Escherichia coli* at nucleotide 2457181 to nucleotide 2455037 (complementary strand) of *Escherichia coli* genomic sequence (GenBank Accession No.

U00096) and having the nucleotide sequence shown in SEQ ID NO: 37. SEQ ID NO: 38 shows the amino acid sequence encoded by the above gene.

The term "fadI gene" can mean a gene having homology with fadA gene and encoding an enzyme which is the β component of a fatty acid oxidation complex functioning under anaerobic conditions and aerobic conditions (Campbell, J. W. et al. 2003. Mol. Microbiol. 47(3): 793-805), and catalyzes a 3-ketoacyl-CoA thiolase activity (Pramanik, A. et al. 1979. J. Bacteriol. 137: 469-473).

3-ketoacyl-CoA thiolase dehydrogenase activity can refer to an activity to catalyze the following reaction (EC 2.3.1.16).

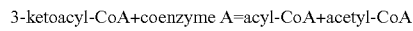

3-ketoacyl-CoA+coenzyme A=acyl-CoA+acetyl-CoA

An increase in the FadI activity by increasing expression of fadI gene can be confirmed, for example, by comparing thiolase activity of acetoacetyl CoA in a bacterium before and after the amplification of fadI gene. The FadI activity can be measured in accordance with, for example, the method of Binstock and Schulz (Binstock, J. F. and Schulz, H. 1981. Methods Enzymol. 71 (Pt C): 403-411).

The measurement of 3-ketoacyl-CoA thiolase activity can be carried out by preparing a crude enzyme extract solution from cells collected after culturing, adding the extract solution to a reaction solution containing acetoacetyl CoA, magnesium and CoA, and measuring absorbance at 303 nm for the amount of decrease in a complex of magnesium ion and enol acid, which is a substrate. The 3-ketoacyl-CoA thiolase activity is expressed with the amount of decrease in acetoacetyl CoA (nM) per minute per protein of the crude enzyme extract solution. It is desirable that the FadI activity increases 1.5 folds or more, 2 folds or more, or 3 folds or more, as compared with a parent or unmodified strain. Expression of the protein can be confirmed by a method such as Western blotting. Also, by Northern hybridization, RT-PCR or the like, an increase in the amount of mRNA of fadI gene can be confirmed.

A specific example of a gene encoding FadI includes a gene located as fadI gene of *Escherichia coli* at nucleotide 2458491 to nucleotide 2457181 (complementary strand) of *Escherichia coli* genomic sequence (GenBank Accession No. U00096) and having the nucleotide sequence shown in SEQ ID NO: 39. SEQ ID NO: 40 shows the amino acid sequence encoded by the above gene.

FadJ and FadI form a complex in a fatty acid oxidation complex found in the Enterobacteriaceae family and the genes thereof form fadIJ operon (Yang, S. Y. et al. 1990. J. Biol. Chem. 265: 10424-10429). Thus, as fadIJ operon, the whole operon can be amplified.

As for the fadR, fadL, fadE, fadD, fadB, fadA, cyoA, cyoB, cyoC, cyoD, cyoE, fadJ, and fadI genes, as long as the activities, that is, the functions of the encoded proteins are not impaired, homologous genes thereof having conservative mutations such as artificial mutants can be used. Thus, one encoding a conservative variant having the same amino acid sequence as the amino acid sequence of a known protein or the amino acid sequence of a wild-type protein (SEQ ID NO: 2, 4, 6, 8, 10, 12, 14, 16, 18, 20, 22, 38 or 40) except that one or several amino acids are substituted, deleted, inserted or added at one or several positions can be used. The term "one or several," although it varies depending on positions of amino acid residues in the spatial structure of the protein and types thereof, can refer to 1 to 20 residues, 1 to 10 residues, or 1 to 5 residues.

As long as the function of each of the proteins is maintained, these variants can have an identity of not less than 80%, not less than 90%, not less than 95%, and not less than 98% to the amino acid sequences shown in SEQ ID NO: 2, 4, 6, 8, 10, 12, 14, 16, 18, 20, 22, 38 or 40.

A representative example of the above-described conservative mutation is conservative substitution. The term, "conservative substitution" can mean a mutation of mutual substitution among Phe Trp and Tyr in the case of aromatic amino acids; among Leu, Ile and Val in the case of hydrophobic amino acids; among Gln and Asn in the case of polar amino acids; among Lys, Arg and His in the case of basic amino acids; among Asp and Glu in the case of acidic amino acids; and among Ser and Thr in the case of amino acids having a hydroxyl group.

More specific examples include replacement of Ala with Ser or Thr; replacement of Arg with Gln, His or Lys; replacement of Asn with Glu, Gln, Lys, His or Asp; replacement of Asp with Asn, Glu or Gln; replacement of Cys with Ser or Ala; replacement of Gln with Asn, Glu, Lys, His, Asp or Arg; replacement of Glu with Gly, Asn, Gln, Lys or Asp; replacement of Gly with Pro; replacement of His with Asn, Lys, Gln, Arg or Tyr; replacement of Ile with Leu, Met, Val or Phe; replacement of Leu with Ile, Met, Val or Phe; replacement of Lys with Asn, Glu, Gln, His or Arg; replacement of Met with Ile, Leu, Val or Phe; replacement of Phe with Trp, Tyr, Met, Ile or Leu; replacement of Ser with Thr or Ala; replacement of Thr with Ser or Ala; replacement of Trp with Phe or Tyr; replacement of Tyr with His, Phe or Trp; and replacement of Val with Met, Ile or Leu. Also, the above-described amino acid substitution, deletion, insertion, addition, inversion, or the like, includes a naturally-occurring mutation (mutant or variant) based on individual difference or species difference of microorganisms having the gene.

Also, genes where codons are with codons frequently used in a host can be used. Similarly, as long as they have functions, the N terminal side and/or C terminal side of the proteins encoded by genes can be extended or deleted. For example, the length of the extension is not more than 50 amino acid residues, not more than 20 amino acid residues, not more than 10 amino acid residues, or not more than 5 amino acid residues.

A gene encoding the above-described conservative variant is obtained, for example, by modifying a nucleotide sequence by site-specific mutagenesis such that an amino acid residue in a specific site of an encoded protein contains substitution, deletion, insertion or addition. Also, it can be obtained by a conventional mutation treatment. Examples of the mutation treatment include a method wherein a gene is treated in vitro with hydroxylamine or the like and a method wherein a microorganism having the gene, for example, a bacterium belonging to the genus of *Escherichia*, is treated by ultra violet ray, or by a mutagenesis agent used for a usual mutation treatment such as N-methyl-N'-nitro-N-nitrosoguanidine (NTG) or ethyl methanesulfonate (EMS). Also, the above-described amino acid substitution, deletion, insertion, addition, inversion or the like includes one caused by a naturally-occurring mutation (mutant or variant) based on individual difference or species difference of microorganisms having the gene. Whether these genes encode FadL, FadE, FadD, FadB, FadA or a cytochrome bo terminal oxidase complex can be checked, for example, by introducing these genes in a microorganism and measuring activity of each of the proteins.

The gene can be DNA having the above-described nucleotide sequence (SEQ ID NO: 1, 3, 5, 7, 9, 11, 13, 15, 17, 19, 21, 37 or 39), or hybridizing with a probe which can be prepared from DNA having such a nucleotide sequence under stringent conditions, and encoding FadL, FadE, FadD, FadB, FadA, FadJ, FadI or a cytochrome bo terminal oxidase complex.

The term, "stringent conditions" herein can refer to conditions under which the so-called specific hybrids form, and non-specific hybrids do not form. It is difficult to clearly express these conditions in values. For example, stringent conditions include conditions under which DNAs having high homology, for instance, DNAs having a homology of 80%, not less than 90%, and not less than 95%, hybridize to each other, and DNAs having a homology of less than that do not hybridize to each other. Alternatively, the stringent conditions are exemplified by conditions where washing is carried out once, 2-3 times at a salt concentration and temperature corresponding to ordinary conditions of washing in Southern hybridization, i.e. 60° C., 1×SSC, 0.1% SDS, 0.1× SSC, 0.1% SDS, or 68° C., 0.1×SSC, 0.1% SDS. "Homology" can also refer to "identity."

A probe can also be one having a sequence of a part of the gene. Such a probe can be prepared by a PCR reaction, using oligonucleotides prepared based on the nucleotide sequence of each gene as primers and a DNA fragment containing each gene as a template by a method known to those skilled in the art. In the case of using a DNA fragment of a length of about 300 bp as the probe, an example of condition for washing after the hybridization under the above-described conditions includes 50° C., 2×SSC, 0.1% SDS.

The above description on the conservative variant is also applied to the enzymes and genes described above about "Imparting L-amino acid-producing ability".

The above-described modification to increase expression of a gene can be carried out as the same manner as a method for increasing expression of the gene of interest described above about "Imparting L-amino acid-producing ability". The genes can be obtained by a PCR method using the chromosomal DNA of a microorganism having those as a template.

For instance, fadL gene of *Escherichia coli* can be obtained by PCR (polymerase chain reaction) method (see White, T. J. et al. 1989. Trends Genet. 5: 185-189) using primers prepared based on the nucleotide sequence shown in SEQ ID NO: 3, for example, primers shown in SEQ ID NOs: 25 and 26 with the chromosomal DNA of *Escherichia coli* as a template.

The fadD gene of *Escherichia coli* can be obtained by PCR using primers prepared based on the nucleotide sequence shown in SEQ ID NO: 5, for example, primers shown in SEQ ID NOs: 27 and 28 with the chromosomal DNA of *Escherichia coli* as a template.

The fadE gene of *Escherichia coli* can be obtained by PCR using primers prepared based on the nucleotide sequence shown in SEQ ID NO: 7, for example, primers shown in SEQ ID NOs: 29 and 30 with the chromosomal DNA of *Escherichia coli* as a template.

The fadB gene of *Escherichia coli* can be obtained by PCR using primers prepared based on the nucleotide sequence shown in SEQ ID NO: 9, for example, primers shown in SEQ ID NOs: 31 and 32 with the chromosomal DNA of *Escherichia coli* as a template.

The fadA gene of *Escherichia coli* can be obtained by PCR using primers prepared based on the nucleotide sequence shown in SEQ ID NO: 11, for example, primers shown in SEQ ID NOs: 33 and 34 with the chromosomal DNA of *Escherichia coli* as a template.

The fadBA operon of *Escherichia coli* can be obtained by PCR using primers prepared based on the nucleotide sequence shown in SEQ ID NOs: 9 and 11, for example, primers shown in SEQ ID NOs: 35 and 36 with the chromosomal DNA of *Escherichia coli* as a template.

The cyoABCDE gene of *Escherichia coli* can be obtained by PCR using primers prepared based on the nucleotide sequence shown in SEQ ID NOs: 13 and 21, for example, primers shown in SEQ ID NOs: 37 and 38 with the chromosomal DNA of *Escherichia coli* as a template.

The fadIJ operon of *Escherichia coli* can be obtained by PCR using primers prepared based on the nucleotide sequence shown in SEQ ID NOs: 37 and 39, for example, primers shown in SEQ ID NOs: 41 and 42 with the chromosomal DNA of *Escherichia coli* as a template.

Genes derived from other microorganisms can also be obtained from the chromosomal DNA or a chromosomal DNA library of such microorganisms by a PCR method using, as primers, oligonucleotides prepared based on sequence information on each of the above-described genes or sequence information on known genes or proteins in the microorganisms; or a hybridization method using, as probes, oligonucleotides prepared based on the above-described sequence information. The chromosomal DNA can be prepared from the microorganism which is a DNA donor by, for example, the method of Saito and Miura (see Saito, H. and Miura, K. I. 1963. Biochem. Biophys. Acta, 72, 619-629; Methods in Biotechnology Experiments or Seibutsu Kogaku Jikkan-sho, edited by The Society of Biotechnology, Japan, p 97-98, BAIFUKAN CO., LTD, 1992) or the like.

An increase in expression of genes (fadL, fadE, fadD, fadB, fadA, cyoA, cyoB, cyoC, cyoD, cyoE, fadJ and fadI) and genes in an L-amino acid synthesis system can be achieved using the methods described above by increasing the copy number of the genes or modifying an expression regulatory sequence of the genes by transformation and homologous recombination. The increase in the expression of the genes can also be achieved by amplifying an activator to increase the expression of the genes and/or by deleting or attenuating a regulator to decrease the expression of the genes.

The methods for increasing the expression of the genes will be described below.

The first method is a method for increasing the copy number of a gene of interest. For example, the copy number of the gene can be increased by cloning the gene of interest into an appropriate vector and transforming a host bacterium using the obtained vector.

Examples of the vector to be used for transformation include plasmids capable of autonomously replicating in microorganisms to be used. Examples of the plasmids capable of autonomously replicating in microorganism belonging to the Enterobacteriaceae family include pUC19, pUC18, pBR322, RSF1010, pHSG299, pHSG298, pHSG399, pHSG398, pSTV28, pSTV29 (pHSG and pSTV plasmids are available from Takara Bio Inc.), pMW 119, pMW 118, pMW219, pMW218 (pMW plasmids are available from Nippon Gene Co., Ltd.) and the like. Instead of the plasmids, phage DNAs can be used as vectors.

Examples of methods for transformation include a method wherein recipient bacterial cells are treated with calcium chloride to increase permeability for DNA as reported with regard to *Escherichia coli* K-12 (Mandel, M. and Higa, A. J. Mol. Biol. 1970, 53: 159-162), a method wherein competent cells are prepared from cells at the growth phase to introduce DNA as reported with regard to *Bacillus subtilis* (Duncan, C. H., Wilson, G. A. and Young, F. E. 1997. Gene 1: 153-167) and the like. Alternatively, as known with regard to *Bacillus subtilis*, actinomycetes and yeast, a method wherein cells of DNA recipient bacteria are made into protoplast or spheroplast, either of which is capable of readily taking up recombinant DNA, and then the recombinant DNA is introduced in the DNA recipient bacteria (Chang, S, and Choen, S. N. 1979. Mol. Gen. Genet. 168: 111-115; Bibb, M. J., Ward, J. M. and Hopwood, 0. A. 1978. Nature 274: 398-400; Hinnen, A., Hicks, J. B. and Fink, G. R. 1978. Proc. Natl. Acad. Sci. USA 75: 1929-1933) can also be applied. The transformation of microorganisms can be carried out by an electric pulse method (Japanese Laid-Open Patent Application No. 2-207791).

To increase the copy number of a gene can be achieved by introducing multiple copies of a gene of interest on the chromosomal DNA of a microorganism. Introduction of multiple copies of a gene on the chromosomal DNA of the microorganism can be carried out by a homologous recombination method using a sequence existing at multiple copies on the chromosomal DNA as a target (MillerI, J. H. Experiments in Molecular Genetics, 1972, Cold Spring Harbor Laboratory). As the sequence existing as multiple copies on the chromosomal DNA, repetitive DNA and inverted repeat existing at the end of a transposon can be used. Or, as disclosed in Japanese Laid-Open Patent Application No. 2-109985, it is possible to introduce multiple copies on the chromosomal DNA by introducing the gene of interest on the transposon and transferring it. Further, the gene of interest can be incorporated in the chromosome of a host by a method using Mu phages (Japanese Laid-Open Patent Application No. 2-109985). Confirmation of the transfer of the gene of interest on the chromosome can be made by Southern hybridization using a part of the gene as a probe.

In the case of increasing the copy number of a gene, as long as the activity of a product of the gene of interest can be enhanced, the copy number is not particularly limited. When a microorganism endogenously has the gene of interest, it can be 2 or more. Also, when the microorganism does not endogenously have the gene, the copy number of a gene to be introduced can be 1, or can be 2 or more.

The second method is a method for increasing expression of a gene of interest by replacing an expression regulatory sequence such as a promoter of the gene of interest with one having appropriate strength on the chromosomal DNA or on a plasmid. For example, thr promoter, lac promoter, trp promoter, trc promoter, pL promoter, tac promoter and the like are known as promoters which are often used. A method for evaluating the strength of the promoter and examples of strong promoters are described in a paper of Goldstein and Doi (Goldstein, M. A. and Doi R. H. 1995. Prokaryotic promoters in biotechnology. Biotechnol. Annu. Rev., 1, 105-128) and the like.

As disclosed in WO00/18935, it is possible to introduce replacement of several nucleotides in a promoter region of a gene so that the promoter has appropriate strength. The replacement of an expression regulatory sequence can be carried out, for example, in the same manner as gene replacement using a temperature-sensitive plasmid. Examples of vectors that can be used in *Escherichia coli* and *Pantoea ananatis* and have origin of temperature-sensitive replication include temperature-sensitive plasmid pMAN997 described in WO99/03988 and derivatives thereof. In addition, by a method using linear DNA such as a method called "Red-driven integration" using Red recombinase of λ phage (Datsenko, K. A. and Wanner, B. L., 2000. Proc. Natl. Acad. Sci. USA. 97: 6640-6645), a method combining the Red-driven integration method with an excision system derived from λ phage (Cho, E. H., Gumport, R. I., and Gardner, J. F. 2002. J. Bacteriol. 184: 5200-5203) (see WO2005/010175) or the like, the replacement of the expression regulatory sequence can be carried out. The modification of the expression regulatory sequence can be combined with the method for increasing the copy number of the gene described above.

The replacement of several nucleotides in a spacer between a ribosome-binding site (RBS) and the initiation codon, particularly in a sequence immediately upstream of the initiation codon significantly affects efficiency of translation of mRNA. And, it is possible to increase an amount of the translation by modifying those.

As for cyo operon (cyoABCDE) encoding cytochrome bo terminal oxidase, expression of a gene encoding each subunit can be independently increased or can be simultaneously increased as a polycistron. Also, when the gene is introduced in a microorganism using a vector, genes encoding each of the subunits can be simultaneously carried on a single vector molecule or can be separately carried on different vector molecules. Additionally, when the gene is incorporated in the chromosome, the genes encoding each subunit can be simultaneously inserted in the same site or can be separately inserted in different sites.

EXAMPLES

The present invention will now be more specifically described by way of the following non-limiting examples. In the examples, as a representative fatty acid, the sodium salt of oleic acid ($C_{17}H_{33}COOH$) (manufactured by NACALAI TESQUE, INC.) was used.

Example 1

Construction of *Escherichia coli* L-Lysine-Producing Bacterium in which fadR was Deleted <1-1> Construction of fadR Gene-Deleted Strain A transcriptional factor FadR which regulates fatty acid metabolism in *Escherichia coli* is encoded by the fadR gene (SEQ ID NO: 1) (DiRusso, C. C. et al. 1992. J. Biol. Chem. 267: 8685-8691). As a parent strain for this gene disruption, WC196 Δ cadA Δ ldcC strain (AJ110692: FERM BP-11027) described as an L-lysine-producing strain of *Escherichia coli* in WO2006/078039 was used. This strain is a strain in which cadA gene and ldcC gene are disrupted in WC1-96 strain (FERM BP-5252). AJ110692 strain has been deposited at International Patent Organism Depositary, National Institute of Advanced Industrial Science and Technology, (AIST Tsukuba Central 6, 1-1-1 Higashi, Tsukuba, Ibaraki, Japan) as international deposition in accordance with the Budapest Treaty on Oct. 7, 2008 under an accession number FERM BP-11027.

Deletion of fadR gene encoding a transcriptional factor which regulates fatty acid metabolism was carried out by a method called "Red-driven integration" originally developed by Datsenko and Wanner (Datsenko, K. A. and Wanner, B. L. 2000. Proc. Natl. Acad. Sci. USA. 97: 6640-6645) and an excision system derived from a λ phage (Cho, E. H., Gumport, R. I., and Gardner, J. F. 2002. J. Bacteriol. 184: 5200-5203). According to "Red-driven integration", using a PCR product obtained by using a synthetic oligonucleotide having a part of a gene of interest in the 5' side and a synthetic oligonucleotide in which part of antibiotic resistance gene is designed in the 3' side as primers, a gene disruption strain can be constructed in one step. Further, by combining the excision system derived from A phage therewith, the antibiotic resistance gene incorporated in the gene disruption strain can be removed (Japanese Patent Application Laid-Open Publication No. 2005-058227).

As a template for PCR, plasmid pMW118-attL-kan-attR (Japanese Patent Application Laid-Open Publication No. 2005-058227) was used. pMW118-attL-kan-attR is a plasmid obtained by inserting attachment sites of the λ phage, attL and attR genes, and an antibiotic resistance gene, kan gene into pMW118 (manufactured by Takara Bio Inc.) in the order of attL-kan-attR.

PCR was carried out using synthetic oligonucleotides shown in SEQ ID NOs: 23 and 24 as primers, which synthetic oligonucleotides have a sequence corresponding to both ends of attL and attR at the 3' terminus thereof and a sequence corresponding to a part of fadR, which is the gene of interest, at the 5' terminus thereof.

The amplified PCR product was purified by agarose gel and introduced in to *Escherichia coli* AJ110692 strain containing plasmid pKD46 having a temperature-sensitive replication ability by electroporation. Plasmid pKD46 (Datsenko, K. A. and Wanner, B. L. 2000. Proc. Natl. Acad. Sci. USA. 97: 6640-6645) contains a DNA fragment of λ phage with a total of 2154 nucleotides (GenBank/EMBL accession number J02459, 31088th to 33241st) containing genes (γ, β and exo genes) encoding Red recombinase in a λ Red homologous recombination system controlled by an arabinose-inducible ParaB promoter. Plasmid pKD46 is necessary for incorporation of the PCR product into the chromosome of AJ110692 strain.

Competent cells for electroporation were prepared as follows. That is, *Escherichia coli* WC196 strain cultured in an LB medium (tryptone 10 g/L, Yeast extract 5 g/L, NaCl 10 g/L) containing 100 mg/L ampicillin at 30° C. overnight were 100-fold diluted with 5 mL of LB medium containing ampicillin (100 mg/L) and L-arabinose (10 mM). The obtained dilution was allowed to grow at 30° C. under aeration until OD600 reached about 0.6 and thereafter 100-fold concentrated. And, the resultant was washed three times with 10% glycerol so as to be used for the electroporation. The electroporation was carried out using 70 μL of competent cells and about 100 ng of the PCR product. Cells after electroporation were added with 1 mL of an SOC medium (Sambrook, J. and Russell, D. W. 2001. Molecular Cloning A Laboratory Manual/Third Edition. Cold Spring Harbor Laboratory Press, New York) and cultured at 37° C. for 1 hour. Thereafter, the cells were subjected to plate culture at 37° C. on an LB agar medium (tryptone 10 g/L, Yeast extract 5 g/L, NaCl 10 g/L, agar 15 g/L) containing Km (kanamycin) (40 mg/L) to select a Km resistant recombinant. Next, in order to cure pKD46 plasmid, the recombinant was subcultured twice on the LB agar medium containing Km at 42° C. The resistance to ampicillin of the obtained colony was examined to obtain an ampicillin-sensitive strain in which pKD46 was cured.

Deletion of fadR gene in the mutant, which was distinguishable by kanamycin resistance gene was confirmed by PCR. The obtained fadR-deleted strain was named AJ110692 Δ fadR::att-kan strain.

Next, in order to cure an att-kan gene inserted in fadR gene, the above-described helper plasmid, pMW-intxis-ts (Japanese Patent Application Laid-Open Publication No. 2005-058227) was used. pMW-intxis-ts is a plasmid carrying a gene encoding integrase (Int) of λ phage and gene encoding excisionase (Xis) of λ phage, and having temperature-sensitive replication ability.

Competent cells of AJ110692 Δ fadR::att-kan strain were prepared in accordance with a conventional method and transformed with a helper plasmid pMW-intxis-ts. The resultant was subjected to plate culture at 30° C. on an LB agar medium containing 100 mg/L ampicillin to select an ampicillin-resistant strain.

Next, in order to cure pMW-intxis-ts plasmid, the strain was subcultured twice on an LB agar medium at 42° C. The resistance to ampicillin and resistance to kanamycin of the obtained colony were examined to obtain a kanamycin, ampicillin-sensitive strain where a fadR is disrupted and att-kan and pMW-intxis-ts was dropped. This strain was named AJ110692 Δ fadR strain.

<1-2> Introduction of Plasmid for Producing Lysine into AJ110692 Δ fadR Strain

AJ110692 Δ fadR strain was transformed with plasmid pCABD2 (WO95/16042) for lysine production which carries dapA, dapB, lysC and ddh genes in accordance with a conventional method, thereby obtaining AJ110692 Δ fadR/pCABD2 strain.

The strain prepared above was cultured in an LB medium containing 25 mg/L streptomycin at 37° C. until OD600 reached about 0.6. Thereafter, an amount of 40% glycerol solution equal to the culture solution was added therein and stirred. The resultant was aliquoted in an appropriate amount and stored at −80° C. to provide a glycerol stock.

Example 2

Culture of L-Lysine-Producing Strain in which fadR was Deleted

Glycerol stocks of AJ110692 Δ fadR/pCABD2 strain and a control strain AJ110692/pCABD2 strain were thawed. And, 100 μL of each was evenly spread on an LB agar medium plate containing 25 mg/L streptomycin and incubated at 37° C. for 24 hours. About ⅛ amount of bacterial cells on the plate were inoculated into 20 mL of fermentation medium described below containing 25 mg/L streptomycin in a 500 mL-Sakaguchi flack, and cultured using a reciprocal shaking culture apparatus at 37° C. for 48 hours. As a carbon source in a main culture, glucose or sodium oleate was used. For sodium oleate, one in which polyoxyethylene sorbitan monooleic acid ester (Tween 80: manufactured by NACALAI TESQUE, INC.) was added as an emulsification promoter to a final concentration of 0.5% (w/v) was used. As for the total amount of carbon sources, glucose was 40 g/L and sodium oleate was 20 g/L. It was separately confirmed that these strain were unable to use Tween 80. The medium composition used for the culture is shown below.

L-Lysine Production Medium for Bacteria Belonging to the Genus *Escherichia*

| Carbon source | |
|---|---|
| Glucose | 40 g/L |
| or | |
| Sodium oleate | 20 g/L |
| Tween 80 | 5 g/L |
| Other ingredients | |
| $(NH_4)_2SO_4$ | 24 g/L |
| $KH_2PO_4$ | 1 g/L |
| $MgSO_4 \cdot 7H_2O$ | 1 g/L |
| $FeSO_4 \cdot 7H_2O$ | 0.01 g/L |
| $MnSO_4 \cdot 7H_2O$ | 0.01 g/L |
| Yeast Extract | 2 g/L |
| $CaCO_3$ (Japanese Pharmacopoeia) | 30 g/L |

The medium was adjusted to a pH of 7.0 with KOH and autoclaved at 120° C. for 20 minutes. The carbon source and $MgSO_4 \cdot 7H_2O$ were separately sterilized and combined. $CaCO_3$ was subjected to dry heat sterilization and thereafter added.

48 hours later, the amount of L-lysine in the culture supernatant was measured by a biosensor BF-5 (Oji Scientific Instruments). The degree of growth was measured with turbidity (OD) in culture using glucose whereas, in cases where a fatty acid was used as a carbon source, viable cell count was measured by spreading an appropriately diluted culture solution on an LB plate. With regard to an average of the results of culture using two flasks each, the results of culture using glucose are shown in Table 1 and results of culture using sodium oleate are shown in Table 2.

When glucose was used as the carbon source, L-lysine production of fadR-disrupted strain (AJ110692 Δ fadR/pCABD2) was equal to or less than that of a parent strain (AJ110692/pCABD2). However, when sodium oleate was used as the carbon source, fadR disrupted strain (AJ110692 Δ fadR/pCABD2) exhibited significant improvement of growth and L-lysine production, compare with the parent strain (AJ110692/pCABD2).

TABLE 1

Results of culturing L-lysine-producing strain in which fadR was disrupted using glucose as a carbon source

| Strain | O.D. | L-lysine (g/L) |
| --- | --- | --- |
| AJ110692/pCABD2 | 16.7 | 14.8 |
| AJ110692 Δ fadR/pCABD2 | 17.4 | 14.3 |

TABLE 2

Results of culturing L-lysine-producing strain in which fadR was disrupted using sodium oleate as a carbon source

| Strain | Viable cell count ($10^8$/mL) | L-lysine (g/L) |
| --- | --- | --- |
| AJ110692/pCABD2 | 42.5 | 3.0 |
| AJ110692 ΔfadR/pCABD2 | 65.0 | 3.4 |

Example 3

Construction of L-Lysine-Producing Bacterium in which fad Genes were Amplified

<3-1> Construction of Strain in which fad Genes were Amplified

Enzymes in the beta oxidation pathway of a fatty acid are encoded by a group of genes composed of fadL (SEQ ID NO: 3), fadD (SEQ ID NO: 5), fadE (SEQ ID NO: 7), fadB (SEQ ID NO: 9) and fadA (SEQ ID NO: 11) (Clark, D. P. and Cronan Jr., J. E. 1996. p. 343-357. In F. D. Neidhardt (ed.), *Escherichia coli* and *Salmonella* Cellular and Molecular Biology/Second Edition, American Society for Microbiology Press, Washington, D.C). In addition, fadB and fadA form an operon fadBA. PCR was carried out, with the chromosomal DNA of wild type *Escherichia coli* W3110 strain as a template, to obtain fadL gene using primers shown in SEQ ID NOs: 25 and 26; fadD gene using primers shown in SEQ ID NOs: 27 and 28; fadE gene using primers shown in SEQ ID NOs: 29 and 30; fadB gene using primers shown in SEQ ID NOs: 31 and 32; fadA gene using primers shown in SEQ ID NOs: 33 and 34; and fadBA operon using primers shown in SEQ ID NOs: 35 and 36.

<3-2> Construction of Plasmid for Amplifying fadL Gene

PCR was carried out using a primer shown in SEQ ID NO: 25 having an EcoRI site and a primer shown in SEQ ID NO: 26 having a Hind III site with the chromosomal DNA of W3110 strain as a template, thereby obtaining a PCR product containing fadL gene. A purified PCR product was digested with restriction enzymes EcoRI and Hind III, thereby obtaining a gene fragment containing fadL gene. A purified fadL gene fragment was ligated to pTWV228 vector (manufactured by Takara Bio Inc.) digested with EcoRI and Hind III, thereby constructing plasmid pTWV-fadL for amplifying fadL gene.

<3-3> Construction of Plasmid for Amplifying fadD Gene

PCR was carried out using a primer shown in SEQ ID NO: 27 having an EcoRI site and a primer shown in SEQ ID NO: 28 having a Hind III site with the chromosomal DNA of W3110 strain as a template, thereby obtaining a PCR product containing fadD gene. A purified PCR product was digested with restriction enzymes EcoRI and Hind III, thereby obtaining a gene fragment containing fadD gene. A purified fadD gene fragment was ligated to pTWV228 vector (manufactured by Takara Bio Inc.) digested with EcoRI and Hind III, thereby constructing plasmid pTWV-fadD for amplifying fadD gene.

<3-4> Construction of Plasmid for Amplifying fadE Gene

PCR was carried out using a primer shown in SEQ ID NO: 29 having an EcoRI site and a primer shown in SEQ ID NO: 30 having a Hind III site with the chromosomal DNA of W3110 strain as a template, thereby obtaining a PCR product containing fadE gene. A purified PCR product was digested with restriction enzymes EcoRI and Hind III, thereby obtaining a gene fragment containing fadE gene. A purified fadE gene fragment was ligated to pTWV228 vector (manufactured by Takara Bio Inc.) digested with EcoRI and Hind III, thereby constructing plasmid pTWV fadE for amplifying fadE gene.

<3-5> Construction of Plasmid for Amplifying fadB Gene

PCR was carried out using a primer shown in SEQ ID NO: 31 having an EcoRI site and a primer shown in SEQ ID NO: 32 having a Hind III site with the chromosomal DNA of W3110 strain as a template, thereby obtaining a PCR product containing fadB gene. A purified PCR product was digested with restriction enzymes EcoRI and Hind III, thereby obtaining a gene fragment containing fadB gene. A purified fadB gene fragment was ligated to pTWV228 vector (manufactured by Takara Bio Inc.) digested with EcoRI and Hind III, thereby constructing plasmid pTWV-fadB for amplifying fadB gene.

<3-6> Construction of Plasmid for Amplifying fadA Gene

As described above, PCR was carried out using primers shown in SEQ ID NO: 33 and SEQ ID NO: 34 with the chromosomal DNA of W3110 strain as a template, thereby obtaining a PCR product containing fadA gene. A purified PCR product was ligated to a plasmid fragment obtained by digesting vector pTWV228 (manufactured by Takara Bio Inc.) with SalI and purifying the resultant using In-Fusion Dry-Down PCR Cloning Kit (manufactured by Clontech), thereby constructing plasmid pTWV-fadA for amplifying fadA gene.

<3-7> Construction of Plasmid for Amplifying fadBA Operon

PCR was carried out using a primer shown in SEQ ID NO: 35 having an EcoRI site and a primer shown in SEQ ID NO: 36 having a Hind III site with the chromosomal DNA of W3110 strain as a template, thereby obtaining a PCR product containing fadBA operon. A purified PCR product was digested with restriction enzymes EcoRI and Hind III, thereby obtaining a gene fragment containing fadBA operon.

A purified fadBA operon fragment was ligated to pTWV228 vector (manufactured by Takara Bio Inc.) digested with EcoRI and Hind III, thereby constructing plasmid pTWV-fadBA for amplifying fadBA operon.

<3-8> Introduction of Plasmid for Lysine Production into AJ110692 Strain

As an L-lysine-producing strain of *Escherichia coli*, the above-described AJ110692/pCABD2 strain was used. AJ110692 strain was transformed with plasmids pTWV-fadL, pTWV fadD, pTWV-fadE, pTWV-fadB, pTWV-fadA and pTWV fadBA, which respectively carry the corresponding gene of a group of fad genes prepared in the previous section, as well as a control vector pTWV228 in accordance with a conventional method, thereby obtaining AJ110692/pCABD2/pTWV-fadL, AJ110692/pCABD2/pTWV-fadD, AJ110692/pCABD2/pTWV-fadE, AJ110692/pCABD2/pTWV-fadB, AJ110692/pCABD2/pTWV-fadA and AJ110692/pCABD2/pTWV-fadBA, as well as AJ110692/pCABD2/pTWV228 strain, respectively.

The strain prepared above was cultured in an LB medium containing 50 mg/L ampicillin and 20 mg/L streptomycin at 37° C. until OD600 reached about 0.6. Thereafter, an amount of 40% glycerol solution equal to the culture solution was added therein and stirred. The resultant was aliquoted in an appropriate amount and stored at −80° C. to provide a glycerol stock.

Example 4

Culture of L-Lysine-Producing Strain in which fad Genes were Amplified

Glycerol stocks of the strains obtained in Example 3, in which fad genes were amplified, were thawed. And, 100 μL of each was evenly spread on an LB agar medium plate containing 50 mg/L ampicillin and 20 mg/L streptomycin and incubated at 37° C. for 24 hours. About ½ volume of bacterial cells on the obtained plate were inoculated into 5 mL of fermentation medium described below containing 50 mg/L ampicillin and 20 mg/L streptomycin in a test tube manufactured by AGC TECHNO GLASS CO., LTD. (diameter×length×thickness (mm)=25×200×1.2), and cultured using a reciprocal shaking culture apparatus at 37° C. for 72 hours. As a carbon source in a main culture, sodium oleate added with polyoxyethylene sorbitan monooleic acid ester (Tween 80: manufactured by NACALAI TESQUE, INC.) as an emulsification promoter to a final concentration of 0.5% (w/v) was used. As for a total amount of carbon sources, sodium oleate was 10 g/L. The medium composition used for the culture is shown below.

L-Lysine Production Medium for Bacteria Belonging to the Genus *Escherichia*

| Carbon source | |
| --- | --- |
| Sodium oleate | 10 g/L |
| Tween 80 | 5 g/L |
| Other ingredients | |
| $(NH_4)_2SO_4$ | 24 g/L |
| $KH_2PO_4$ | 1 g/L |
| $MgSO_4 \cdot 7H_2O$ | 1 g/L |
| $FeSO_4 \cdot 7H_2O$ | 0.01 g/L |
| $MnSO_4 \cdot 7H_2O$ | 0.01 g/L |

-continued

| Yeast Extract | 2 g/L |
| --- | --- |
| PIPES (pH 7.5) | 20 g/L |

The medium was adjusted to pH of 7.5 with KOH and autoclaved at 115° C. for 10 minutes. The carbon source, $MgSO_4 \cdot 7H_2O$, and PIPES were separately sterilized and combined.

72 hours later, the amount of L-lysine in the culture supernatant was measured by Biotech analyzer AS210 (Sakura Seiki). In this medium, the degree of growth was measured with turbidity (OD) by combining a culture solution with an equal amount of 10% Tween 80 solution. The culture was carried out using three flasks for each and the average value of the results thereof is shown in Table 3.

Compared with a control strain in which vector pTWV228 was introduced, the strain in which fadL, fadD, fadE, fadB, fadA or fadBA gene was introduced exhibited significantly higher L-lysine production.

TABLE 3

Results of culturing L-lysine-producing strain in which each of fad genes was amplified

| Strain | O.D. | L-lysine (g/L) |
| --- | --- | --- |
| AJ110692/pCABD2/pTWV228 | 8.5 | 3.2 |
| AJ110692/pCABD2/pTWV-fadL | 7.7 | 4.7 |
| AJ110692/pCABD2/pTWV-fadD | 10 | 4.6 |
| AJ110692/pCABD2/pTWV-fadE | 8.2 | 5.0 |
| AJ110692/pCABD2/pTWV-fadB | 11.3 | 3.9 |
| AJ110692/pCABD2/pTWV-fadA | 9.7 | 3.9 |
| AJ110692/pCABD2/pTWV-fadBA | 9.5 | 4.3 |

Example 5

Culture of L-Threonine-Producing Bacteria in which Fad Genes were Amplified

As an L-threonine-producing bacterium, *Escherichia coli* VKPM B-5318 strain described in EP 0593792 was used.

B-5318 strain was transformed with plasmids pTWV-fadL, pTWV-fadD and pTWV-fadE, all of which carry the corresponding gene of a group of fad genes prepared in EXAMPLES <3-1>, as well as a control vector pTWV228 in accordance with a conventional method, thereby obtaining B-5318/pTWV-fadL, B-5318/pTWV-fadD and B-5318/pTWV-fadE as well as B-5318/pTWV228, respectively.

The strain prepared above was cultured in an LB medium containing 50 mg/L ampicillin and 25 mg/L streptomycin at 37° C. until OD600 reached about 0.6. Thereafter, an equal amount of 40% glycerol solution was added to the culture solution and stirred. The resultant was aliquoted in an appropriate amount and stored at −80° C. to provide a glycerol stock.

Example 6

Culture of L-Threonine-Producing Strains in which fad Genes were Amplified

Glycerol stocks of B-5318/pTWV-fadL strain, B-5318/pTWV-fadD strain, B-5318/pTWV-fadE strain and B-5318/pTWV228 strain were thawed. And, 100 μL of each was evenly spread on an LB agar medium plate containing 50 mg/L ampicillin and 25 mg/L streptomycin and incubated at 37° C. for 24 hours. About ¼ volume of bacterial cells on the obtained plate were inoculated into 40 mL of fermentation medium described below containing 50 mg/L ampicillin and 25 mg/L streptomycin in a 500 mL-Erlenmeyer flask equipped with baffles, and cultured using a reciprocal shaking culture apparatus at 40° C. for 48 hours. As a carbon source in a main culture, sodium oleate added with polyoxyethylene sorbitan monooleic acid ester (Tween 80: manufactured by NACALAI TESQUE, INC.) as an emulsification promoter to a final concentration of 0.5% (w/v) was used. As for a total amount of carbon source, sodium oleate was 10 g/L. The medium composition used for the culture is shown below.

L-Threonine Production Medium for Bacteria Belonging to the Genus *Escherichia*

| Carbon source | |
|---|---|
| Sodium oleate | 10 g/L |
| Tween 80 | 5 g/L |
| Other ingredients | |
| $(NH_4)_2SO_4$ | 16 g/L |
| $KH_2PO_4$ | 1 g/L |
| $MgSO_4 \cdot 7H_2O$ | 1 g/L |
| $FeSO_4 \cdot 7H_2O$ | 0.01 g/L |
| $MnSO_4 \cdot 7H_2O$ | 0.01 g/L |
| Yeast Extract | 2 g/L |
| PIPES (pH 7.0) | 20 g/L |

The medium was adjusted to a pH of 7.0 with KOH and autoclaved at 120° C. for 20 minutes. The carbon source, $MgSO_4 \cdot 7H_2O$, and PIPES were separately sterilized and combined.

48 hours later, the amount of L-threonine in the culture supernatant was measured by an amino acid analyzer (Amino Acid Analyzer L-8900 manufactured by Hitachi). In this medium, the degree of growth was measured with turbidity (OD) by combining a culture solution with an equal quantity of 10% Tween 80 solution. The culture was carried out using two flasks for each and the average value of the results thereof is shown in Table 4.

Compared with a control strain in which vector pTWV228 was introduced, L-threonine production in all of the strains in which fadL, fadD and fadE were introduced was improved.

TABLE 4

Results of culturing L-threonine-producing bacteria in which fad Genes were amplified

| Strain | O.D. | L-threonine (g/L) |
|---|---|---|
| B5318/pTWV228 | 3.7 | 3.6 |
| B5318/pTWV-fadL | 4.1 | 3.8 |
| B5318/pTWV-fadD | 4.3 | 3.8 |
| B5318/pTWV-fadE | 4.7 | 4.0 |

Example 7

Construction of a Strain in which cyoABCDE Operon was Introduced

For amplification of cyo operon (cyoABCDE) encoding a cytochrome bo terminal oxidase complex of *Escherichia coli*, plasmid pMW(CYO)B described in Japanese Patent Application Laid-Open Publication No. 2002-017363 was used. Similarly to Example 3, L-lysine-producing strain AJ110692/pCABD2 of *Escherichia coli* was transformed with plasmid pMW(CYO)B and a control vector pMW219, thereby obtaining AJ110692/pCABD2/pMW(CYO)B and AJ110692/pCABD2/pMW219, respectively.

Example 8

Culture of L-Lysine-Producing Strain in which cyoABCDE Operon was Amplified

Glycerol stocks of the strains prepared in of Example 7 were thawed. 100 μL of each was evenly spread on an LB agar medium plate containing 40 mg/L ampicillin and 25 mg/L streptomycin and incubated at 37° C. for 24 hours. About ¼ volume of bacterial cells on the plate were inoculated into 40 mL of fermentation medium described below containing 40 mg/L ampicillin and 25 mg/L streptomycin in a 500 mL-Erlenmeyer flask equipped with baffles, and cultured using a reciprocal shaking culture apparatus at 37° C. for 48 hours. As a carbon source in a main culture, sodium oleate added with polyoxyethylene sorbitan monooleic acid ester (Tween 80: manufactured by NACALAI TESQUE, INC.) as an emulsification promoter to a final concentration of 0.5% (w/v) was used. As for a total amount of carbon sources, sodium oleate was 10 g/L. The medium composition used for the culture is shown below.

L-Lysine Production Medium for Bacteria Belonging to the Genus of *Escherichia*

| Carbon source | |
|---|---|
| Sodium oleate | 10 g/L |
| Tween 80 | 5 g/L |
| Other ingredients | |
| $(NH_4)_2SO_4$ | 24 g/L |
| $KH_2PO_4$ | 1 g/L |
| $MgSO_4 \cdot 7H_2O$ | 1 g/L |
| $FeSO_4 \cdot 7H_2O$ | 0.01 g/L |
| $MnSO_4 \cdot 7H_2O$ | 0.01 g/L |
| Yeast Extract | 2 g/L |
| PIPES (pH 7.0) | 20 g/L |

The medium was adjusted to a pH of 7.0 with KOH and autoclaved at 120° C. for 20 minutes. The carbon source, $MgSO_4 \cdot 7H_2O$, and PIPES were separately sterilized and combined.

48 hours later, the amount of L-lysine in the culture supernatant was measured by Biotech analyzer AS210 (Sakura Seiki). In this medium, the degree of growth was measured with turbidity (OD) by combining a culture solution with an equal quantity of 10% Tween 80 solution. The culture was carried out using two flasks for each and the average value thereof is shown in Table 5. Compared with a control strain in which vector pMW219 was introduced, the strain in which cyoABCDE operon was introduced significantly exhibited L-lysine production.

TABLE 5

Results of culturing L-lysine-producing bacteria in which cyoABCDE operon was amplified

| Strain | O.D. | L-lysine (g/L) |
|---|---|---|
| AJ110692/pCABD2/pMW219 | 9.2 | 3.4 |
| AJ110692/pCABD2/pMW(CYO)B | 8.4 | 3.7 |

Example 9

Construction of L-Lysine-Producing Strain in which FadIJ Operon was Amplified <9-1> Construction of Strain in which FadIJ Operon was Amplified PCR was carried out using a primer shown in SEQ ID NO: 41 having an EcoRI site and a primer shown in SEQ ID NO: 42 having a Hind III site with the chromosomal DNA of W3110 strain as a template, thereby obtaining a PCR product containing fadIJ operon. A purified PCR product was digested with restriction enzymes EcoRI and Hind III, thereby obtaining a gene fragment containing fadIJ operon. A purified fadIJ operon fragment was ligated to pTWV228 vector (manufactured by Takara Bio Inc.) digested with EcoRI and Hind III, thereby constructing a plasmid pTWV-fadIJ for amplifying fadIJ operon.

Preparation of Strain in which FadIJ Operon was Introduced

Similarly to Example 3, L-lysine-producing strain AJ110692/pCABD2 of *Escherichia coli* was transformed with plasmid pTWV-fadIJ and a control vector pTWV228, thereby obtaining AJ110692/pCABD2/pTWV-fadIJ and AJ110692/pCABD2/pTWV228, respectively.

The strain prepared above was cultured in an LB medium containing 50 mg/L ampicillin and 25 mg/L streptomycin at 37° C. until OD600 reached about 0.6. Thereafter, an equal amount of 40% glycerol solution was added to the culture solution and stirred. The resultant was aliquoted in an appropriate amount and stored at −80° C. to provide a glycerol stock.

Example 10

Culture of L-Lysine-Producing Strain in which fadIJ Operon was Amplified

A glycerol stock of the strain in which fadIJ operon was amplified, the strain being obtained in of Example 9, was thawed. 100 µL of each was evenly spread on an LB agar medium plate containing 50 mg/L ampicillin and 25 mg/L streptomycin and incubated at 37° C. for 24 hours. About ¼ volume of bacterial cells on the plate was suspended in 1.0 mL of saline and turbidity thereof at a wavelength of 600 nm was measured by Spectrophotometer U-2000 (Hitachi). The obtained suspension containing the bacteria was inoculated into 40 mL of fermentation medium described below containing 50 mg/L ampicillin and 25 mg/L streptomycin in a 500 mL-Erlenmeyer flask equipped with baffles such that the turbidity thereof at a wavelength of 600 nm was 0.25; and cultured using a rotary shaking culture apparatus at a stirring rate of 200 rpm at 37° C. for 48 hours. As a carbon source in a main culture, sodium oleate added with polyoxyethylene sorbitan monooleic acid ester (Tween 80: manufactured by NACALAI TESQUE, INC.) as an emulsification promoter to a final concentration of 0.5% (w/v) was used. As for a total amount of carbon sources, sodium oleate was 10 g/L. The medium composition used for the culture is shown below.

L-Lysine Production Medium for Bacteria Belonging to the Genus of *Escherichia*

| Carbon source | |
|---|---|
| Sodium oleate | 10 g/L |
| Tween 80 | 5 g/L |
| Other ingredients | |
| $(NH_4)_2SO_4$ | 24 g/L |
| $KH_2PO_4$ | 1 g/L |
| $MgSO_4 \cdot 7H_2O$ | 1 g/L |
| $FeSO_4 \cdot 7H_2O$ | 0.01 g/L |
| $MnSO_4 \cdot 7H_2O$ | 0.01 g/L |
| Yeast Extract | 2 g/L |
| PIPES (pH 7.5) | 20 g/L |

The medium was adjusted to a pH of 7.5 with KOH and autoclaved at 115° C. for 10 minutes. The carbon source, $MgSO_4 \cdot 7H_2O$, and PIPES were separately sterilized and combined.

48 hours later, the amount of L-lysine in the culture supernatant was measured by Biotech analyzer AS210 (Sakura Seiki). In this medium, the degree of growth was measured with turbidity (OD) by combining a culture solution with an equal quantity of 10% Tween 80 solution. The culture was carried out using three flasks for each and the average value thereof is shown in Table 6. Compared with a control strain in which vector pTWV228 was introduced, the strain in which fadIJ operon was introduced exhibited significantly higher L-lysine production.

TABLE 6

Results of culturing L-lysine-producing strain in which fadIJ operon was amplified

| Strain | O.D. | L-lysine (g/L) |
|---|---|---|
| AJ110692/pCABD2/pTWV228 | 4.6 | 3.3 |
| AJ110692/pCABD2/pTWV-fadIJ | 8.7 | 4.0 |

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing an L-amino acid, comprising:
   A) culturing a bacterium belonging to the Enterobacteriaceae family in a medium comprising a fatty acid or a hydrolysate of an oil-and-fat, to produce and accumulate L-amino acid in the medium or the bacterium; and
   B) collecting the L-amino acid from the medium or from the bacterium, wherein said bacterium has an enhanced ability to use a fatty acid, and has an L-amino acid-producing ability, wherein said ability to use a fatty acid is enhanced by the method selected from the group consisting of:
   a) increasing expression of a gene selected from the group consisting of fadI, fadJ, fadL, fadE, fadD, fadB, fadA, and combinations thereof,
   b) attenuating expression of fadR gene or disrupting the gene, and
   c) increasing expression of cyoABCDE operon, and wherein
   said fadI, fadJ, fadL, fadE, fadD, fadB, fadA and fadR genes, and cyoABCDE operon are from *Escherichia coli*.

2. The method according to claim 1, wherein said combination is fadB and fadA.

3. The method according to claim 1, wherein said combination is fadI and fadJ.

4. The method according to claim 1, wherein said bacterium belongs to the genus of *Escherichia*.

5. The method according to claim 1, wherein said bacterium is *Escherichia coli*.

6. The method according to claim 1, wherein said L-amino acid is selected from the group consisting of L-threonine, L-lysine, L-tryptophan, and combinations thereof.

* * * * *

SEQUENCE LISTING

<160> NUMBER OF SEQ ID NOS: 42

<210> SEQ ID NO 1
<211> LENGTH: 720
<212> TYPE: DNA
<213> ORGANISM: Escherichia coli
<220> FEATURE:
<221> NAME/KEY: CDS
<222> LOCATION: (1)..(717)

<400> SEQUENCE: 1

| | | | | | | | | | | | | | | | | |
|---|---|---|---|---|---|---|---|---|---|---|---|---|---|---|---|---|
| atg | gtc | att | aag | gcg | caa | agc | ccg | gcg | ggt | ttc | gcg | gaa | gag | tac | att | 48 |
| Met | Val | Ile | Lys | Ala | Gln | Ser | Pro | Ala | Gly | Phe | Ala | Glu | Glu | Tyr | Ile | |
| 1 | | | | 5 | | | | | 10 | | | | | 15 | | |

| att | gaa | agt | atc | tgg | aat | aac | cgc | ttc | cct | ccc | ggg | act | att | ttg | ccc | 96 |
|---|---|---|---|---|---|---|---|---|---|---|---|---|---|---|---|---|
| Ile | Glu | Ser | Ile | Trp | Asn | Asn | Arg | Phe | Pro | Pro | Gly | Thr | Ile | Leu | Pro | |
| | | | 20 | | | | | 25 | | | | | 30 | | | |

| gca | gaa | cgt | gaa | ctt | tca | gaa | tta | att | ggc | gta | acg | cgt | act | acg | tta | 144 |
|---|---|---|---|---|---|---|---|---|---|---|---|---|---|---|---|---|
| Ala | Glu | Arg | Glu | Leu | Ser | Glu | Leu | Ile | Gly | Val | Thr | Arg | Thr | Thr | Leu | |
| | | 35 | | | | | 40 | | | | | 45 | | | | |

| cgt | gaa | gtg | tta | cag | cgt | ctg | gca | cga | gat | ggc | tgg | ttg | acc | att | caa | 192 |
|---|---|---|---|---|---|---|---|---|---|---|---|---|---|---|---|---|
| Arg | Glu | Val | Leu | Gln | Arg | Leu | Ala | Arg | Asp | Gly | Trp | Leu | Thr | Ile | Gln | |
| 50 | | | | | 55 | | | | | 60 | | | | | | |

| cat | ggc | aag | ccg | acg | aag | gtg | aat | aat | ttc | tgg | gaa | act | tcc | ggt | tta | 240 |
|---|---|---|---|---|---|---|---|---|---|---|---|---|---|---|---|---|
| His | Gly | Lys | Pro | Thr | Lys | Val | Asn | Asn | Phe | Trp | Glu | Thr | Ser | Gly | Leu | |
| 65 | | | | 70 | | | | | 75 | | | | | 80 | | |

| aat | atc | ctt | gaa | aca | ctg | gcg | cga | ctg | gat | cac | gaa | agt | gtg | ccg | cag | 288 |
|---|---|---|---|---|---|---|---|---|---|---|---|---|---|---|---|---|
| Asn | Ile | Leu | Glu | Thr | Leu | Ala | Arg | Leu | Asp | His | Glu | Ser | Val | Pro | Gln | |
| | | | | 85 | | | | | 90 | | | | | 95 | | |

| ctt | att | gat | aat | ttg | ctg | tcg | gtg | cgt | acc | aat | att | tcc | act | att | ttt | 336 |
|---|---|---|---|---|---|---|---|---|---|---|---|---|---|---|---|---|
| Leu | Ile | Asp | Asn | Leu | Leu | Ser | Val | Arg | Thr | Asn | Ile | Ser | Thr | Ile | Phe | |
| | | | 100 | | | | | 105 | | | | | 110 | | | |

| att | cgc | acc | gcg | ttt | cgt | cag | cat | ccc | gat | aaa | gcg | cag | gaa | gtg | ctg | 384 |
|---|---|---|---|---|---|---|---|---|---|---|---|---|---|---|---|---|
| Ile | Arg | Thr | Ala | Phe | Arg | Gln | His | Pro | Asp | Lys | Ala | Gln | Glu | Val | Leu | |
| | | 115 | | | | | 120 | | | | | 125 | | | | |

| gct | acc | gct | aat | gaa | gtg | gcc | gat | cac | gcc | gat | gcc | ttt | gcc | gag | ctg | 432 |
|---|---|---|---|---|---|---|---|---|---|---|---|---|---|---|---|---|
| Ala | Thr | Ala | Asn | Glu | Val | Ala | Asp | His | Ala | Asp | Ala | Phe | Ala | Glu | Leu | |
| 130 | | | | | 135 | | | | | 140 | | | | | | |

| gat | tac | aac | ata | ttc | cgc | ggc | ctg | gcg | ttt | gct | tcc | ggc | aac | ccg | att | 480 |
|---|---|---|---|---|---|---|---|---|---|---|---|---|---|---|---|---|
| Asp | Tyr | Asn | Ile | Phe | Arg | Gly | Leu | Ala | Phe | Ala | Ser | Gly | Asn | Pro | Ile | |
| 145 | | | | 150 | | | | | 155 | | | | | 160 | | |

| tac | ggt | ctg | att | ctt | aac | ggg | atg | aaa | ggg | ctg | tat | acg | cgt | att | ggt | 528 |
|---|---|---|---|---|---|---|---|---|---|---|---|---|---|---|---|---|
| Tyr | Gly | Leu | Ile | Leu | Asn | Gly | Met | Lys | Gly | Leu | Tyr | Thr | Arg | Ile | Gly | |
| | | | 165 | | | | | 170 | | | | | 175 | | | |

| cgt | cac | tat | ttc | gcc | aat | ccg | gaa | gcg | cgc | agt | ctg | gcg | ctg | ggc | ttc | 576 |
|---|---|---|---|---|---|---|---|---|---|---|---|---|---|---|---|---|
| Arg | His | Tyr | Phe | Ala | Asn | Pro | Glu | Ala | Arg | Ser | Leu | Ala | Leu | Gly | Phe | |
| | | 180 | | | | | 185 | | | | | 190 | | | | |

| tac | cac | aaa | ctg | tcg | gcg | ttg | tgc | agt | gaa | ggc | gcg | cac | gat | cag | gtg | 624 |
|---|---|---|---|---|---|---|---|---|---|---|---|---|---|---|---|---|
| Tyr | His | Lys | Leu | Ser | Ala | Leu | Cys | Ser | Glu | Gly | Ala | His | Asp | Gln | Val | |
| | 195 | | | | | 200 | | | | | 205 | | | | | |

| tac | gaa | aca | gtg | cgt | cgc | tat | ggg | cat | gag | agt | ggc | gag | att | tgg | cac | 672 |
|---|---|---|---|---|---|---|---|---|---|---|---|---|---|---|---|---|
| Tyr | Glu | Thr | Val | Arg | Arg | Tyr | Gly | His | Glu | Ser | Gly | Glu | Ile | Trp | His | |
| 210 | | | | | 215 | | | | | 220 | | | | | | |

| cgg | atg | cag | aaa | aat | ctg | ccg | ggt | gat | tta | gcc | att | cag | ggg | cga | taa | 720 |
|---|---|---|---|---|---|---|---|---|---|---|---|---|---|---|---|---|
| Arg | Met | Gln | Lys | Asn | Leu | Pro | Gly | Asp | Leu | Ala | Ile | Gln | Gly | Arg | | |
| 225 | | | | 230 | | | | | 235 | | | | | | | |

<210> SEQ ID NO 2
<211> LENGTH: 239
<212> TYPE: PRT
<213> ORGANISM: Escherichia coli

<400> SEQUENCE: 2

Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
                20                  25                  30

Ala Glu Arg Glu Leu Ser Glu Leu Ile Gly Val Thr Arg Thr Thr Leu
            35                  40                  45

```
Arg Glu Val Leu Gln Arg Leu Ala Arg Asp Gly Trp Leu Thr Ile Gln
         50                  55                  60
His Gly Lys Pro Thr Lys Val Asn Asn Phe Trp Glu Thr Ser Gly Leu
 65                  70                  75                  80
Asn Ile Leu Glu Thr Leu Ala Arg Leu Asp His Glu Ser Val Pro Gln
                 85                  90                  95
Leu Ile Asp Asn Leu Leu Ser Val Arg Thr Asn Ile Ser Thr Ile Phe
                100                 105                 110
Ile Arg Thr Ala Phe Arg Gln His Pro Asp Lys Ala Gln Glu Val Leu
                115                 120                 125
Ala Thr Ala Asn Glu Val Ala Asp His Ala Asp Ala Phe Ala Glu Leu
        130                 135                 140
Asp Tyr Asn Ile Phe Arg Gly Leu Ala Phe Ala Ser Gly Asn Pro Ile
145                 150                 155                 160
Tyr Gly Leu Ile Leu Asn Gly Met Lys Gly Leu Tyr Thr Arg Ile Gly
                165                 170                 175
Arg His Tyr Phe Ala Asn Pro Glu Ala Arg Ser Leu Ala Leu Gly Phe
                180                 185                 190
Tyr His Lys Leu Ser Ala Leu Cys Ser Glu Gly Ala His Asp Gln Val
                195                 200                 205
Tyr Glu Thr Val Arg Arg Tyr Gly His Glu Ser Gly Glu Ile Trp His
        210                 215                 220
Arg Met Gln Lys Asn Leu Pro Gly Asp Leu Ala Ile Gln Gly Arg
225                 230                 235

<210> SEQ ID NO 3
<211> LENGTH: 1347
<212> TYPE: DNA
<213> ORGANISM: Escherichia coli
<220> FEATURE:
<221> NAME/KEY: CDS
<222> LOCATION: (1)..(1344)

<400> SEQUENCE: 3 atg gtc atg agc cag aaa acc ctg ttt aca aag tct gct ctc gca gtc    48
Met Val Met Ser Gln Lys Thr Leu Phe Thr Lys Ser Ala Leu Ala Val
 1               5                  10                  15 gca gtg gca ctt atc tcc acc cag gcc tgg tcg gca ggc ttt cag tta    96
Ala Val Ala Leu Ile Ser Thr Gln Ala Trp Ser Ala Gly Phe Gln Leu
                 20                  25                  30 aac gaa ttt tct tcc tct ggc ctg ggc cgg gct tat tca ggg gaa ggc   144
Asn Glu Phe Ser Ser Ser Gly Leu Gly Arg Ala Tyr Ser Gly Glu Gly
             35                  40                  45 gca att gcc gat gat gca ggt aac gtc agc cgt aac ccc gca ttg att   192
Ala Ile Ala Asp Asp Ala Gly Asn Val Ser Arg Asn Pro Ala Leu Ile
         50                  55                  60 act atg ttt gac cgc ccg aca ttt tct gcg ggt gcg gtt tat att gac   240
Thr Met Phe Asp Arg Pro Thr Phe Ser Ala Gly Ala Val Tyr Ile Asp
 65                  70                  75                  80 ccg gat gta aat atc agc gga acg tct cca tct ggt cgt agc ctg aaa   288
Pro Asp Val Asn Ile Ser Gly Thr Ser Pro Ser Gly Arg Ser Leu Lys
                 85                  90                  95 gcc gat aac atc gcg cct acg gca tgg gtt ccg aac atg cac ttt gtt   336
Ala Asp Asn Ile Ala Pro Thr Ala Trp Val Pro Asn Met His Phe Val
                100                 105                 110 gca ccg att aac gac caa ttt ggt tgg ggc gct tct att acc tct aac   384
Ala Pro Ile Asn Asp Gln Phe Gly Trp Gly Ala Ser Ile Thr Ser Asn
            115                 120                 125 tat ggt ctg gct aca gag ttt aac gat act tat gca ggc ggc tct gtc   432
```

```
                Tyr Gly Leu Ala Thr Glu Phe Asn Asp Thr Tyr Ala Gly Gly Ser Val
                    130                 135                 140 ggg ggt aca acc gac ctt gaa acc atg aac ctg aac tta agc ggt gcg        480
Gly Gly Thr Thr Asp Leu Glu Thr Met Asn Leu Asn Leu Ser Gly Ala
145                 150                 155                 160 tat cgc tta aat aat gca tgg agc ttt ggt ctt ggt ttc aac gcc gtc        528
Tyr Arg Leu Asn Asn Ala Trp Ser Phe Gly Leu Gly Phe Asn Ala Val
                165                 170                 175 tac gct cgc gcg aaa att gaa cgt ttc gca ggc gat ctg ggg cag ttg        576
Tyr Ala Arg Ala Lys Ile Glu Arg Phe Ala Gly Asp Leu Gly Gln Leu
            180                 185                 190 gtt gct ggc caa att atg caa tct cct gct ggc caa act cag caa ggg        624
Val Ala Gly Gln Ile Met Gln Ser Pro Ala Gly Gln Thr Gln Gln Gly
        195                 200                 205 caa gca ttg gca gct acc gcc aac ggt att gac agt aat acc aaa atc        672
Gln Ala Leu Ala Ala Thr Ala Asn Gly Ile Asp Ser Asn Thr Lys Ile
    210                 215                 220 gct cat ctg aac ggt aac cag tgg ggc ttt ggc tgg aac gcc gga atc        720
Ala His Leu Asn Gly Asn Gln Trp Gly Phe Gly Trp Asn Ala Gly Ile
225                 230                 235                 240 ctg tat gaa ctg gat aaa aat aac cgc tat gca ctg acc tac cgt tct        768
Leu Tyr Glu Leu Asp Lys Asn Asn Arg Tyr Ala Leu Thr Tyr Arg Ser
                245                 250                 255 gaa gtg aaa att gac ttc aaa ggt aac tac agc agc gat ctt aat cgt        816
Glu Val Lys Ile Asp Phe Lys Gly Asn Tyr Ser Ser Asp Leu Asn Arg
            260                 265                 270 gcg ttt aat aac tac ggt ttg cca att cct acc gcg aca ggt ggc gca        864
Ala Phe Asn Asn Tyr Gly Leu Pro Ile Pro Thr Ala Thr Gly Gly Ala
        275                 280                 285 acg caa tcg ggt tat ctg acg ctg aac ctg cct gaa atg tgg gaa gtg        912
Thr Gln Ser Gly Tyr Leu Thr Leu Asn Leu Pro Glu Met Trp Glu Val
    290                 295                 300 tca ggt tat aac cgt gtt gat cca cag tgg gcg att cac tat agc ctg        960
Ser Gly Tyr Asn Arg Val Asp Pro Gln Trp Ala Ile His Tyr Ser Leu
305                 310                 315                 320 gct tac acc agc tgg agt cag ttc cag cag ctg aaa gcg acc tca acc       1008
Ala Tyr Thr Ser Trp Ser Gln Phe Gln Gln Leu Lys Ala Thr Ser Thr
                325                 330                 335 agt ggc gac acg ctg ttc cag aaa cat gaa ggc ttt aaa gat gct tac       1056
Ser Gly Asp Thr Leu Phe Gln Lys His Glu Gly Phe Lys Asp Ala Tyr
            340                 345                 350 cgc atc gcg ttg ggt acc act tat tac tac gat gat aac tgg acc ttc       1104
Arg Ile Ala Leu Gly Thr Thr Tyr Tyr Tyr Asp Asp Asn Trp Thr Phe
        355                 360                 365 cgt acc ggt atc gcc ttt gat gac agc cca gtt cct gca cag aat cgt       1152
Arg Thr Gly Ile Ala Phe Asp Asp Ser Pro Val Pro Ala Gln Asn Arg
    370                 375                 380 tct atc tcc att ccg gac cag gac cgt ttc tgg ctg agt gca ggt acg       1200
Ser Ile Ser Ile Pro Asp Gln Asp Arg Phe Trp Leu Ser Ala Gly Thr
385                 390                 395                 400 act tac gca ttt aat aaa gat gct tca gtc gac gtt ggt gtt tct tat       1248
Thr Tyr Ala Phe Asn Lys Asp Ala Ser Val Asp Val Gly Val Ser Tyr
                405                 410                 415 atg cac ggt cag agc gtg aaa att aac gaa ggc cca tac cag ttc gag       1296
Met His Gly Gln Ser Val Lys Ile Asn Glu Gly Pro Tyr Gln Phe Glu
            420                 425                 430 tct gaa ggt aaa gcc tgg ctg ttc ggt act aac ttt aac tac gcg ttc       1344
Ser Glu Gly Lys Ala Trp Leu Phe Gly Thr Asn Phe Asn Tyr Ala Phe
        435                 440                 445 tga                                                                   1347
```

```
<210> SEQ ID NO 4
<211> LENGTH: 448
<212> TYPE: PRT
<213> ORGANISM: Escherichia coli

<400> SEQUENCE: 4
```

| | | | | | | | | | | | | | | |
|---|---|---|---|---|---|---|---|---|---|---|---|---|---|---|
| Met | Val | Met | Ser | Gln | Lys | Thr | Leu | Phe | Thr | Lys | Ser | Ala | Leu | Ala | Val |
| 1 | | | | 5 | | | | | 10 | | | | | 15 | |
| Ala | Val | Ala | Leu | Ile | Ser | Thr | Gln | Ala | Trp | Ser | Ala | Gly | Phe | Gln | Leu |
| | | | 20 | | | | | 25 | | | | | 30 | | |
| Asn | Glu | Phe | Ser | Ser | Ser | Gly | Leu | Gly | Arg | Ala | Tyr | Ser | Gly | Glu | Gly |
| | | 35 | | | | | 40 | | | | | 45 | | | |
| Ala | Ile | Ala | Asp | Asp | Ala | Gly | Asn | Val | Ser | Arg | Asn | Pro | Ala | Leu | Ile |
| | 50 | | | | | 55 | | | | | 60 | | | | |
| Thr | Met | Phe | Asp | Arg | Pro | Thr | Phe | Ser | Ala | Gly | Ala | Val | Tyr | Ile | Asp |
| 65 | | | | | 70 | | | | | 75 | | | | | 80 |
| Pro | Asp | Val | Asn | Ile | Ser | Gly | Thr | Ser | Pro | Ser | Gly | Arg | Ser | Leu | Lys |
| | | | | 85 | | | | | 90 | | | | | 95 | |
| Ala | Asp | Asn | Ile | Ala | Pro | Thr | Ala | Trp | Val | Pro | Asn | Met | His | Phe | Val |
| | | | 100 | | | | | 105 | | | | | 110 | | |
| Ala | Pro | Ile | Asn | Asp | Gln | Phe | Gly | Trp | Gly | Ala | Ser | Ile | Thr | Ser | Asn |
| | | 115 | | | | | 120 | | | | | 125 | | | |
| Tyr | Gly | Leu | Ala | Thr | Glu | Phe | Asn | Asp | Thr | Tyr | Ala | Gly | Gly | Ser | Val |
| | 130 | | | | | 135 | | | | | 140 | | | | |
| Gly | Gly | Thr | Thr | Asp | Leu | Glu | Thr | Met | Asn | Leu | Asn | Leu | Ser | Gly | Ala |
| 145 | | | | | 150 | | | | | 155 | | | | | 160 |
| Tyr | Arg | Leu | Asn | Asn | Ala | Trp | Ser | Phe | Gly | Leu | Gly | Phe | Asn | Ala | Val |
| | | | | 165 | | | | | 170 | | | | | 175 | |
| Tyr | Ala | Arg | Ala | Lys | Ile | Glu | Arg | Phe | Ala | Gly | Asp | Leu | Gly | Gln | Leu |
| | | | 180 | | | | | 185 | | | | | 190 | | |
| Val | Ala | Gly | Gln | Ile | Met | Gln | Ser | Pro | Ala | Gly | Gln | Thr | Gln | Gln | Gly |
| | | 195 | | | | | 200 | | | | | 205 | | | |
| Gln | Ala | Leu | Ala | Ala | Thr | Ala | Asn | Gly | Ile | Asp | Ser | Asn | Thr | Lys | Ile |
| | 210 | | | | | 215 | | | | | 220 | | | | |
| Ala | His | Leu | Asn | Gly | Asn | Gln | Trp | Gly | Phe | Gly | Trp | Asn | Ala | Gly | Ile |
| 225 | | | | | 230 | | | | | 235 | | | | | 240 |
| Leu | Tyr | Glu | Leu | Asp | Lys | Asn | Asn | Arg | Tyr | Ala | Leu | Thr | Tyr | Arg | Ser |
| | | | | 245 | | | | | 250 | | | | | 255 | |
| Glu | Val | Lys | Ile | Asp | Phe | Lys | Gly | Asn | Tyr | Ser | Ser | Asp | Leu | Asn | Arg |
| | | | 260 | | | | | 265 | | | | | 270 | | |
| Ala | Phe | Asn | Asn | Tyr | Gly | Leu | Pro | Ile | Pro | Thr | Ala | Thr | Gly | Gly | Ala |
| | | 275 | | | | | 280 | | | | | 285 | | | |
| Thr | Gln | Ser | Gly | Tyr | Leu | Thr | Leu | Asn | Leu | Pro | Glu | Met | Trp | Glu | Val |
| | 290 | | | | | 295 | | | | | 300 | | | | |
| Ser | Gly | Tyr | Asn | Arg | Val | Asp | Pro | Gln | Trp | Ala | Ile | His | Tyr | Ser | Leu |
| 305 | | | | | 310 | | | | | 315 | | | | | 320 |
| Ala | Tyr | Thr | Ser | Trp | Ser | Gln | Phe | Gln | Gln | Leu | Lys | Ala | Thr | Ser | Thr |
| | | | | 325 | | | | | 330 | | | | | 335 | |
| Ser | Gly | Asp | Thr | Leu | Phe | Gln | Lys | His | Glu | Gly | Phe | Lys | Asp | Ala | Tyr |
| | | | 340 | | | | | 345 | | | | | 350 | | |
| Arg | Ile | Ala | Leu | Gly | Thr | Thr | Tyr | Tyr | Tyr | Asp | Asp | Asn | Trp | Thr | Phe |
| | | 355 | | | | | 360 | | | | | 365 | | | |
| Arg | Thr | Gly | Ile | Ala | Phe | Asp | Asp | Ser | Pro | Val | Pro | Ala | Gln | Asn | Arg |
| | 370 | | | | | 375 | | | | | 380 | | | | |

```
Ser Ile Ser Ile Pro Asp Gln Asp Arg Phe Trp Leu Ser Ala Gly Thr
385                 390                 395                 400

Thr Tyr Ala Phe Asn Lys Asp Ala Ser Val Asp Val Gly Val Ser Tyr
            405                 410                 415

Met His Gly Gln Ser Val Lys Ile Asn Glu Gly Pro Tyr Gln Phe Glu
        420                 425                 430

Ser Glu Gly Lys Ala Trp Leu Phe Gly Thr Asn Phe Asn Tyr Ala Phe
        435                 440                 445
```

<210> SEQ ID NO 5
<211> LENGTH: 1686
<212> TYPE: DNA
<213> ORGANISM: Escherichia coli
<220> FEATURE:
<221> NAME/KEY: CDS
<222> LOCATION: (1)..(1683)

<400> SEQUENCE: 5

```
ttg aag aag gtt tgg ctt aac cgt tat ccc gcg gac gtt ccg acg gag      48
Leu Lys Lys Val Trp Leu Asn Arg Tyr Pro Ala Asp Val Pro Thr Glu
1               5                   10                  15 atc aac cct gac cgt tat caa tct ctg gta gat atg ttt gag cag tcg      96
Ile Asn Pro Asp Arg Tyr Gln Ser Leu Val Asp Met Phe Glu Gln Ser
            20                  25                  30 gtc gcg cgc tac gcc gat caa cct gcg ttt gtg aat atg ggg gag gta     144
Val Ala Arg Tyr Ala Asp Gln Pro Ala Phe Val Asn Met Gly Glu Val
        35                  40                  45 atg acc ttc cgc aag ctg gaa gaa cgc agt cgc gcg ttt gcc gct tat     192
Met Thr Phe Arg Lys Leu Glu Glu Arg Ser Arg Ala Phe Ala Ala Tyr
    50                  55                  60 ttg caa caa ggg ttg ggg ctg aag aaa ggc gat cgc gtt gcg ttg atg     240
Leu Gln Gln Gly Leu Gly Leu Lys Lys Gly Asp Arg Val Ala Leu Met
65                  70                  75                  80 atg cct aat tta ttg caa tat ccg gtg gcg ctg ttt ggc att ttg cgt     288
Met Pro Asn Leu Leu Gln Tyr Pro Val Ala Leu Phe Gly Ile Leu Arg
                85                  90                  95 gcc ggg atg atc gtc gta aac gtt aac ccg ttg tat acc ccg cgt gag     336
Ala Gly Met Ile Val Val Asn Val Asn Pro Leu Tyr Thr Pro Arg Glu
            100                 105                 110 ctt gag cat cag ctt aac gat agc ggc gca tcg gcg att gtt atc gtg     384
Leu Glu His Gln Leu Asn Asp Ser Gly Ala Ser Ala Ile Val Ile Val
        115                 120                 125 tct aac ttt gct cac aca ctg gaa aaa gtg gtt gat aaa acc gcc gtt     432
Ser Asn Phe Ala His Thr Leu Glu Lys Val Val Asp Lys Thr Ala Val
    130                 135                 140 cag cac gta att ctg acc cgt atg ggc gat cag cta tct acg gca aaa     480
Gln His Val Ile Leu Thr Arg Met Gly Asp Gln Leu Ser Thr Ala Lys
145                 150                 155                 160 ggc acg gta gtc aat ttc gtt gtt aaa tac atc aag cgt ttg gtg ccg     528
Gly Thr Val Val Asn Phe Val Val Lys Tyr Ile Lys Arg Leu Val Pro
                165                 170                 175 aaa tac cat ctg cca gat gcc att tca ttt cgt agc gca ctg cat aac     576
Lys Tyr His Leu Pro Asp Ala Ile Ser Phe Arg Ser Ala Leu His Asn
            180                 185                 190 ggc tac cgg atg cag tac gtc aaa ccc gaa ctg gtg ccg gaa gat tta     624
Gly Tyr Arg Met Gln Tyr Val Lys Pro Glu Leu Val Pro Glu Asp Leu
        195                 200                 205 gct ttt ctg caa tac acc ggc ggc acc act ggt gtg gcg aaa ggc gcg     672
Ala Phe Leu Gln Tyr Thr Gly Gly Thr Thr Gly Val Ala Lys Gly Ala
    210                 215                 220
```

```
atg ctg act cac cgc aat atg ctg gcg aac ctg gaa cag gtt aac gcg      720
Met Leu Thr His Arg Asn Met Leu Ala Asn Leu Glu Gln Val Asn Ala
225                 230                 235                 240 acc tat ggt ccg ctg ttg cat ccg ggc aaa gag ctg gtg gtg acg gcg      768
Thr Tyr Gly Pro Leu Leu His Pro Gly Lys Glu Leu Val Val Thr Ala
                245                 250                 255 ctg ccg ctg tat cac att ttt gcc ctg acc att aac tgc ctg ctg ttt      816
Leu Pro Leu Tyr His Ile Phe Ala Leu Thr Ile Asn Cys Leu Leu Phe
            260                 265                 270 atc gaa ctg ggt ggg cag aac ctg ctt atc act aac ccg cgc gat att      864
Ile Glu Leu Gly Gly Gln Asn Leu Leu Ile Thr Asn Pro Arg Asp Ile
        275                 280                 285 cca ggg ttg gta aaa gag tta gcg aaa tat ccg ttt acc gct atc acg      912
Pro Gly Leu Val Lys Glu Leu Ala Lys Tyr Pro Phe Thr Ala Ile Thr
    290                 295                 300 ggc gtt aac acc ttg ttc aat gcg ttg ctg aac aat aaa gag ttc cag      960
Gly Val Asn Thr Leu Phe Asn Ala Leu Leu Asn Asn Lys Glu Phe Gln
305                 310                 315                 320 cag ctg gat ttc tcc agt ctg cat ctt tcc gca ggc ggt ggg atg cca     1008
Gln Leu Asp Phe Ser Ser Leu His Leu Ser Ala Gly Gly Gly Met Pro
                325                 330                 335 gtg cag caa gtg gtg gca gag cgt tgg gtg aaa ctg acc gga cag tat     1056
Val Gln Gln Val Val Ala Glu Arg Trp Val Lys Leu Thr Gly Gln Tyr
            340                 345                 350 ctg ctg gaa ggc tat ggc ctt acc gag tgt gcg ccg ctg gtc agc gtt     1104
Leu Leu Glu Gly Tyr Gly Leu Thr Glu Cys Ala Pro Leu Val Ser Val
        355                 360                 365 aac cca tat gat att gat tat cat agt ggt agc atc ggt ttg ccg gtg     1152
Asn Pro Tyr Asp Ile Asp Tyr His Ser Gly Ser Ile Gly Leu Pro Val
    370                 375                 380 ccg tcg acg gaa gcc aaa ctg gtg gat gat gat gat aat gaa gta cca     1200
Pro Ser Thr Glu Ala Lys Leu Val Asp Asp Asp Asp Asn Glu Val Pro
385                 390                 395                 400 cca ggt caa ccg ggt gag ctt tgt gtc aaa gga ccg cag gtg atg ctg     1248
Pro Gly Gln Pro Gly Glu Leu Cys Val Lys Gly Pro Gln Val Met Leu
                405                 410                 415 ggt tac tgg cag cgt ccc gat gct acc gat gaa atc atc aaa aat ggc     1296
Gly Tyr Trp Gln Arg Pro Asp Ala Thr Asp Glu Ile Ile Lys Asn Gly
            420                 425                 430 tgg tta cac acc ggc gac atc gcg gta atg gat gaa gaa gga ttc ctg     1344
Trp Leu His Thr Gly Asp Ile Ala Val Met Asp Glu Glu Gly Phe Leu
        435                 440                 445 cgc att gtc gat cgt aaa aaa gac atg att ctg gtt tcc ggt ttt aac     1392
Arg Ile Val Asp Arg Lys Lys Asp Met Ile Leu Val Ser Gly Phe Asn
    450                 455                 460 gtc tat ccc aac gag att gaa gat gtc gtc atg cag cat cct ggc gta     1440
Val Tyr Pro Asn Glu Ile Glu Asp Val Val Met Gln His Pro Gly Val
465                 470                 475                 480 cag gaa gtc gcg gct gtt ggc gta cct tcc ggc tcc agt ggt gaa gcg     1488
Gln Glu Val Ala Ala Val Gly Val Pro Ser Gly Ser Ser Gly Glu Ala
                485                 490                 495 gtg aaa atc ttc gta gtg aaa aaa gat cca tcg ctt acc gaa gag tca     1536
Val Lys Ile Phe Val Val Lys Lys Asp Pro Ser Leu Thr Glu Glu Ser
            500                 505                 510 ctg gtg act ttt tgc cgc cgt cag ctc acg gga tac aaa gta ccg aag     1584
Leu Val Thr Phe Cys Arg Arg Gln Leu Thr Gly Tyr Lys Val Pro Lys
        515                 520                 525 ctg gtg gag ttt cgt gat gag tta ccg aaa tct aac gtc gga aaa att     1632
Leu Val Glu Phe Arg Asp Glu Leu Pro Lys Ser Asn Val Gly Lys Ile
    530                 535                 540
```

```
ttg cga cga gaa tta cgt gac gaa gcg cgc ggc aaa gtg gac aat aaa    1680
Leu Arg Arg Glu Leu Arg Asp Glu Ala Arg Gly Lys Val Asp Asn Lys
545                 550                 555                 560 gcc tga                                                             1686
Ala

<210> SEQ ID NO 6
<211> LENGTH: 561
<212> TYPE: PRT
<213> ORGANISM: Escherichia coli

<400> SEQUENCE: 6

Leu Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
                20                  25                  30

Val Ala Arg Tyr Ala Asp Gln Pro Ala Phe Val Asn Met Gly Glu Val
            35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Gly Met Pro
                325                 330                 335

Val Gln Gln Val Val Ala Glu Arg Trp Val Lys Leu Thr Gly Gln Tyr
            340                 345                 350
```

```
Leu Leu Glu Gly Tyr Gly Leu Thr Glu Cys Ala Pro Leu Val Ser Val
            355                 360                 365

Asn Pro Tyr Asp Ile Asp Tyr His Ser Gly Ser Ile Gly Leu Pro Val
        370                 375                 380

Pro Ser Thr Glu Ala Lys Leu Val Asp Asp Asp Asn Glu Val Pro
385                 390                 395                 400

Pro Gly Gln Pro Gly Glu Leu Cys Val Lys Gly Pro Gln Val Met Leu
                405                 410                 415

Gly Tyr Trp Gln Arg Pro Asp Ala Thr Asp Glu Ile Ile Lys Asn Gly
            420                 425                 430

Trp Leu His Thr Gly Asp Ile Ala Val Met Asp Glu Glu Gly Phe Leu
        435                 440                 445

Arg Ile Val Asp Arg Lys Lys Asp Met Ile Leu Val Ser Gly Phe Asn
    450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Ser Gly Glu Ala
                485                 490                 495

Val Lys Ile Phe Val Val Lys Lys Asp Pro Ser Leu Thr Glu Glu Ser
            500                 505                 510

Leu Val Thr Phe Cys Arg Arg Gln Leu Thr Gly Tyr Lys Val Pro Lys
        515                 520                 525

Leu Val Glu Phe Arg Asp Glu Leu Pro Lys Ser Asn Val Gly Lys Ile
    530                 535                 540

Leu Arg Arg Glu Leu Arg Asp Glu Ala Arg Gly Lys Val Asp Asn Lys
545                 550                 555                 560

Ala

<210> SEQ ID NO 7
<211> LENGTH: 2445
<212> TYPE: DNA
<213> ORGANISM: Escherichia coli
<220> FEATURE:
<221> NAME/KEY: CDS
<222> LOCATION: (1)..(2442)

<400> SEQUENCE: 7 atg atg att ttg agt att ctc gct acg gtt gtc ctg ctc ggc gcg ttg      48
Met Met Ile Leu Ser Ile Leu Ala Thr Val Val Leu Leu Gly Ala Leu
1               5                   10                  15 ttc tat cac cgc gtg agc tta ttt atc agc agt ctg att ttg ctc gcc      96
Phe Tyr His Arg Val Ser Leu Phe Ile Ser Ser Leu Ile Leu Leu Ala
            20                  25                  30 tgg aca gcc gcc ctc ggc gtt gct ggt ctg tgg tcg gcg tgg gta ctg      144
Trp Thr Ala Ala Leu Gly Val Ala Gly Leu Trp Ser Ala Trp Val Leu
        35                  40                  45 gtg cct ctg gcc att atc ctc gtg cca ttt aac ttt gcg cct atg cgt      192
Val Pro Leu Ala Ile Ile Leu Val Pro Phe Asn Phe Ala Pro Met Arg
    50                  55                  60 aag tcg atg att tcc gcg ccg gta ttt cgc ggt ttc cgt aag gtg atg      240
Lys Ser Met Ile Ser Ala Pro Val Phe Arg Gly Phe Arg Lys Val Met
65                  70                  75                  80 ccg ccg atg tcg cgc act gag aaa gaa gcg att gat gcg ggc acc acc      288
Pro Pro Met Ser Arg Thr Glu Lys Glu Ala Ile Asp Ala Gly Thr Thr
                85                  90                  95 tgg tgg gag ggc gac ttg ttc cag ggc aag ccg gac tgg aaa aag ctg      336
Trp Trp Glu Gly Asp Leu Phe Gln Gly Lys Pro Asp Trp Lys Lys Leu
            100                 105                 110
```

```
cat aac tat ccg cag ccg cgc ctg acc gcc gaa gag caa gcg ttt ctc     384
His Asn Tyr Pro Gln Pro Arg Leu Thr Ala Glu Glu Gln Ala Phe Leu
        115                 120                 125 gac ggc ccg gta gaa gaa gcc tgc cgg atg gcg aat gat ttc cag atc     432
Asp Gly Pro Val Glu Glu Ala Cys Arg Met Ala Asn Asp Phe Gln Ile
130                 135                 140 acc cat gag ctg gcg gat ctg ccg ccg gag ttg tgg gcg tac ctt aaa     480
Thr His Glu Leu Ala Asp Leu Pro Pro Glu Leu Trp Ala Tyr Leu Lys
145                 150                 155                 160 gag cat cgt ttc ttc gcg atg atc atc aaa aaa gag tac ggc ggg ctg     528
Glu His Arg Phe Phe Ala Met Ile Ile Lys Lys Glu Tyr Gly Gly Leu
                165                 170                 175 gag ttc tcg gct tat gcc cag tct cgc gtg ctg caa aaa ctc tcc ggc     576
Glu Phe Ser Ala Tyr Ala Gln Ser Arg Val Leu Gln Lys Leu Ser Gly
            180                 185                 190 gtg agc ggg atc ctg gcg att acc gtc ggc gtg cca aac tca tta ggc     624
Val Ser Gly Ile Leu Ala Ile Thr Val Gly Val Pro Asn Ser Leu Gly
        195                 200                 205 ccg ggc gaa ctg ttg caa cat tac ggc act gac gag cag aaa gat cac     672
Pro Gly Glu Leu Leu Gln His Tyr Gly Thr Asp Glu Gln Lys Asp His
    210                 215                 220 tat ctg ccg cgt ctg gcg cgt ggt cag gag atc ccc tgc ttt gca ctg     720
Tyr Leu Pro Arg Leu Ala Arg Gly Gln Glu Ile Pro Cys Phe Ala Leu
225                 230                 235                 240 acc agc ccg gaa gcg ggt tcc gat gcg ggc gcg att ccg gac acc ggg     768
Thr Ser Pro Glu Ala Gly Ser Asp Ala Gly Ala Ile Pro Asp Thr Gly
                245                 250                 255 att gtc tgc atg ggc gaa tgg cag ggc cag cag gtg ctg ggg atg cgt     816
Ile Val Cys Met Gly Glu Trp Gln Gly Gln Gln Val Leu Gly Met Arg
            260                 265                 270 ctg acc tgg aac aaa cgc tac att acg ctg gca ccg att gcg acc gtg     864
Leu Thr Trp Asn Lys Arg Tyr Ile Thr Leu Ala Pro Ile Ala Thr Val
        275                 280                 285 ctt ggg ctg gcg ttt aaa ctc tcc gac ccg gaa aaa tta ctc ggc ggt     912
Leu Gly Leu Ala Phe Lys Leu Ser Asp Pro Glu Lys Leu Leu Gly Gly
    290                 295                 300 gca gaa gat tta ggc att acc tgt gcg ctg atc cca acc acc acg ccg     960
Ala Glu Asp Leu Gly Ile Thr Cys Ala Leu Ile Pro Thr Thr Thr Pro
305                 310                 315                 320 ggc gtg gaa att ggt cgt cgc cac ttc ccg ctg aac gta ccg ttc cag    1008
Gly Val Glu Ile Gly Arg Arg His Phe Pro Leu Asn Val Pro Phe Gln
                325                 330                 335 aac gga ccg acg cgc ggt aaa gat gtc ttc gtg ccg atc gat tac atc    1056
Asn Gly Pro Thr Arg Gly Lys Asp Val Phe Val Pro Ile Asp Tyr Ile
            340                 345                 350 atc ggc ggg ccg aaa atg gcc ggg caa ggc tgg cgg atg ctg gtg gag    1104
Ile Gly Gly Pro Lys Met Ala Gly Gln Gly Trp Arg Met Leu Val Glu
        355                 360                 365 tgc ctc tcg gta ggc cgc ggc atc acc ctg cct tcc aac tca acc ggc    1152
Cys Leu Ser Val Gly Arg Gly Ile Thr Leu Pro Ser Asn Ser Thr Gly
    370                 375                 380 ggc gtg aaa tcg gta gcg ctg gca acc ggc gcg tat gct cac att cgc    1200
Gly Val Lys Ser Val Ala Leu Ala Thr Gly Ala Tyr Ala His Ile Arg
385                 390                 395                 400 cgt cag ttc aaa atc tct att ggt aag atg gaa ggg att gaa gag ccg    1248
Arg Gln Phe Lys Ile Ser Ile Gly Lys Met Glu Gly Ile Glu Glu Pro
                405                 410                 415 ctg gcg cgt att gcc ggt aat gcc tac gtg atg gat gct gcg gca tcg    1296
Leu Ala Arg Ile Ala Gly Asn Ala Tyr Val Met Asp Ala Ala Ala Ser
            420                 425                 430
```

```
ctg att acc tac ggc att atg ctc ggc gaa aaa cct gcc gtg ctg tcg         1344
Leu Ile Thr Tyr Gly Ile Met Leu Gly Glu Lys Pro Ala Val Leu Ser
        435                 440                 445 gct atc gtt aag tat cac tgt acc cac cgc ggg cag cag tcg att att         1392
Ala Ile Val Lys Tyr His Cys Thr His Arg Gly Gln Gln Ser Ile Ile
    450                 455                 460 gat gcg atg gat att acc ggc ggt aaa ggc att atg ctc ggg caa agc         1440
Asp Ala Met Asp Ile Thr Gly Gly Lys Gly Ile Met Leu Gly Gln Ser
465                 470                 475                 480 aac ttc ctg gcg cgt gct tac cag ggc gca ccg att gcc atc acc gtt         1488
Asn Phe Leu Ala Arg Ala Tyr Gln Gly Ala Pro Ile Ala Ile Thr Val
                485                 490                 495 gaa ggg gct aac att ctg acc cgc agc atg atg atc ttc gga caa gga         1536
Glu Gly Ala Asn Ile Leu Thr Arg Ser Met Met Ile Phe Gly Gln Gly
            500                 505                 510 gcg att cgt tgc cat ccg tac gtg ctg gaa gag atg gaa gcg gcg aag         1584
Ala Ile Arg Cys His Pro Tyr Val Leu Glu Glu Met Glu Ala Ala Lys
        515                 520                 525 aac aat gac gtc aac gcg ttc gat aaa ctg ttg ttc aaa cat atc ggt         1632
Asn Asn Asp Val Asn Ala Phe Asp Lys Leu Leu Phe Lys His Ile Gly
    530                 535                 540 cac gtc ggt agc aac aaa gtt cgc agc ttc tgg ctg ggc ctg acg cgc         1680
His Val Gly Ser Asn Lys Val Arg Ser Phe Trp Leu Gly Leu Thr Arg
545                 550                 555                 560 ggt tta acc agc agc acg cca acc ggc gat gcc act aaa cgc tac tat         1728
Gly Leu Thr Ser Ser Thr Pro Thr Gly Asp Ala Thr Lys Arg Tyr Tyr
                565                 570                 575 cag cac ctg aac cgc ctg agc gcc aac ctc gcc ctg ctt tct gat gtc         1776
Gln His Leu Asn Arg Leu Ser Ala Asn Leu Ala Leu Leu Ser Asp Val
            580                 585                 590 tcg atg gca gtg ctg ggc ggc agc ctg aaa cgt cgc gag cgc atc tcg         1824
Ser Met Ala Val Leu Gly Gly Ser Leu Lys Arg Arg Glu Arg Ile Ser
        595                 600                 605 gcc cgt ctg ggg gat att tta agc cag ctc tac ctc gcc tct gcc gtg         1872
Ala Arg Leu Gly Asp Ile Leu Ser Gln Leu Tyr Leu Ala Ser Ala Val
    610                 615                 620 ctg aag cgt tat gac gac gaa ggc cgt aat gaa gcc gac ctg ccg ctg         1920
Leu Lys Arg Tyr Asp Asp Glu Gly Arg Asn Glu Ala Asp Leu Pro Leu
625                 630                 635                 640 gtg cac tgg ggc gta caa gat gcg ctg tat cag gct gaa cag gcg atg         1968
Val His Trp Gly Val Gln Asp Ala Leu Tyr Gln Ala Glu Gln Ala Met
                645                 650                 655 gat gat tta ctg caa aac ttc ccg aac cgc gtg gtt gcc ggg ctg ctg         2016
Asp Asp Leu Leu Gln Asn Phe Pro Asn Arg Val Val Ala Gly Leu Leu
            660                 665                 670 aat gtg gtg atc ttc ccg acc gga cgt cat tat ctg gca cct tct gac         2064
Asn Val Val Ile Phe Pro Thr Gly Arg His Tyr Leu Ala Pro Ser Asp
        675                 680                 685 aag ctg gat cat aaa gtg gcg aag att tta caa gtg ccg aac gcc acc         2112
Lys Leu Asp His Lys Val Ala Lys Ile Leu Gln Val Pro Asn Ala Thr
    690                 695                 700 cgt tcc cgc att ggt cgc ggt cag tac ctg acg ccg agc gag cat aat         2160
Arg Ser Arg Ile Gly Arg Gly Gln Tyr Leu Thr Pro Ser Glu His Asn
705                 710                 715                 720 ccg gtt ggc ttg ctg gaa gag gcg ctg gtg gat gtg att gcc gcc gac         2208
Pro Val Gly Leu Leu Glu Glu Ala Leu Val Asp Val Ile Ala Ala Asp
                725                 730                 735 cca att cat cag cgg atc tgt aaa gag ctg ggt aaa aac ctg ccg ttt         2256
Pro Ile His Gln Arg Ile Cys Lys Glu Leu Gly Lys Asn Leu Pro Phe
            740                 745                 750
```

| | | | | | | | | | | | | | | | | |
|---|---|---|---|---|---|---|---|---|---|---|---|---|---|---|---|---|
| acc | cgt | ctg | gat | gaa | ctg | gcg | cac | aac | gcg | ctg | gtg | aag | ggg | ctg | att | 2304 |
| Thr | Arg | Leu | Asp | Glu | Leu | Ala | His | Asn | Ala | Leu | Val | Lys | Gly | Leu | Ile | |
| | | 755 | | | | 760 | | | | | 765 | | | | | |
| gat | aaa | gat | gaa | gcc | gct | att | ctg | gtg | aaa | gct | gaa | gaa | agc | cgt | ctg | 2352 |
| Asp | Lys | Asp | Glu | Ala | Ala | Ile | Leu | Val | Lys | Ala | Glu | Glu | Ser | Arg | Leu | |
| | 770 | | | | | 775 | | | | | 780 | | | | | |
| cgc | agt | att | aac | gtt | gat | gac | ttt | gat | ccg | gaa | gag | ctg | gcg | acg | aag | 2400 |
| Arg | Ser | Ile | Asn | Val | Asp | Asp | Phe | Asp | Pro | Glu | Glu | Leu | Ala | Thr | Lys | |
| 785 | | | | | 790 | | | | | 795 | | | | | 800 | |
| ccg | gta | aag | ttg | ccg | gag | aaa | gtg | cgg | aaa | gtt | gaa | gcc | gcg | taa | | 2445 |
| Pro | Val | Lys | Leu | Pro | Glu | Lys | Val | Arg | Lys | Val | Glu | Ala | Ala | | | |
| | | | | 805 | | | | | 810 | | | | | | | |

<210> SEQ ID NO 8
<211> LENGTH: 814
<212> TYPE: PRT
<213> ORGANISM: Escherichia coli

<400> SEQUENCE: 8

```
Met Met Ile Leu Ser Ile Leu Ala Thr Val Val Leu Leu Gly Ala Leu
1               5                   10                  15

Phe Tyr His Arg Val Ser Leu Phe Ile Ser Ser Leu Ile Leu Leu Ala
            20                  25                  30

Trp Thr Ala Ala Leu Gly Val Ala Gly Leu Trp Ser Ala Trp Val Leu
        35                  40                  45

Val Pro Leu Ala Ile Ile Leu Val Pro Phe Asn Phe Ala Pro Met Arg
    50                  55                  60

Lys Ser Met Ile Ser Ala Pro Val Phe Arg Gly Phe Arg Lys Val Met
65                  70                  75                  80

Pro Pro Met Ser Arg Thr Glu Lys Glu Ala Ile Asp Ala Gly Thr Thr
                85                  90                  95

Trp Trp Glu Gly Asp Leu Phe Gln Gly Lys Pro Asp Trp Lys Lys Leu
            100                 105                 110

His Asn Tyr Pro Gln Pro Arg Leu Thr Ala Glu Glu Gln Ala Phe Leu
        115                 120                 125

Asp Gly Pro Val Glu Glu Ala Cys Arg Met Ala Asn Asp Phe Gln Ile
    130                 135                 140

Thr His Glu Leu Ala Asp Leu Pro Pro Glu Leu Trp Ala Tyr Leu Lys
145                 150                 155                 160

Glu His Arg Phe Phe Ala Met Ile Ile Lys Lys Glu Tyr Gly Gly Leu
                165                 170                 175

Glu Phe Ser Ala Tyr Ala Gln Ser Arg Val Leu Gln Lys Leu Ser Gly
            180                 185                 190

Val Ser Gly Ile Leu Ala Ile Thr Val Gly Val Pro Asn Ser Leu Gly
        195                 200                 205

Pro Gly Glu Leu Leu Gln His Tyr Gly Thr Asp Glu Gln Lys Asp His
    210                 215                 220

Tyr Leu Pro Arg Leu Ala Arg Gly Gln Glu Ile Pro Cys Phe Ala Leu
225                 230                 235                 240

Thr Ser Pro Glu Ala Gly Ser Asp Ala Gly Ala Ile Pro Asp Thr Gly
                245                 250                 255

Ile Val Cys Met Gly Glu Trp Gln Gly Gln Gln Val Leu Gly Met Arg
            260                 265                 270

Leu Thr Trp Asn Lys Arg Tyr Ile Thr Leu Ala Pro Ile Ala Thr Val
        275                 280                 285

Leu Gly Leu Ala Phe Lys Leu Ser Asp Pro Glu Lys Leu Leu Gly Gly
```

```
                  290                 295                 300
Ala Glu Asp Leu Gly Ile Thr Cys Ala Leu Ile Pro Thr Thr Thr Pro
305                 310                 315                 320

Gly Val Glu Ile Gly Arg Arg His Phe Pro Leu Asn Val Pro Phe Gln
                325                 330                 335

Asn Gly Pro Thr Arg Gly Lys Asp Val Phe Val Pro Ile Asp Tyr Ile
                340                 345                 350

Ile Gly Gly Pro Lys Met Ala Gly Gln Gly Trp Arg Met Leu Val Glu
                355                 360                 365

Cys Leu Ser Val Gly Arg Gly Ile Thr Leu Pro Ser Asn Ser Thr Gly
370                 375                 380

Gly Val Lys Ser Val Ala Leu Ala Thr Gly Ala Tyr Ala His Ile Arg
385                 390                 395                 400

Arg Gln Phe Lys Ile Ser Ile Gly Lys Met Glu Gly Ile Glu Glu Pro
                405                 410                 415

Leu Ala Arg Ile Ala Gly Asn Ala Tyr Val Met Asp Ala Ala Ala Ser
                420                 425                 430

Leu Ile Thr Tyr Gly Ile Met Leu Gly Glu Lys Pro Ala Val Leu Ser
                435                 440                 445

Ala Ile Val Lys Tyr His Cys Thr His Arg Gly Gln Gln Ser Ile Ile
450                 455                 460

Asp Ala Met Asp Ile Thr Gly Gly Lys Gly Ile Met Leu Gly Gln Ser
465                 470                 475                 480

Asn Phe Leu Ala Arg Ala Tyr Gln Gly Ala Pro Ile Ala Ile Thr Val
                485                 490                 495

Glu Gly Ala Asn Ile Leu Thr Arg Ser Met Met Ile Phe Gly Gln Gly
                500                 505                 510

Ala Ile Arg Cys His Pro Tyr Val Leu Glu Glu Met Glu Ala Ala Lys
                515                 520                 525

Asn Asn Asp Val Asn Ala Phe Asp Lys Leu Leu Phe Lys His Ile Gly
                530                 535                 540

His Val Gly Ser Asn Lys Val Arg Ser Phe Trp Leu Gly Leu Thr Arg
545                 550                 555                 560

Gly Leu Thr Ser Ser Thr Pro Thr Gly Asp Ala Thr Lys Arg Tyr Tyr
                565                 570                 575

Gln His Leu Asn Arg Leu Ser Ala Asn Leu Ala Leu Leu Ser Asp Val
                580                 585                 590

Ser Met Ala Val Leu Gly Gly Ser Leu Lys Arg Arg Glu Arg Ile Ser
                595                 600                 605

Ala Arg Leu Gly Asp Ile Leu Ser Gln Leu Tyr Leu Ala Ser Ala Val
                610                 615                 620

Leu Lys Arg Tyr Asp Asp Glu Gly Arg Asn Glu Ala Asp Leu Pro Leu
625                 630                 635                 640

Val His Trp Gly Val Gln Asp Ala Leu Tyr Gln Ala Glu Gln Ala Met
                645                 650                 655

Asp Asp Leu Leu Gln Asn Phe Pro Asn Arg Val Val Ala Gly Leu Leu
                660                 665                 670

Asn Val Val Ile Phe Pro Thr Gly Arg His Tyr Leu Ala Pro Ser Asp
                675                 680                 685

Lys Leu Asp His Lys Val Ala Lys Ile Leu Gln Val Pro Asn Ala Thr
                690                 695                 700

Arg Ser Arg Ile Gly Arg Gly Gln Tyr Leu Thr Pro Ser Glu His Asn
705                 710                 715                 720
```

```
Pro Val Gly Leu Leu Glu Glu Ala Leu Val Asp Val Ile Ala Ala Asp
            725                 730                 735

Pro Ile His Gln Arg Ile Cys Lys Glu Leu Gly Lys Asn Leu Pro Phe
            740                 745                 750

Thr Arg Leu Asp Glu Leu Ala His Asn Ala Leu Val Lys Gly Leu Ile
            755                 760                 765

Asp Lys Asp Glu Ala Ala Ile Leu Val Lys Ala Glu Glu Ser Arg Leu
            770                 775                 780

Arg Ser Ile Asn Val Asp Asp Phe Asp Pro Glu Glu Leu Ala Thr Lys
785                 790                 795                 800

Pro Val Lys Leu Pro Glu Lys Val Arg Lys Val Glu Ala Ala
            805                 810

<210> SEQ ID NO 9
<211> LENGTH: 2190
<212> TYPE: DNA
<213> ORGANISM: Escherichia coli
<220> FEATURE:
<221> NAME/KEY: CDS
<222> LOCATION: (1)..(2187)

<400> SEQUENCE: 9 atg ctt tac aaa ggc gac acc ctg tac ctt gac tgg ctg gaa gat ggc      48
Met Leu Tyr Lys Gly Asp Thr Leu Tyr Leu Asp Trp Leu Glu Asp Gly
1               5                   10                  15 att gcc gaa ctg gta ttt gat gcc cca ggt tca gtt aat aaa ctc gac      96
Ile Ala Glu Leu Val Phe Asp Ala Pro Gly Ser Val Asn Lys Leu Asp
            20                  25                  30 act gcg acc gtc gcc agc ctc ggc gag gcc atc ggc gtg ctg gaa cag     144
Thr Ala Thr Val Ala Ser Leu Gly Glu Ala Ile Gly Val Leu Glu Gln
        35                  40                  45 caa tca gat cta aaa ggg ctg ctg cgt tcg aac aaa gca gcc ttt         192
Gln Ser Asp Leu Lys Gly Leu Leu Arg Ser Asn Lys Ala Ala Phe
    50                  55                  60 atc gtc ggt gct gat atc acc gaa ttt ttg tcc ctg ttc ctc gtt cct     240
Ile Val Gly Ala Asp Ile Thr Glu Phe Leu Ser Leu Phe Leu Val Pro
65                  70                  75                  80 gaa gaa cag tta agt cag tgg ctg cac ttt gcc aat agc gtg ttt aat     288
Glu Glu Gln Leu Ser Gln Trp Leu His Phe Ala Asn Ser Val Phe Asn
                85                  90                  95 cgc ctg gaa gat ctg ccg gtg ccg acc att gct gcc gtc aat ggc tat     336
Arg Leu Glu Asp Leu Pro Val Pro Thr Ile Ala Ala Val Asn Gly Tyr
            100                 105                 110 gcg ctg ggc ggt ggc tgc gaa tgc gtg ctg gcg acc gat tat cgt ctg     384
Ala Leu Gly Gly Gly Cys Glu Cys Val Leu Ala Thr Asp Tyr Arg Leu
        115                 120                 125 gcg acg ccg gat ctg cgc atc ggt ctg ccg gaa acc aaa ctg ggc atc     432
Ala Thr Pro Asp Leu Arg Ile Gly Leu Pro Glu Thr Lys Leu Gly Ile
    130                 135                 140 atg cct ggc ttt ggc ggt tct gta cgt atg cca cgt atg ctg ggc gct     480
Met Pro Gly Phe Gly Gly Ser Val Arg Met Pro Arg Met Leu Gly Ala
145                 150                 155                 160 gac agt gcg ctg gaa atc att gcc gcc ggt aaa gat gtc ggc gcg gat     528
Asp Ser Ala Leu Glu Ile Ile Ala Ala Gly Lys Asp Val Gly Ala Asp
                165                 170                 175 cag gcg ctg aaa atc ggt ctg gtg gat ggc gta gtc aaa gca gaa aaa     576
Gln Ala Leu Lys Ile Gly Leu Val Asp Gly Val Val Lys Ala Glu Lys
            180                 185                 190 ctg gtt gaa ggc gca aag gcg gtt tta cgc cag gcc att aac ggc gac     624
Leu Val Glu Gly Ala Lys Ala Val Leu Arg Gln Ala Ile Asn Gly Asp
        195                 200                 205
```

```
ctc gac tgg aaa gca aaa cgt cag ccg aag ctg gaa cca cta aaa ctg    672
Leu Asp Trp Lys Ala Lys Arg Gln Pro Lys Leu Glu Pro Leu Lys Leu
    210             215                 220 agc aag att gaa gcc acc atg agc ttc acc atc gct aaa ggg atg gtc    720
Ser Lys Ile Glu Ala Thr Met Ser Phe Thr Ile Ala Lys Gly Met Val
225                 230                 235                 240 gca caa aca gcg ggg aaa cat tat ccg gcc ccc atc acc gca gta aaa    768
Ala Gln Thr Ala Gly Lys His Tyr Pro Ala Pro Ile Thr Ala Val Lys
                245                 250                 255 acc att gaa gct gcg gcc cgt ttt ggt cgt gaa gaa gcc tta aac ctg    816
Thr Ile Glu Ala Ala Ala Arg Phe Gly Arg Glu Glu Ala Leu Asn Leu
            260                 265                 270 gaa aac aaa agt ttt gtc ccg ctg gcg cat acc aac gaa gcc cgc gca    864
Glu Asn Lys Ser Phe Val Pro Leu Ala His Thr Asn Glu Ala Arg Ala
        275                 280                 285 ctc gtc ggc att ttc ctt aac gat caa tat gta aaa ggc aaa gcg aag    912
Leu Val Gly Ile Phe Leu Asn Asp Gln Tyr Val Lys Gly Lys Ala Lys
    290                 295                 300 aaa ctc acc aaa gac gtt gaa acc ccg aaa cag gcc gcg gtg ctg ggt    960
Lys Leu Thr Lys Asp Val Glu Thr Pro Lys Gln Ala Ala Val Leu Gly
305                 310                 315                 320 gca ggc att atg ggc ggc ggc atc gct tac cag tct gcg tgg aaa ggc   1008
Ala Gly Ile Met Gly Gly Gly Ile Ala Tyr Gln Ser Ala Trp Lys Gly
                325                 330                 335 gtg ccg gtt gtc atg aaa gat atc aac gac aag tcg tta acc ctc ggc   1056
Val Pro Val Val Met Lys Asp Ile Asn Asp Lys Ser Leu Thr Leu Gly
            340                 345                 350 atg acc gaa gcc gcg aaa ctg ctg aac aag cag ctt gag cgc ggc aag   1104
Met Thr Glu Ala Ala Lys Leu Leu Asn Lys Gln Leu Glu Arg Gly Lys
        355                 360                 365 atc gat ggt ctg aaa ctg gct ggc gtg atc tcc aca atc cac cca acg   1152
Ile Asp Gly Leu Lys Leu Ala Gly Val Ile Ser Thr Ile His Pro Thr
    370                 375                 380 ctc gac tac gcc gga ttt gac cgc gtg gat att gtg gta gaa gcg gtt   1200
Leu Asp Tyr Ala Gly Phe Asp Arg Val Asp Ile Val Val Glu Ala Val
385                 390                 395                 400 gtt gaa aac ccg aaa gtg aaa aaa gcc gta ctg gca gaa acc gaa caa   1248
Val Glu Asn Pro Lys Val Lys Lys Ala Val Leu Ala Glu Thr Glu Gln
                405                 410                 415 aaa gta cgc cag gat acc gtg ctg gcg tct aac act tca acc att cct   1296
Lys Val Arg Gln Asp Thr Val Leu Ala Ser Asn Thr Ser Thr Ile Pro
            420                 425                 430 atc agc gaa ctg gcc aac gcg ctg gaa cgc ccg gaa aac ttc tgc ggg   1344
Ile Ser Glu Leu Ala Asn Ala Leu Glu Arg Pro Glu Asn Phe Cys Gly
        435                 440                 445 atg cac ttc ttt aac ccg gtc cac cga atg ccg ttg gta gaa att att   1392
Met His Phe Phe Asn Pro Val His Arg Met Pro Leu Val Glu Ile Ile
    450                 455                 460 cgc ggc gag aaa agc tcc gac gaa acc atc gcg aaa gtt gtc gcc tgg   1440
Arg Gly Glu Lys Ser Ser Asp Glu Thr Ile Ala Lys Val Val Ala Trp
465                 470                 475                 480 gcg agc aag atg ggc aag acg ccg att gtg gtt aac gac tgc ccc ggc   1488
Ala Ser Lys Met Gly Lys Thr Pro Ile Val Val Asn Asp Cys Pro Gly
                485                 490                 495 ttc ttt gtt aac cgc gtg ctg ttc ccg tat ttc gcc ggt ttc agc cag   1536
Phe Phe Val Asn Arg Val Leu Phe Pro Tyr Phe Ala Gly Phe Ser Gln
            500                 505                 510 ctg ctg cgc gac ggc gcg gat ttc cgc aag atc gac aaa gtg atg gaa   1584
Leu Leu Arg Asp Gly Ala Asp Phe Arg Lys Ile Asp Lys Val Met Glu
        515                 520                 525
```

```
aaa cag ttt ggc tgg ccg atg ggc ccg gca tat ctg ctg gac gtt gtg    1632
Lys Gln Phe Gly Trp Pro Met Gly Pro Ala Tyr Leu Leu Asp Val Val
    530                 535                 540 ggc att gat acc gcg cat cac gct cag gct gtc atg gca gca ggc ttc    1680
Gly Ile Asp Thr Ala His His Ala Gln Ala Val Met Ala Ala Gly Phe
545                 550                 555                 560 ccg cag cgg atg cag aaa gat tac cgc gat gcc atc gac gcg ctg ttt    1728
Pro Gln Arg Met Gln Lys Asp Tyr Arg Asp Ala Ile Asp Ala Leu Phe
                565                 570                 575 gat gcc aac cgc ttt ggt cag aag aac ggc ctc ggt ttc tgg cgt tat    1776
Asp Ala Asn Arg Phe Gly Gln Lys Asn Gly Leu Gly Phe Trp Arg Tyr
            580                 585                 590 aaa gaa gac agc aaa ggt aag ccg aag aaa gaa gaa gac gcc gcc gtt    1824
Lys Glu Asp Ser Lys Gly Lys Pro Lys Lys Glu Glu Asp Ala Ala Val
        595                 600                 605 gaa gac ctg ctg gca gaa gtg agc cag ccg aag cgc gat ttc agc gaa    1872
Glu Asp Leu Leu Ala Glu Val Ser Gln Pro Lys Arg Asp Phe Ser Glu
    610                 615                 620 gaa gag att atc gcc cgc atg atg atc ccg atg gtc aac gaa gtg gtg    1920
Glu Glu Ile Ile Ala Arg Met Met Ile Pro Met Val Asn Glu Val Val
625                 630                 635                 640 cgc tgt ctg gag gaa ggc att atc gcc act ccg gcg gaa gcg gat atg    1968
Arg Cys Leu Glu Glu Gly Ile Ile Ala Thr Pro Ala Glu Ala Asp Met
                645                 650                 655 gcg ctg gtc tac ggc ctg ggc ttc cct ccg ttc cac ggc ggc gcg ttc    2016
Ala Leu Val Tyr Gly Leu Gly Phe Pro Pro Phe His Gly Gly Ala Phe
            660                 665                 670 cgc tgg ctg gac acc ctc ggt agc gca aaa tac ctc gat atg gca cag    2064
Arg Trp Leu Asp Thr Leu Gly Ser Ala Lys Tyr Leu Asp Met Ala Gln
        675                 680                 685 caa tat cag cac ctc ggc ccg ctg tat gaa gtg ccg gaa ggt ctg cgt    2112
Gln Tyr Gln His Leu Gly Pro Leu Tyr Glu Val Pro Glu Gly Leu Arg
    690                 695                 700 aat aaa gcg cgt cat aac gaa ccg tac tat cct ccg gtt gag cca gcc    2160
Asn Lys Ala Arg His Asn Glu Pro Tyr Tyr Pro Pro Val Glu Pro Ala
705                 710                 715                 720 cgt ccg gtt ggc gac ctg aaa acg gct taa                            2190
Arg Pro Val Gly Asp Leu Lys Thr Ala
                725

<210> SEQ ID NO 10
<211> LENGTH: 729
<212> TYPE: PRT
<213> ORGANISM: Escherichia coli

<400> SEQUENCE: 10

Met Leu Tyr Lys Gly Asp Thr Leu Tyr Leu Asp Trp Leu Glu Asp Gly
1               5                   10                  15

Ile Ala Glu Leu Val Phe Asp Ala Pro Gly Ser Val Asn Lys Leu Asp
            20                  25                  30

Thr Ala Thr Val Ala Ser Leu Gly Glu Ala Ile Gly Val Leu Glu Gln
        35                  40                  45

Gln Ser Asp Leu Lys Gly Leu Leu Arg Ser Asn Lys Ala Ala Phe
    50                  55                  60

Ile Val Gly Ala Asp Ile Thr Glu Phe Leu Ser Leu Phe Leu Val Pro
65                  70                  75                  80

Glu Glu Gln Leu Ser Gln Trp Leu His Phe Ala Asn Ser Val Phe Asn
                85                  90                  95

Arg Leu Glu Asp Leu Pro Val Pro Thr Ile Ala Ala Val Asn Gly Tyr
```

```
              100                 105                 110
Ala Leu Gly Gly Gly Cys Glu Cys Val Leu Ala Thr Asp Tyr Arg Leu
            115                 120                 125

Ala Thr Pro Asp Leu Arg Ile Gly Leu Pro Glu Thr Lys Leu Gly Ile
            130                 135                 140

Met Pro Gly Phe Gly Gly Ser Val Arg Met Pro Arg Met Leu Gly Ala
145                 150                 155                 160

Asp Ser Ala Leu Glu Ile Ile Ala Ala Gly Lys Asp Val Gly Ala Asp
                165                 170                 175

Gln Ala Leu Lys Ile Gly Leu Val Asp Gly Val Val Lys Ala Glu Lys
            180                 185                 190

Leu Val Glu Gly Ala Lys Ala Val Leu Arg Gln Ala Ile Asn Gly Asp
            195                 200                 205

Leu Asp Trp Lys Ala Lys Arg Gln Pro Lys Leu Glu Pro Leu Lys Leu
            210                 215                 220

Ser Lys Ile Glu Ala Thr Met Ser Phe Thr Ile Ala Lys Gly Met Val
225                 230                 235                 240

Ala Gln Thr Ala Gly Lys His Tyr Pro Ala Pro Ile Thr Ala Val Lys
                245                 250                 255

Thr Ile Glu Ala Ala Ala Arg Phe Gly Arg Glu Glu Ala Leu Asn Leu
            260                 265                 270

Glu Asn Lys Ser Phe Val Pro Leu Ala His Thr Asn Glu Ala Arg Ala
            275                 280                 285

Leu Val Gly Ile Phe Leu Asn Asp Gln Tyr Val Lys Gly Lys Ala Lys
            290                 295                 300

Lys Leu Thr Lys Asp Val Glu Thr Pro Lys Gln Ala Ala Val Leu Gly
305                 310                 315                 320

Ala Gly Ile Met Gly Gly Gly Ile Ala Tyr Gln Ser Ala Trp Lys Gly
                325                 330                 335

Val Pro Val Val Met Lys Asp Ile Asn Asp Lys Ser Leu Thr Leu Gly
            340                 345                 350

Met Thr Glu Ala Ala Lys Leu Leu Asn Lys Gln Leu Glu Arg Gly Lys
            355                 360                 365

Ile Asp Gly Leu Lys Leu Ala Gly Val Ile Ser Thr Ile His Pro Thr
            370                 375                 380

Leu Asp Tyr Ala Gly Phe Asp Arg Val Asp Ile Val Val Glu Ala Val
385                 390                 395                 400

Val Glu Asn Pro Lys Val Lys Lys Ala Val Leu Ala Glu Thr Glu Gln
                405                 410                 415

Lys Val Arg Gln Asp Thr Val Leu Ala Ser Asn Thr Ser Thr Ile Pro
            420                 425                 430

Ile Ser Glu Leu Ala Asn Ala Leu Glu Arg Pro Glu Asn Phe Cys Gly
            435                 440                 445

Met His Phe Phe Asn Pro Val His Arg Met Pro Leu Val Glu Ile Ile
            450                 455                 460

Arg Gly Glu Lys Ser Ser Asp Glu Thr Ile Ala Lys Val Val Ala Trp
465                 470                 475                 480

Ala Ser Lys Met Gly Lys Thr Pro Ile Val Val Asn Asp Cys Pro Gly
                485                 490                 495

Phe Phe Val Asn Arg Val Leu Phe Pro Tyr Phe Ala Gly Phe Ser Gln
            500                 505                 510

Leu Leu Arg Asp Gly Ala Asp Phe Arg Lys Ile Asp Lys Val Met Glu
            515                 520                 525
```

```
Lys Gln Phe Gly Trp Pro Met Gly Pro Ala Tyr Leu Leu Asp Val Val
        530                 535                 540

Gly Ile Asp Thr Ala His His Ala Gln Ala Val Met Ala Ala Gly Phe
545                 550                 555                 560

Pro Gln Arg Met Gln Lys Asp Tyr Arg Asp Ala Ile Asp Ala Leu Phe
                565                 570                 575

Asp Ala Asn Arg Phe Gly Gln Lys Asn Gly Leu Gly Phe Trp Arg Tyr
            580                 585                 590

Lys Glu Asp Ser Lys Gly Lys Pro Lys Lys Glu Asp Ala Ala Val
        595                 600                 605

Glu Asp Leu Leu Ala Glu Val Ser Gln Pro Lys Arg Asp Phe Ser Glu
    610                 615                 620

Glu Glu Ile Ile Ala Arg Met Met Ile Pro Met Val Asn Glu Val Val
625                 630                 635                 640

Arg Cys Leu Glu Glu Gly Ile Ile Ala Thr Pro Ala Glu Ala Asp Met
                645                 650                 655

Ala Leu Val Tyr Gly Leu Gly Phe Pro Pro Phe His Gly Gly Ala Phe
            660                 665                 670

Arg Trp Leu Asp Thr Leu Gly Ser Ala Lys Tyr Leu Asp Met Ala Gln
        675                 680                 685

Gln Tyr Gln His Leu Gly Pro Leu Tyr Glu Val Pro Glu Gly Leu Arg
    690                 695                 700

Asn Lys Ala Arg His Asn Glu Pro Tyr Tyr Pro Val Glu Pro Ala
705                 710                 715                 720

Arg Pro Val Gly Asp Leu Lys Thr Ala
                725

<210> SEQ ID NO 11
<211> LENGTH: 1164
<212> TYPE: DNA
<213> ORGANISM: Escherichia coli
<220> FEATURE:
<221> NAME/KEY: CDS
<222> LOCATION: (1)..(1161)

<400> SEQUENCE: 11 atg gaa cag gtt gtc att gtc gat gca att cgc acc ccg atg ggc cgt    48
Met Glu Gln Val Val Ile Val Asp Ala Ile Arg Thr Pro Met Gly Arg
1               5                   10                  15 tcg aag ggc ggt gct ttt cgt aac gtg cgt gca gaa gat ctc tcc gct    96
Ser Lys Gly Gly Ala Phe Arg Asn Val Arg Ala Glu Asp Leu Ser Ala
            20                  25                  30 cat tta atg cgt agc ctg ctg gcg cgt aac ccg gcg ctg gaa gcg gcg   144
His Leu Met Arg Ser Leu Leu Ala Arg Asn Pro Ala Leu Glu Ala Ala
        35                  40                  45 gcc ctc gac gat att tac tgg ggt tgt gtg cag cag acg ctg gag cag   192
Ala Leu Asp Asp Ile Tyr Trp Gly Cys Val Gln Gln Thr Leu Glu Gln
    50                  55                  60 ggt ttt aat atc gcc cgt aac gcg gcg ctg ctg gca gaa gta cca cac   240
Gly Phe Asn Ile Ala Arg Asn Ala Ala Leu Leu Ala Glu Val Pro His
65                  70                  75                  80 tct gtc ccg gcg gtt acc gtt aat cgc ttg tgt ggt tca tcc atg cag   288
Ser Val Pro Ala Val Thr Val Asn Arg Leu Cys Gly Ser Ser Met Gln
                85                  90                  95 gca ctg cat gac gca gca cga atg atc atg act ggc gat gcg cag gca   336
Ala Leu His Asp Ala Ala Arg Met Ile Met Thr Gly Asp Ala Gln Ala
            100                 105                 110 tgt ctg gtt ggc ggc gtg gag cat atg ggc cat gtg ccg atg agt cac   384
Cys Leu Val Gly Gly Val Glu His Met Gly His Val Pro Met Ser His
```

```
ggc gtc gat ttt cac ccc ggc ctg agc cgc aat gtc gcc aaa gcg gcg      432
Gly Val Asp Phe His Pro Gly Leu Ser Arg Asn Val Ala Lys Ala Ala
130                 135                 140 ggc atg atg ggc tta acg gca gaa atg ctg gcg cgt atg cac ggt atc      480
Gly Met Met Gly Leu Thr Ala Glu Met Leu Ala Arg Met His Gly Ile
145                 150                 155                 160 agc cgt gaa atg cag gat gcc ttt gcc gcg cgg tca cac gcc cgc gcc      528
Ser Arg Glu Met Gln Asp Ala Phe Ala Ala Arg Ser His Ala Arg Ala
                165                 170                 175 tgg gcc gcc acg cag tcg gcc gca ttt aaa aat gaa atc atc ccg acc      576
Trp Ala Ala Thr Gln Ser Ala Ala Phe Lys Asn Glu Ile Ile Pro Thr
            180                 185                 190 ggt ggt cac gat gcc gac ggc gtc ctg aag cag ttt aat tac gac gaa      624
Gly Gly His Asp Ala Asp Gly Val Leu Lys Gln Phe Asn Tyr Asp Glu
        195                 200                 205 gtg att cgc ccg gaa acc acc gtg gaa gcc ctc gcc acg ctg cgt ccg      672
Val Ile Arg Pro Glu Thr Thr Val Glu Ala Leu Ala Thr Leu Arg Pro
    210                 215                 220 gcg ttt gat cca gta aac ggt atg gta acg gcg ggc aca tct tct gca      720
Ala Phe Asp Pro Val Asn Gly Met Val Thr Ala Gly Thr Ser Ser Ala
225                 230                 235                 240 ctt tcc gat ggc gca gct gcc atg ctg gtg atg agt gaa agc cgc gcc      768
Leu Ser Asp Gly Ala Ala Ala Met Leu Val Met Ser Glu Ser Arg Ala
                245                 250                 255 cat gaa tta ggt ctt aag ccg cgc gct cgt gtg cgt tcg atg gcg gtc      816
His Glu Leu Gly Leu Lys Pro Arg Ala Arg Val Arg Ser Met Ala Val
            260                 265                 270 gtt ggt tgt gac cca tcg att atg ggt tac ggc ccg gtt ccg gcc tcg      864
Val Gly Cys Asp Pro Ser Ile Met Gly Tyr Gly Pro Val Pro Ala Ser
        275                 280                 285 aaa ctg gcg ctg aaa aaa gcg ggg ctt tct gcc agc gat atc ggc gtg      912
Lys Leu Ala Leu Lys Lys Ala Gly Leu Ser Ala Ser Asp Ile Gly Val
    290                 295                 300 ttt gaa atg aac gaa gcc ttt gcc gcg cag atc ctg cca tgt att aaa      960
Phe Glu Met Asn Glu Ala Phe Ala Ala Gln Ile Leu Pro Cys Ile Lys
305                 310                 315                 320 gat ctg gga cta att gag cag att gac gag aag atc aac ctc aac ggt     1008
Asp Leu Gly Leu Ile Glu Gln Ile Asp Glu Lys Ile Asn Leu Asn Gly
                325                 330                 335 ggc gcg atc gcg ctg ggt cat ccg ctg ggt tgt tcc ggt gcg cgt atc     1056
Gly Ala Ile Ala Leu Gly His Pro Leu Gly Cys Ser Gly Ala Arg Ile
            340                 345                 350 agc acc acg ctg ctg aat ctg atg gaa cgc aaa gac gtt cag ttt ggt     1104
Ser Thr Thr Leu Leu Asn Leu Met Glu Arg Lys Asp Val Gln Phe Gly
        355                 360                 365 ctg gcg acg atg tgt atc ggt ctg ggt cag ggt att gcg acg gtg ttt     1152
Leu Ala Thr Met Cys Ile Gly Leu Gly Gln Gly Ile Ala Thr Val Phe
    370                 375                 380 gag cgg gtt taa                                                     1164
Glu Arg Val
385

<210> SEQ ID NO 12
<211> LENGTH: 387
<212> TYPE: PRT
<213> ORGANISM: Escherichia coli

<400> SEQUENCE: 12

Met Glu Gln Val Val Ile Val Asp Ala Ile Arg Thr Pro Met Gly Arg
1               5                   10                  15
```

Ser Lys Gly Gly Ala Phe Arg Asn Val Arg Ala Glu Asp Leu Ser Ala
          20                  25                  30

His Leu Met Arg Ser Leu Leu Ala Arg Asn Pro Ala Leu Glu Ala Ala
              35                  40                  45

Ala Leu Asp Asp Ile Tyr Trp Gly Cys Val Gln Gln Thr Leu Glu Gln
 50                  55                  60

Gly Phe Asn Ile Ala Arg Asn Ala Ala Leu Leu Ala Glu Val Pro His
 65                  70                  75                  80

Ser Val Pro Ala Val Thr Val Asn Arg Leu Cys Gly Ser Ser Met Gln
                  85                  90                  95

Ala Leu His Asp Ala Ala Arg Met Ile Met Thr Gly Asp Ala Gln Ala
              100                 105                 110

Cys Leu Val Gly Gly Val Glu His Met Gly His Val Pro Met Ser His
              115                 120                 125

Gly Val Asp Phe His Pro Gly Leu Ser Arg Asn Val Ala Lys Ala Ala
130                 135                 140

Gly Met Met Gly Leu Thr Ala Glu Met Leu Ala Arg Met His Gly Ile
145                 150                 155                 160

Ser Arg Glu Met Gln Asp Ala Phe Ala Ala Arg Ser His Ala Arg Ala
                  165                 170                 175

Trp Ala Ala Thr Gln Ser Ala Ala Phe Lys Asn Glu Ile Ile Pro Thr
              180                 185                 190

Gly Gly His Asp Ala Asp Gly Val Leu Lys Gln Phe Asn Tyr Asp Glu
              195                 200                 205

Val Ile Arg Pro Glu Thr Thr Val Glu Ala Leu Ala Thr Leu Arg Pro
210                 215                 220

Ala Phe Asp Pro Val Asn Gly Met Val Thr Ala Gly Thr Ser Ser Ala
225                 230                 235                 240

Leu Ser Asp Gly Ala Ala Ala Met Leu Val Met Ser Glu Ser Arg Ala
                  245                 250                 255

His Glu Leu Gly Leu Lys Pro Arg Ala Arg Val Arg Ser Met Ala Val
              260                 265                 270

Val Gly Cys Asp Pro Ser Ile Met Gly Tyr Gly Pro Val Pro Ala Ser
              275                 280                 285

Lys Leu Ala Leu Lys Lys Ala Gly Leu Ser Ala Ser Asp Ile Gly Val
290                 295                 300

Phe Glu Met Asn Glu Ala Phe Ala Ala Gln Ile Leu Pro Cys Ile Lys
305                 310                 315                 320

Asp Leu Gly Leu Ile Glu Gln Ile Asp Glu Lys Ile Asn Leu Asn Gly
                  325                 330                 335

Gly Ala Ile Ala Leu Gly His Pro Leu Gly Cys Ser Gly Ala Arg Ile
              340                 345                 350

Ser Thr Thr Leu Leu Asn Leu Met Glu Arg Lys Asp Val Gln Phe Gly
              355                 360                 365

Leu Ala Thr Met Cys Ile Gly Leu Gly Gln Gly Ile Ala Thr Val Phe
370                 375                 380

Glu Arg Val
385

<210> SEQ ID NO 13
<211> LENGTH: 948
<212> TYPE: DNA
<213> ORGANISM: Escherichia coli
<220> FEATURE:
<221> NAME/KEY: CDS

<222> LOCATION: (1)..(945)

<400> SEQUENCE: 13

```
atg aga ctc agg aaa tac aat aaa agt ttg gga tgg ttg tca tta ttt      48
Met Arg Leu Arg Lys Tyr Asn Lys Ser Leu Gly Trp Leu Ser Leu Phe
1               5                   10                  15 gca ggc act gta ttg ctc agt ggc tgt aat tct gcg ctg tta gat ccc      96
Ala Gly Thr Val Leu Leu Ser Gly Cys Asn Ser Ala Leu Leu Asp Pro
            20                  25                  30 aaa gga cag att ggt ctg gag caa cgt tca ctg ata ctg acg gca ttt     144
Lys Gly Gln Ile Gly Leu Glu Gln Arg Ser Leu Ile Leu Thr Ala Phe
        35                  40                  45 ggc ctg atg ttg att gtc gtt att ccc gca atc ttg atg gct gtt ggt     192
Gly Leu Met Leu Ile Val Val Ile Pro Ala Ile Leu Met Ala Val Gly
50                  55                  60 ttc gcc tgg aag tac cgt gcg agc aat aaa gat gct aag tac agc ccg     240
Phe Ala Trp Lys Tyr Arg Ala Ser Asn Lys Asp Ala Lys Tyr Ser Pro
65                  70                  75                  80 aac tgg tca cac tcc aat aaa gtg gaa gct gtg gtc tgg acg gta cct     288
Asn Trp Ser His Ser Asn Lys Val Glu Ala Val Val Trp Thr Val Pro
                85                  90                  95 atc tta atc atc atc ttc ctt gca gta ctg acc tgg aaa acc act cac     336
Ile Leu Ile Ile Ile Phe Leu Ala Val Leu Thr Trp Lys Thr Thr His
            100                 105                 110 gct ctt gag cct agc aag ccg ctg gca cac gac gag aag ccc att acc     384
Ala Leu Glu Pro Ser Lys Pro Leu Ala His Asp Glu Lys Pro Ile Thr
        115                 120                 125 atc gaa gtg gtt tcc atg gac tgg aaa tgg ttc ttc atc tac ccg gaa     432
Ile Glu Val Val Ser Met Asp Trp Lys Trp Phe Phe Ile Tyr Pro Glu
130                 135                 140 cag ggc att gct acc gtg aat gaa atc gct ttc ccg gcg aac act ccg     480
Gln Gly Ile Ala Thr Val Asn Glu Ile Ala Phe Pro Ala Asn Thr Pro
145                 150                 155                 160 gtg tac ttc aaa gtg acc tcc aac tcc gtg atg aac tcc ttc ttc att     528
Val Tyr Phe Lys Val Thr Ser Asn Ser Val Met Asn Ser Phe Phe Ile
                165                 170                 175 ccg cgt ctg ggt agc cag att tat gcc atg gcc ggt atg cag act cgc     576
Pro Arg Leu Gly Ser Gln Ile Tyr Ala Met Ala Gly Met Gln Thr Arg
            180                 185                 190 ctg cat ctg atc gcc aac gaa ccc ggc act tat gac ggt atc tcc gcc     624
Leu His Leu Ile Ala Asn Glu Pro Gly Thr Tyr Asp Gly Ile Ser Ala
        195                 200                 205 agc tac agc ggc ccg ggc ttc tca ggc atg aag ttc aaa gct att gca     672
Ser Tyr Ser Gly Pro Gly Phe Ser Gly Met Lys Phe Lys Ala Ile Ala
210                 215                 220 aca ccg gat cgc gcc gca ttc gac cag tgg gtc gca aaa gcg aag cag     720
Thr Pro Asp Arg Ala Ala Phe Asp Gln Trp Val Ala Lys Ala Lys Gln
225                 230                 235                 240 tcg ccg aac acc atg tct gac atg gct gcg ttc gaa aaa ctg gcc gcg     768
Ser Pro Asn Thr Met Ser Asp Met Ala Ala Phe Glu Lys Leu Ala Ala
                245                 250                 255 cct agc gaa tac aac cag gtg gaa tat ttc tcc aac gtg aaa cca gac     816
Pro Ser Glu Tyr Asn Gln Val Glu Tyr Phe Ser Asn Val Lys Pro Asp
            260                 265                 270 ttg ttt gcc gat gta att aac aag ttt atg gct cac ggt aag agc atg     864
Leu Phe Ala Asp Val Ile Asn Lys Phe Met Ala His Gly Lys Ser Met
        275                 280                 285 gac atg acc cag cca gaa ggt gag cac agc gca cac gaa ggt atg gaa     912
Asp Met Thr Gln Pro Glu Gly Glu His Ser Ala His Glu Gly Met Glu
290                 295                 300
```

```
ggc atg gac atg agc cac gcg gaa tcc gcc cat taa                    948
Gly Met Asp Met Ser His Ala Glu Ser Ala His
305                 310                 315

<210> SEQ ID NO 14
<211> LENGTH: 315
<212> TYPE: PRT
<213> ORGANISM: Escherichia coli

<400> SEQUENCE: 14

Met Arg Leu Arg Lys Tyr Asn Lys Ser Leu Gly Trp Leu Ser Leu Phe
1               5                   10                  15

Ala Gly Thr Val Leu Leu Ser Gly Cys Asn Ser Ala Leu Leu Asp Pro
            20                  25                  30

Lys Gly Gln Ile Gly Leu Glu Gln Arg Ser Leu Ile Leu Thr Ala Phe
        35                  40                  45

Gly Leu Met Leu Ile Val Val Ile Pro Ala Ile Leu Met Ala Val Gly
    50                  55                  60

Phe Ala Trp Lys Tyr Arg Ala Ser Asn Lys Asp Ala Lys Tyr Ser Pro
65                  70                  75                  80

Asn Trp Ser His Ser Asn Lys Val Glu Ala Val Val Trp Thr Val Pro
                85                  90                  95

Ile Leu Ile Ile Ile Phe Leu Ala Val Leu Thr Trp Lys Thr Thr His
            100                 105                 110

Ala Leu Glu Pro Ser Lys Pro Leu Ala His Asp Glu Lys Pro Ile Thr
        115                 120                 125

Ile Glu Val Val Ser Met Asp Trp Lys Trp Phe Phe Ile Tyr Pro Glu
    130                 135                 140

Gln Gly Ile Ala Thr Val Asn Glu Ile Ala Phe Pro Ala Asn Thr Pro
145                 150                 155                 160

Val Tyr Phe Lys Val Thr Ser Asn Ser Val Met Asn Ser Phe Phe Ile
                165                 170                 175

Pro Arg Leu Gly Ser Gln Ile Tyr Ala Met Ala Gly Met Gln Thr Arg
            180                 185                 190

Leu His Leu Ile Ala Asn Glu Pro Gly Thr Tyr Asp Gly Ile Ser Ala
        195                 200                 205

Ser Tyr Ser Gly Pro Gly Phe Ser Gly Met Lys Phe Lys Ala Ile Ala
    210                 215                 220

Thr Pro Asp Arg Ala Ala Phe Asp Gln Trp Val Ala Lys Ala Lys Gln
225                 230                 235                 240

Ser Pro Asn Thr Met Ser Asp Met Ala Phe Glu Lys Leu Ala Ala
                245                 250                 255

Pro Ser Glu Tyr Asn Gln Val Glu Tyr Phe Ser Asn Val Lys Pro Asp
            260                 265                 270

Leu Phe Ala Asp Val Ile Asn Lys Phe Met Ala His Gly Lys Ser Met
        275                 280                 285

Asp Met Thr Gln Pro Glu Gly Glu His Ser Ala His Glu Gly Met Glu
    290                 295                 300

Gly Met Asp Met Ser His Ala Glu Ser Ala His
305                 310                 315

<210> SEQ ID NO 15
<211> LENGTH: 1992
<212> TYPE: DNA
<213> ORGANISM: Escherichia coli
<220> FEATURE:
<221> NAME/KEY: CDS
<222> LOCATION: (1)..(1989)
```

<400> SEQUENCE: 15

```
atg ttc gga aaa tta tca ctt gat gca gtc ccg ttc cat gaa cct atc        48
Met Phe Gly Lys Leu Ser Leu Asp Ala Val Pro Phe His Glu Pro Ile
1               5                   10                  15 gtc atg gtt acg atc gct ggc att att ttg gga ggt ctg gcg ctc gtt        96
Val Met Val Thr Ile Ala Gly Ile Ile Leu Gly Gly Leu Ala Leu Val
                20                  25                  30 ggc ctg atc act tac ttc ggt aag tgg acc tac ctg tgg aaa gag tgg       144
Gly Leu Ile Thr Tyr Phe Gly Lys Trp Thr Tyr Leu Trp Lys Glu Trp
            35                  40                  45 ctg acc tcc gtc gac cat aaa cgc ctc ggt atc atg tat atc atc gtg       192
Leu Thr Ser Val Asp His Lys Arg Leu Gly Ile Met Tyr Ile Ile Val
        50                  55                  60 gcg att gtg atg ttg ctg cgt ggt ttt gct gac gcc att atg atg cgt       240
Ala Ile Val Met Leu Leu Arg Gly Phe Ala Asp Ala Ile Met Met Arg
65                  70                  75                  80 agc cag cag gct ctt gcc tcg gcg ggc gaa gcg ggc ttc ctg cca cct       288
Ser Gln Gln Ala Leu Ala Ser Ala Gly Glu Ala Gly Phe Leu Pro Pro
                85                  90                  95 cac cac tac gat cag atc ttt acc gcg cac ggc gtg att atg atc ttc       336
His His Tyr Asp Gln Ile Phe Thr Ala His Gly Val Ile Met Ile Phe
            100                 105                 110 ttc gtg gcg atg cct ttc gtt atc ggt ctg atg aac ctg gtg gtt ccg       384
Phe Val Ala Met Pro Phe Val Ile Gly Leu Met Asn Leu Val Val Pro
        115                 120                 125 ctg cag atc ggc gcg cgt gac gtt gcg ttc ccg ttc ctc aac aac tta       432
Leu Gln Ile Gly Ala Arg Asp Val Ala Phe Pro Phe Leu Asn Asn Leu
    130                 135                 140 agc ttc tgg ttt acc gtt gtt ggt gtg att ctg gtt aac gtt tct ctc       480
Ser Phe Trp Phe Thr Val Val Gly Val Ile Leu Val Asn Val Ser Leu
145                 150                 155                 160 ggc gtg ggc gaa ttt gcg cag acc ggc tgg ctg gcc tat cca ccg cta       528
Gly Val Gly Glu Phe Ala Gln Thr Gly Trp Leu Ala Tyr Pro Pro Leu
                165                 170                 175 tcg gga ata gag tac agt ccg gga gtc ggt gtc gat tac tgg ata tgg       576
Ser Gly Ile Glu Tyr Ser Pro Gly Val Gly Val Asp Tyr Trp Ile Trp
            180                 185                 190 agt ctc cag cta tcc ggt ata ggt acg acg ctt acc ggt atc aac ttc       624
Ser Leu Gln Leu Ser Gly Ile Gly Thr Thr Leu Thr Gly Ile Asn Phe
        195                 200                 205 ttc gtt acc att ctg aag atg cgc gca ccg ggc atg acc atg ttc aag       672
Phe Val Thr Ile Leu Lys Met Arg Ala Pro Gly Met Thr Met Phe Lys
    210                 215                 220 atg cca gta ttt acc tgg gca tca ctg tgc gcg aac gta ctg att att       720
Met Pro Val Phe Thr Trp Ala Ser Leu Cys Ala Asn Val Leu Ile Ile
225                 230                 235                 240 gct tcc ttc cca att ctg acg gtt acc gtc gcg ttg ttg acc ctg gat       768
Ala Ser Phe Pro Ile Leu Thr Val Thr Val Ala Leu Leu Thr Leu Asp
                245                 250                 255 cgc tat ctg ggc acc cat ttc ttt acc aac gat atg ggt ggc aac atg       816
Arg Tyr Leu Gly Thr His Phe Phe Thr Asn Asp Met Gly Gly Asn Met
            260                 265                 270 atg atg tac atc aac ctg att tgg gcc tgg ggc cac ccg gaa gtt tac       864
Met Met Tyr Ile Asn Leu Ile Trp Ala Trp Gly His Pro Glu Val Tyr
        275                 280                 285 atc ctg atc ctg cct gtt ttc ggt gtg ttc tcc gaa att gcg gca acc       912
Ile Leu Ile Leu Pro Val Phe Gly Val Phe Ser Glu Ile Ala Ala Thr
    290                 295                 300 ttc tcg cgt aaa cgt ctg ttt ggt tat acc tcg ctg gta tgg gca acc       960
Phe Ser Arg Lys Arg Leu Phe Gly Tyr Thr Ser Leu Val Trp Ala Thr
```

| | | |
|---|---|---|
| Phe Ser Arg Lys Arg Leu Phe Gly Tyr Thr Ser Leu Val Trp Ala Thr<br>305                    310                 315                320 | |
| gtc tgt atc acc gtg ctg tcg ttc atc gtt tgg ctg cac cac ttc ttt<br>Val Cys Ile Thr Val Leu Ser Phe Ile Val Trp Leu His His Phe Phe<br>                    325                 330                335 | 1008 |
| acg atg ggt gcg ggc gcg aac gta aac gcc ttc ttt ggt atc acc aca<br>Thr Met Gly Ala Gly Ala Asn Val Asn Ala Phe Phe Gly Ile Thr Thr<br>                 340                 345                 350 | 1056 |
| atg att atc gcc atc ccg acc ggg gtg aag atc ttc aac tgg ctg ttc<br>Met Ile Ile Ala Ile Pro Thr Gly Val Lys Ile Phe Asn Trp Leu Phe<br>            355                 360                 365 | 1104 |
| acc atg tat cag ggc cgc atc gtg ttc cat tct gcg atg ctg tgg acc<br>Thr Met Tyr Gln Gly Arg Ile Val Phe His Ser Ala Met Leu Trp Thr<br>370                    375                 380 | 1152 |
| atc ggt ttt atc gtc acc ttc tcg gtg ggc ggg atg act ggc gtg ctg<br>Ile Gly Phe Ile Val Thr Phe Ser Val Gly Gly Met Thr Gly Val Leu<br>385                    390                 395                400 | 1200 |
| ctg gcc gta ccg ggc gcg gac ttc gtt ctg cat aac agc ctg ttc ctg<br>Leu Ala Val Pro Gly Ala Asp Phe Val Leu His Asn Ser Leu Phe Leu<br>                     405                 410                415 | 1248 |
| att gcg cac ttc cat aac gtg atc atc ggc ggc gtg gtc ttc ggc tgc<br>Ile Ala His Phe His Asn Val Ile Ile Gly Gly Val Val Phe Gly Cys<br>            420                 425                 430 | 1296 |
| ttc gca ggg atg acc tac tgg tgg cct aaa gcg ttc ggt ttc aaa ctg<br>Phe Ala Gly Met Thr Tyr Trp Trp Pro Lys Ala Phe Gly Phe Lys Leu<br>435                    440                 445 | 1344 |
| aac gaa acc tgg ggt aaa cgc gcg ttc tgg ttc tgg atc atc ggc ttc<br>Asn Glu Thr Trp Gly Lys Arg Ala Phe Trp Phe Trp Ile Ile Gly Phe<br>450                    455                 460 | 1392 |
| ttc gtt gcc ttt atg cca ctg tat gcg ctg ggc ttc atg ggc atg acc<br>Phe Val Ala Phe Met Pro Leu Tyr Ala Leu Gly Phe Met Gly Met Thr<br>465                    470                 475                480 | 1440 |
| cgt cgt ttg agc cag cag att gac ccg cag ttc cac acc atg ctg atg<br>Arg Arg Leu Ser Gln Gln Ile Asp Pro Gln Phe His Thr Met Leu Met<br>                    485                 490                495 | 1488 |
| att gca gcc agc ggt gca gta ctg att gcg ctg ggt att ctc tgc ctc<br>Ile Ala Ala Ser Gly Ala Val Leu Ile Ala Leu Gly Ile Leu Cys Leu<br>            500                 505                 510 | 1536 |
| gtt att cag atg tac gtt tct att cgc gac cgc gac cag aac cgt gac<br>Val Ile Gln Met Tyr Val Ser Ile Arg Asp Arg Asp Gln Asn Arg Asp<br>515                    520                 525 | 1584 |
| ctg act ggc gac ccg tgg ggt ggc cgt acg ctg gag tgg gca acc tct<br>Leu Thr Gly Asp Pro Trp Gly Gly Arg Thr Leu Glu Trp Ala Thr Ser<br>            530                 535                 540 | 1632 |
| tcc ccg cct ccg ttc tat aac ttt gcc gta gtg ccg cac gtt cac gaa<br>Ser Pro Pro Pro Phe Tyr Asn Phe Ala Val Val Pro His Val His Glu<br>545                    550                 555                560 | 1680 |
| cgt gat gca ttc tgg gaa atg aaa gag aaa ggc gaa gcg tat aaa aag<br>Arg Asp Ala Phe Trp Glu Met Lys Glu Lys Gly Glu Ala Tyr Lys Lys<br>                    565                 570                575 | 1728 |
| cct gac cac tat gaa gaa att cat atg ccg aaa aac agc ggt gca ggt<br>Pro Asp His Tyr Glu Glu Ile His Met Pro Lys Asn Ser Gly Ala Gly<br>                 580                 585                 590 | 1776 |
| atc gtc att gca gct ttc tcc acc atc ttc ggt ttc gcc atg atc tgg<br>Ile Val Ile Ala Ala Phe Ser Thr Ile Phe Gly Phe Ala Met Ile Trp<br>            595                 600                 605 | 1824 |
| cat atc tgg tgg ctg gcg att gtt ggc ttc gca ggc atg atc atc acc<br>His Ile Trp Trp Leu Ala Ile Val Gly Phe Ala Gly Met Ile Ile Thr<br>610                    615                 620 | 1872 |
| tgg atc gtg aaa agc ttc gac gag gac gtg gat tac tac gtg ccg gtg | 1920 |

-continued

```
Trp Ile Val Lys Ser Phe Asp Glu Asp Val Asp Tyr Tyr Val Pro Val
625                 630                 635                 640 gca gaa atc gaa aaa ctg gaa aac cag cat ttc gat gag att act aag    1968
Ala Glu Ile Glu Lys Leu Glu Asn Gln His Phe Asp Glu Ile Thr Lys
                    645                 650                 655 gca ggg ctg aaa aat ggc aac tga                                    1992
Ala Gly Leu Lys Asn Gly Asn
                660

<210> SEQ ID NO 16
<211> LENGTH: 663
<212> TYPE: PRT
<213> ORGANISM: Escherichia coli

<400> SEQUENCE: 16

Met Phe Gly Lys Leu Ser Leu Asp Ala Val Pro Phe His Glu Pro Ile
1               5                   10                  15

Val Met Val Thr Ile Ala Gly Ile Ile Leu Gly Gly Leu Ala Leu Val
                20                  25                  30

Gly Leu Ile Thr Tyr Phe Gly Lys Trp Thr Tyr Leu Trp Lys Glu Trp
            35                  40                  45

Leu Thr Ser Val Asp His Lys Arg Leu Gly Ile Met Tyr Ile Ile Val
50                  55                  60

Ala Ile Val Met Leu Leu Arg Gly Phe Ala Asp Ala Ile Met Met Arg
65                  70                  75                  80

Ser Gln Gln Ala Leu Ala Ser Ala Gly Glu Ala Gly Phe Leu Pro Pro
                85                  90                  95

His His Tyr Asp Gln Ile Phe Thr Ala His Gly Val Ile Met Ile Phe
            100                 105                 110

Phe Val Ala Met Pro Phe Val Ile Gly Leu Met Asn Leu Val Val Pro
        115                 120                 125

Leu Gln Ile Gly Ala Arg Asp Val Ala Phe Pro Phe Leu Asn Asn Leu
    130                 135                 140

Ser Phe Trp Phe Thr Val Val Gly Val Ile Leu Val Asn Val Ser Leu
145                 150                 155                 160

Gly Val Gly Glu Phe Ala Gln Thr Gly Trp Leu Ala Tyr Pro Pro Leu
                165                 170                 175

Ser Gly Ile Glu Tyr Ser Pro Gly Val Gly Val Asp Tyr Trp Ile Trp
            180                 185                 190

Ser Leu Gln Leu Ser Gly Ile Gly Thr Thr Leu Thr Gly Ile Asn Phe
        195                 200                 205

Phe Val Thr Ile Leu Lys Met Arg Ala Pro Gly Met Thr Met Phe Lys
    210                 215                 220

Met Pro Val Phe Thr Trp Ala Ser Leu Cys Ala Asn Val Leu Ile Ile
225                 230                 235                 240

Ala Ser Phe Pro Ile Leu Thr Val Thr Val Ala Leu Leu Thr Leu Asp
                245                 250                 255

Arg Tyr Leu Gly Thr His Phe Phe Thr Asn Asp Met Gly Gly Asn Met
            260                 265                 270

Met Met Tyr Ile Asn Leu Ile Trp Ala Trp Gly His Pro Glu Val Tyr
        275                 280                 285

Ile Leu Ile Leu Pro Val Phe Gly Val Phe Ser Glu Ile Ala Ala Thr
    290                 295                 300

Phe Ser Arg Lys Arg Leu Phe Gly Tyr Thr Ser Leu Val Trp Ala Thr
305                 310                 315                 320

Val Cys Ile Thr Val Leu Ser Phe Ile Val Trp Leu His His Phe Phe
```

```
                    325                 330                 335
Thr Met Gly Ala Gly Ala Asn Val Asn Ala Phe Phe Gly Ile Thr Thr
            340                 345                 350
Met Ile Ile Ala Ile Pro Thr Gly Val Lys Ile Phe Asn Trp Leu Phe
            355                 360                 365
Thr Met Tyr Gln Gly Arg Ile Val Phe His Ser Ala Met Leu Trp Thr
            370                 375                 380
Ile Gly Phe Ile Val Thr Phe Ser Val Gly Met Thr Gly Val Leu
385                 390                 395                 400
Leu Ala Val Pro Gly Ala Asp Phe Val Leu His Asn Ser Leu Phe Leu
                405                 410                 415
Ile Ala His Phe His Asn Val Ile Ile Gly Gly Val Val Phe Gly Cys
            420                 425                 430
Phe Ala Gly Met Thr Tyr Trp Trp Pro Lys Ala Phe Gly Phe Lys Leu
            435                 440                 445
Asn Glu Thr Trp Gly Lys Arg Ala Phe Trp Phe Trp Ile Ile Gly Phe
        450                 455                 460
Phe Val Ala Phe Met Pro Leu Tyr Ala Leu Gly Phe Met Gly Met Thr
465                 470                 475                 480
Arg Arg Leu Ser Gln Gln Ile Asp Pro Gln Phe His Thr Met Leu Met
                485                 490                 495
Ile Ala Ala Ser Gly Ala Val Leu Ile Ala Leu Gly Ile Leu Cys Leu
            500                 505                 510
Val Ile Gln Met Tyr Val Ser Ile Arg Asp Arg Asp Gln Asn Arg Asp
            515                 520                 525
Leu Thr Gly Asp Pro Trp Gly Gly Arg Thr Leu Glu Trp Ala Thr Ser
        530                 535                 540
Ser Pro Pro Pro Phe Tyr Asn Phe Ala Val Val Pro His Val His Glu
545                 550                 555                 560
Arg Asp Ala Phe Trp Glu Met Lys Glu Lys Gly Glu Ala Tyr Lys Lys
                565                 570                 575
Pro Asp His Tyr Glu Glu Ile His Met Pro Lys Asn Ser Gly Ala Gly
            580                 585                 590
Ile Val Ile Ala Ala Phe Ser Thr Ile Phe Gly Phe Ala Met Ile Trp
        595                 600                 605
His Ile Trp Trp Leu Ala Ile Val Gly Phe Ala Gly Met Ile Ile Thr
            610                 615                 620
Trp Ile Val Lys Ser Phe Asp Glu Asp Val Asp Tyr Tyr Val Pro Val
625                 630                 635                 640
Ala Glu Ile Glu Lys Leu Glu Asn Gln His Phe Asp Glu Ile Thr Lys
                645                 650                 655
Ala Gly Leu Lys Asn Gly Asn
            660

<210> SEQ ID NO 17
<211> LENGTH: 615
<212> TYPE: DNA
<213> ORGANISM: Escherichia coli
<220> FEATURE:
<221> NAME/KEY: CDS
<222> LOCATION: (1)..(612)

<400> SEQUENCE: 17 atg gca act gat act ttg acg cac gcg act gcc cac gcg cac gaa cac     48
Met Ala Thr Asp Thr Leu Thr His Ala Thr Ala His Ala His Glu His
1               5                   10                  15
```

```
ggg cac cac gat gca ggc gga acc aaa atc ttc gga ttt tgg atc tac      96
Gly His His Asp Ala Gly Gly Thr Lys Ile Phe Gly Phe Trp Ile Tyr
             20                  25                  30 ctg atg agc gac tgc att ctg ttc tct atc ttg ttt gct acc tat gcc     144
Leu Met Ser Asp Cys Ile Leu Phe Ser Ile Leu Phe Ala Thr Tyr Ala
         35                  40                  45 gtt ctg gtg aac ggc acc gca ggc ggc ccg aca ggt aag gac att ttc     192
Val Leu Val Asn Gly Thr Ala Gly Gly Pro Thr Gly Lys Asp Ile Phe
     50                  55                  60 gaa ctg ccg ttc gtt ctg gtt gaa act ttc ttg ctg ttg ttc agc tcc     240
Glu Leu Pro Phe Val Leu Val Glu Thr Phe Leu Leu Leu Phe Ser Ser
65                  70                  75                  80 atc acc tac ggc atg gcg gct atc gcc atg tac aaa aac aac aaa agc     288
Ile Thr Tyr Gly Met Ala Ala Ile Ala Met Tyr Lys Asn Asn Lys Ser
                 85                  90                  95 cag gtt atc tcc tgg ctg gcg ttg acc tgg ttg ttt ggt gcc gga ttt     336
Gln Val Ile Ser Trp Leu Ala Leu Thr Trp Leu Phe Gly Ala Gly Phe
            100                 105                 110 atc ggg atg gaa atc tat gaa ttc cat cac ctg att gtt aac ggc atg     384
Ile Gly Met Glu Ile Tyr Glu Phe His His Leu Ile Val Asn Gly Met
        115                 120                 125 ggt ccg gat cgc agc ggc ttc ctg tca gcg ttc ttt gcg ctg gtc ggc     432
Gly Pro Asp Arg Ser Gly Phe Leu Ser Ala Phe Phe Ala Leu Val Gly
    130                 135                 140 acg cac ggt ctg cac gtc act tct ggt ctt atc tgg atg gcg gtg ctg     480
Thr His Gly Leu His Val Thr Ser Gly Leu Ile Trp Met Ala Val Leu
145                 150                 155                 160 atg gtg caa atc gcc cgt cgc ggc ctg acc agc act aac cgt acc cgc     528
Met Val Gln Ile Ala Arg Arg Gly Leu Thr Ser Thr Asn Arg Thr Arg
                165                 170                 175 atc atg tgc ctg agc ctg ttc tgg cac ttc ctg gat gtg gtt tgg atc     576
Ile Met Cys Leu Ser Leu Phe Trp His Phe Leu Asp Val Val Trp Ile
            180                 185                 190 tgt gtg ttc act gtt gtt tat ctg atg ggg gcg atg taa                 615
Cys Val Phe Thr Val Val Tyr Leu Met Gly Ala Met
        195                 200
```

<210> SEQ ID NO 18
<211> LENGTH: 204
<212> TYPE: PRT
<213> ORGANISM: Escherichia coli

<400> SEQUENCE: 18

```
Met Ala Thr Asp Thr Leu Thr His Ala Thr Ala His Ala His Glu His
1               5                   10                  15

Gly His His Asp Ala Gly Gly Thr Lys Ile Phe Gly Phe Trp Ile Tyr
             20                  25                  30

Leu Met Ser Asp Cys Ile Leu Phe Ser Ile Leu Phe Ala Thr Tyr Ala
         35                  40                  45

Val Leu Val Asn Gly Thr Ala Gly Gly Pro Thr Gly Lys Asp Ile Phe
     50                  55                  60

Glu Leu Pro Phe Val Leu Val Glu Thr Phe Leu Leu Leu Phe Ser Ser
65                  70                  75                  80

Ile Thr Tyr Gly Met Ala Ala Ile Ala Met Tyr Lys Asn Asn Lys Ser
                 85                  90                  95

Gln Val Ile Ser Trp Leu Ala Leu Thr Trp Leu Phe Gly Ala Gly Phe
            100                 105                 110

Ile Gly Met Glu Ile Tyr Glu Phe His His Leu Ile Val Asn Gly Met
        115                 120                 125
```

```
Gly Pro Asp Arg Ser Gly Phe Leu Ser Ala Phe Phe Ala Leu Val Gly
        130                 135                 140

Thr His Gly Leu His Val Thr Ser Gly Leu Ile Trp Met Ala Val Leu
145                 150                 155                 160

Met Val Gln Ile Ala Arg Arg Gly Leu Thr Ser Thr Asn Arg Thr Arg
                165                 170                 175

Ile Met Cys Leu Ser Leu Phe Trp His Phe Leu Asp Val Val Trp Ile
            180                 185                 190

Cys Val Phe Thr Val Val Tyr Leu Met Gly Ala Met
            195                 200

<210> SEQ ID NO 19
<211> LENGTH: 330
<212> TYPE: DNA
<213> ORGANISM: Escherichia coli
<220> FEATURE:
<221> NAME/KEY: CDS
<222> LOCATION: (1)..(327)

<400> SEQUENCE: 19 atg agt cat tct acc gat cac agc ggc gcg tcc cat ggc agc gta aaa     48
Met Ser His Ser Thr Asp His Ser Gly Ala Ser His Gly Ser Val Lys
1               5                   10                  15 acc tac atg aca ggc ttt atc ctg tcg atc att ctg acg gtg att ccg     96
Thr Tyr Met Thr Gly Phe Ile Leu Ser Ile Ile Leu Thr Val Ile Pro
                20                  25                  30 ttc tgg atg gtg atg aca gga gct gcc tct ccg gcc gta att ctg gga    144
Phe Trp Met Val Met Thr Gly Ala Ala Ser Pro Ala Val Ile Leu Gly
            35                  40                  45 aca atc ctg gca atg gca gtg gta cag gtt ctg gtg cat ctg gtg tgc    192
Thr Ile Leu Ala Met Ala Val Val Gln Val Leu Val His Leu Val Cys
        50                  55                  60 ttc ctg cac atg aat acc aaa tca gat gaa ggc tgg aac atg acg gcg    240
Phe Leu His Met Asn Thr Lys Ser Asp Glu Gly Trp Asn Met Thr Ala
65                  70                  75                  80 ttt gtc ttc acc gtg cta atc atc gct atc ctg gtt gta ggc tcc atc    288
Phe Val Phe Thr Val Leu Ile Ile Ala Ile Leu Val Val Gly Ser Ile
                85                  90                  95 tgg att atg tgg aac ctc aac tac aac atg atg atg cac taa            330
Trp Ile Met Trp Asn Leu Asn Tyr Asn Met Met Met His
            100                 105

<210> SEQ ID NO 20
<211> LENGTH: 109
<212> TYPE: PRT
<213> ORGANISM: Escherichia coli

<400> SEQUENCE: 20

Met Ser His Ser Thr Asp His Ser Gly Ala Ser His Gly Ser Val Lys
1               5                   10                  15

Thr Tyr Met Thr Gly Phe Ile Leu Ser Ile Ile Leu Thr Val Ile Pro
                20                  25                  30

Phe Trp Met Val Met Thr Gly Ala Ala Ser Pro Ala Val Ile Leu Gly
            35                  40                  45

Thr Ile Leu Ala Met Ala Val Val Gln Val Leu Val His Leu Val Cys
        50                  55                  60

Phe Leu His Met Asn Thr Lys Ser Asp Glu Gly Trp Asn Met Thr Ala
65                  70                  75                  80

Phe Val Phe Thr Val Leu Ile Ile Ala Ile Leu Val Val Gly Ser Ile
                85                  90                  95
```

```
Trp Ile Met Trp Asn Leu Asn Tyr Asn Met Met Met His
                100                 105
```

<210> SEQ ID NO 21
<211> LENGTH: 891
<212> TYPE: DNA
<213> ORGANISM: Escherichia coli
<220> FEATURE:
<221> NAME/KEY: CDS
<222> LOCATION: (1)..(888)

<400> SEQUENCE: 21

```
atg atg ttt aag caa tac ctg caa gta acg aaa cca ggc atc atc ttt      48
Met Met Phe Lys Gln Tyr Leu Gln Val Thr Lys Pro Gly Ile Ile Phe
1               5                   10                  15 ggc aac ctg atc tcg gtg att ggg gga ttc ctg ctg gcc tca aag ggc      96
Gly Asn Leu Ile Ser Val Ile Gly Gly Phe Leu Leu Ala Ser Lys Gly
                20                  25                  30 agc att gat tat ccc ctg ttt atc tac acg ctg gtt ggg gtg tca ctg     144
Ser Ile Asp Tyr Pro Leu Phe Ile Tyr Thr Leu Val Gly Val Ser Leu
            35                  40                  45 gtt gtg gcg tcg ggt tgt gtg ttt aac aac tac atc gac agg gat atc     192
Val Val Ala Ser Gly Cys Val Phe Asn Asn Tyr Ile Asp Arg Asp Ile
        50                  55                  60 gac aga aag atg gaa agg acg aag aat cgg gtg ctg gtg aaa ggc ctg     240
Asp Arg Lys Met Glu Arg Thr Lys Asn Arg Val Leu Val Lys Gly Leu
65                  70                  75                  80 atc tct cct gct gtc tcg ctg gtg tac gcc acg ttg ctg ggt att gct     288
Ile Ser Pro Ala Val Ser Leu Val Tyr Ala Thr Leu Leu Gly Ile Ala
                85                  90                  95 ggc ttt atg ctg ctg tgg ttt ggc gcg aat ccg ctg gcc tgc tgg ctg     336
Gly Phe Met Leu Leu Trp Phe Gly Ala Asn Pro Leu Ala Cys Trp Leu
                100                 105                 110 ggg gtg atg ggc ttt gtg gtt tat gtc ggc gtt tat agc ctg tac atg     384
Gly Val Met Gly Phe Val Val Tyr Val Gly Val Tyr Ser Leu Tyr Met
            115                 120                 125 aaa cgc cac tct gtc tac ggc acg ttg att ggt cgc ctc tcc ggc gct     432
Lys Arg His Ser Val Tyr Gly Thr Leu Ile Gly Ser Leu Ser Gly Ala
        130                 135                 140 gcg ccg ccg gtg atc ggc tac tgt gcg gta acc ggt gag ttc gat agc     480
Ala Pro Pro Val Ile Gly Tyr Cys Ala Val Thr Gly Glu Phe Asp Ser
145                 150                 155                 160 ggc gca gcg atc ctg ctg gct atc ttc agc ctg tgg cag atg cct cac     528
Gly Ala Ala Ile Leu Leu Ala Ile Phe Ser Leu Trp Gln Met Pro His
                165                 170                 175 tcc tat gcc atc gcc att ttc cgc ttt aag gat tac cag gcg gca aac     576
Ser Tyr Ala Ile Ala Ile Phe Arg Phe Lys Asp Tyr Gln Ala Ala Asn
                180                 185                 190 att ccg gta ttg cca gtg gta aaa ggc att tcg gtg gcg aag aat cac     624
Ile Pro Val Leu Pro Val Val Lys Gly Ile Ser Val Ala Lys Asn His
            195                 200                 205 atc acg ctg tat atc atc gcc ttt gcc gtt gcc acg ctg atg ctc tct     672
Ile Thr Leu Tyr Ile Ile Ala Phe Ala Val Ala Thr Leu Met Leu Ser
        210                 215                 220 ctt ggc ggt tac gct ggg tat aaa tat ctg gtg gtc gcc gcg gcg gtt     720
Leu Gly Gly Tyr Ala Gly Tyr Lys Tyr Leu Val Val Ala Ala Ala Val
225                 230                 235                 240 agc gtc tgg tgg tta ggt atg gct ctg cgc ggt tat aaa gtt gct gat     768
Ser Val Trp Trp Leu Gly Met Ala Leu Arg Gly Tyr Lys Val Ala Asp
                245                 250                 255 gac aga atc tgg gcg cgc aag ctg ttc ggc ttc tct atc atc gcc atc     816
Asp Arg Ile Trp Ala Arg Lys Leu Phe Gly Phe Ser Ile Ile Ala Ile
```

```
                   260                 265                 270
act gcc ctc tcg gtg atg atg tcc gtt gat ttt atg gta ccg gac tcg    864
Thr Ala Leu Ser Val Met Met Ser Val Asp Phe Met Val Pro Asp Ser
        275                 280                 285 cat acg ctg ctg gct gct gtg tgg taa                                891
His Thr Leu Leu Ala Ala Val Trp
    290                 295

<210> SEQ ID NO 22
<211> LENGTH: 296
<212> TYPE: PRT
<213> ORGANISM: Escherichia coli

<400> SEQUENCE: 22

Met Met Phe Lys Gln Tyr Leu Gln Val Thr Lys Pro Gly Ile Ile Phe
1               5                   10                  15

Gly Asn Leu Ile Ser Val Ile Gly Gly Phe Leu Leu Ala Ser Lys Gly
                20                  25                  30

Ser Ile Asp Tyr Pro Leu Phe Ile Tyr Thr Leu Val Gly Val Ser Leu
            35                  40                  45

Val Val Ala Ser Gly Cys Val Phe Asn Asn Tyr Ile Asp Arg Asp Ile
50                  55                  60

Asp Arg Lys Met Glu Arg Thr Lys Asn Arg Val Leu Val Lys Gly Leu
65                  70                  75                  80

Ile Ser Pro Ala Val Ser Leu Val Tyr Ala Thr Leu Leu Gly Ile Ala
                85                  90                  95

Gly Phe Met Leu Leu Trp Phe Gly Ala Asn Pro Leu Ala Cys Trp Leu
                100                 105                 110

Gly Val Met Gly Phe Val Val Tyr Val Gly Val Tyr Ser Leu Tyr Met
            115                 120                 125

Lys Arg His Ser Val Tyr Gly Thr Leu Ile Gly Ser Leu Ser Gly Ala
130                 135                 140

Ala Pro Pro Val Ile Gly Tyr Cys Ala Val Thr Gly Glu Phe Asp Ser
145                 150                 155                 160

Gly Ala Ala Ile Leu Leu Ala Ile Phe Ser Leu Trp Gln Met Pro His
                165                 170                 175

Ser Tyr Ala Ile Ala Ile Phe Arg Phe Lys Asp Tyr Gln Ala Ala Asn
                180                 185                 190

Ile Pro Val Leu Pro Val Val Lys Gly Ile Ser Val Ala Lys Asn His
            195                 200                 205

Ile Thr Leu Tyr Ile Ile Ala Phe Ala Val Ala Thr Leu Met Leu Ser
210                 215                 220

Leu Gly Gly Tyr Ala Gly Tyr Lys Tyr Leu Val Val Ala Ala Ala Val
225                 230                 235                 240

Ser Val Trp Trp Leu Gly Met Ala Leu Arg Gly Tyr Lys Val Ala Asp
                245                 250                 255

Asp Arg Ile Trp Ala Arg Lys Leu Phe Gly Phe Ser Ile Ile Ala Ile
                260                 265                 270

Thr Ala Leu Ser Val Met Met Ser Val Asp Phe Met Val Pro Asp Ser
            275                 280                 285

His Thr Leu Leu Ala Ala Val Trp
290                 295

<210> SEQ ID NO 23
<211> LENGTH: 63
<212> TYPE: DNA
<213> ORGANISM: Artificial sequence
```

```
<220> FEATURE:
<223> OTHER INFORMATION: primer

<400> SEQUENCE: 23
tatgatgagt ccaactttgt tttgctgtgt tatggaaatc tcacttgaag cctgcttttt      60
tat                                                                   63

<210> SEQ ID NO 24
<211> LENGTH: 63
<212> TYPE: DNA
<213> ORGANISM: Artificial sequence
<220> FEATURE:
<223> OTHER INFORMATION: primer

<400> SEQUENCE: 24
caaaaaaccc ctcgtttgag gggtttgctc tttaaacgga agggacgctc aagttagtat      60
aaa                                                                   63

<210> SEQ ID NO 25
<211> LENGTH: 44
<212> TYPE: DNA
<213> ORGANISM: Artificial sequence
<220> FEATURE:
<223> OTHER INFORMATION: primer

<400> SEQUENCE: 25
gtgtgtgtga attctgccag ataaacgttg tggatatttt acgc                      44

<210> SEQ ID NO 26
<211> LENGTH: 44
<212> TYPE: DNA
<213> ORGANISM: Artificial sequence
<220> FEATURE:
<223> OTHER INFORMATION: primer

<400> SEQUENCE: 26
gtgtgtgtaa gctttttaga acctatcttt aatttgagtg tatg                      44

<210> SEQ ID NO 27
<211> LENGTH: 44
<212> TYPE: DNA
<213> ORGANISM: Artificial sequence
<220> FEATURE:
<223> OTHER INFORMATION: primer

<400> SEQUENCE: 27
gtgtgtgtga attcttgctt gtttttaaag aaaaagaaac agcg                      44

<210> SEQ ID NO 28
<211> LENGTH: 44
<212> TYPE: DNA
<213> ORGANISM: Artificial sequence
<220> FEATURE:
<223> OTHER INFORMATION: primer

<400> SEQUENCE: 28
gtgtgtgtaa gcttgtaatt caaattgttt tctctttagt gggc                      44

<210> SEQ ID NO 29
<211> LENGTH: 44
<212> TYPE: DNA
<213> ORGANISM: Artificial sequence
<220> FEATURE:
<223> OTHER INFORMATION: primer

<400> SEQUENCE: 29
```

```
gtgtgtgtga attcgcgttt ccgccgcttc gttcagttcg ttac          44
```

<210> SEQ ID NO 30
<211> LENGTH: 44
<212> TYPE: DNA
<213> ORGANISM: Artificial sequence
<220> FEATURE:
<223> OTHER INFORMATION: primer

<400> SEQUENCE: 30

```
gtgtgtgtaa gcttttggga gatgagacgt atcaggtgat gagc          44
```

<210> SEQ ID NO 31
<211> LENGTH: 44
<212> TYPE: DNA
<213> ORGANISM: Artificial sequence
<220> FEATURE:
<223> OTHER INFORMATION: primer

<400> SEQUENCE: 31

```
gtgtgtgtga attcctcgcc ggagtgaata agtaacgcat ccag          44
```

<210> SEQ ID NO 32
<211> LENGTH: 44
<212> TYPE: DNA
<213> ORGANISM: Artificial sequence
<220> FEATURE:
<223> OTHER INFORMATION: primer

<400> SEQUENCE: 32

```
gtgtgtgtaa gcttctgctg cacacaaccc cagtaaatat cgtc          44
```

<210> SEQ ID NO 33
<211> LENGTH: 50
<212> TYPE: DNA
<213> ORGANISM: Artificial sequence
<220> FEATURE:
<223> OTHER INFORMATION: primer

<400> SEQUENCE: 33

```
tacccgggga tcctctagag atggaacagg ttgtcattgt cgatgcaatt    50
```

<210> SEQ ID NO 34
<211> LENGTH: 49
<212> TYPE: DNA
<213> ORGANISM: Artificial sequence
<220> FEATURE:
<223> OTHER INFORMATION: primer

<400> SEQUENCE: 34

```
ttgcatgcct gcaggtcgag tcttatcgtg cctacaaata gtccgaacc     49
```

<210> SEQ ID NO 35
<211> LENGTH: 44
<212> TYPE: DNA
<213> ORGANISM: Artificial sequence
<220> FEATURE:
<223> OTHER INFORMATION: primer

<400> SEQUENCE: 35

```
gtgtgtgtga attcctcgcc ggagtgaata agtaacgcat ccag          44
```

<210> SEQ ID NO 36
<211> LENGTH: 44
<212> TYPE: DNA
<213> ORGANISM: Artificial sequence

```
<220> FEATURE:
<223> OTHER INFORMATION: primer

<400> SEQUENCE: 36
gtgtgtgtaa gcttcagtgg catttagatc tatgacgtat ctgg         44

<210> SEQ ID NO 37
<211> LENGTH: 2145
<212> TYPE: DNA
<213> ORGANISM: Escherichia coli
<220> FEATURE:
<221> NAME/KEY: CDS
<222> LOCATION: (1)..(2142)

<400> SEQUENCE: 37
```

| | | | | | | | | | | | | | | | | |
|---|---|---|---|---|---|---|---|---|---|---|---|---|---|---|---|---|
| atg | gaa | atg | aca | tca | gcg | ttt | acc | ctt | aat | gtt | cgt | ctg | gac | aac | att | 48 |
| Met | Glu | Met | Thr | Ser | Ala | Phe | Thr | Leu | Asn | Val | Arg | Leu | Asp | Asn | Ile | |
| 1 | | | | 5 | | | | | 10 | | | | | 15 | | |
| gcc | gtt | atc | acc | atc | gac | gta | ccg | ggt | gag | aaa | atg | aat | acc | ctg | aag | 96 |
| Ala | Val | Ile | Thr | Ile | Asp | Val | Pro | Gly | Glu | Lys | Met | Asn | Thr | Leu | Lys | |
| | | | 20 | | | | | 25 | | | | | 30 | | | |
| gcg | gag | ttt | gcc | tcg | cag | gtg | cgc | gcc | att | att | aag | caa | ctc | cgt | gaa | 144 |
| Ala | Glu | Phe | Ala | Ser | Gln | Val | Arg | Ala | Ile | Ile | Lys | Gln | Leu | Arg | Glu | |
| | | 35 | | | | | 40 | | | | | 45 | | | | |
| aac | aaa | gag | ttg | cga | ggc | gtg | gtg | ttt | gtc | tcc | gct | aaa | ccg | gac | aac | 192 |
| Asn | Lys | Glu | Leu | Arg | Gly | Val | Val | Phe | Val | Ser | Ala | Lys | Pro | Asp | Asn | |
| 50 | | | | | 55 | | | | | 60 | | | | | | |
| ttc | att | gct | ggc | gca | gac | atc | aac | atg | atc | ggc | aac | tgc | aaa | acg | gcg | 240 |
| Phe | Ile | Ala | Gly | Ala | Asp | Ile | Asn | Met | Ile | Gly | Asn | Cys | Lys | Thr | Ala | |
| 65 | | | | | 70 | | | | | 75 | | | | | 80 | |
| caa | gaa | gcg | gaa | gct | ctg | gcg | cgg | cag | ggc | caa | cag | ttg | atg | gcg | gag | 288 |
| Gln | Glu | Ala | Glu | Ala | Leu | Ala | Arg | Gln | Gly | Gln | Gln | Leu | Met | Ala | Glu | |
| | | | | 85 | | | | | 90 | | | | | 95 | | |
| att | cat | gct | ttg | ccc | att | cag | gtt | atc | gcg | gct | att | cat | ggc | gct | tgc | 336 |
| Ile | His | Ala | Leu | Pro | Ile | Gln | Val | Ile | Ala | Ala | Ile | His | Gly | Ala | Cys | |
| | | | | 100 | | | | | 105 | | | | | 110 | | |
| ctg | ggt | ggt | ggg | ctg | gag | ttg | gcg | ctg | gcg | tgc | cac | ggt | cgc | gtt | tgt | 384 |
| Leu | Gly | Gly | Gly | Leu | Glu | Leu | Ala | Leu | Ala | Cys | His | Gly | Arg | Val | Cys | |
| | | | 115 | | | | | 120 | | | | | 125 | | | |
| act | gac | gat | cct | aaa | acg | gtg | ctc | ggt | ttg | cct | gaa | gta | caa | ctt | gga | 432 |
| Thr | Asp | Asp | Pro | Lys | Thr | Val | Leu | Gly | Leu | Pro | Glu | Val | Gln | Leu | Gly | |
| | | 130 | | | | | 135 | | | | | 140 | | | | |
| ttg | tta | ccc | ggt | tca | ggc | ggc | acc | cag | cgt | tta | ccg | cgt | ctg | ata | ggc | 480 |
| Leu | Leu | Pro | Gly | Ser | Gly | Gly | Thr | Gln | Arg | Leu | Pro | Arg | Leu | Ile | Gly | |
| 145 | | | | | 150 | | | | | 155 | | | | | 160 | |
| gtc | agc | aca | gca | tta | gag | atg | atc | ctc | acc | gga | aaa | caa | ctt | cgg | gcg | 528 |
| Val | Ser | Thr | Ala | Leu | Glu | Met | Ile | Leu | Thr | Gly | Lys | Gln | Leu | Arg | Ala | |
| | | | | 165 | | | | | 170 | | | | | 175 | | |
| aaa | cag | gca | tta | aag | ctg | ggg | ctg | gtg | gat | gac | gtt | gtt | ccg | cac | tcc | 576 |
| Lys | Gln | Ala | Leu | Lys | Leu | Gly | Leu | Val | Asp | Asp | Val | Val | Pro | His | Ser | |
| | | | 180 | | | | | 185 | | | | | 190 | | | |
| att | ctg | ctg | gaa | gcc | gct | gtt | gag | ctg | gca | aag | aag | gag | cgc | cca | tct | 624 |
| Ile | Leu | Leu | Glu | Ala | Ala | Val | Glu | Leu | Ala | Lys | Lys | Glu | Arg | Pro | Ser | |
| | | | | 195 | | | | | 200 | | | | | 205 | | |
| tcc | cgc | cct | cta | cct | gta | cgc | gag | cgt | att | ctg | gcg | ggg | ccg | tta | ggt | 672 |
| Ser | Arg | Pro | Leu | Pro | Val | Arg | Glu | Arg | Ile | Leu | Ala | Gly | Pro | Leu | Gly | |
| | | 210 | | | | | 215 | | | | | 220 | | | | |
| cgt | gcg | ctg | ctg | ttc | aaa | atg | gtc | ggc | aag | aaa | aca | gaa | cac | aaa | act | 720 |
| Arg | Ala | Leu | Leu | Phe | Lys | Met | Val | Gly | Lys | Lys | Thr | Glu | His | Lys | Thr | |
| 225 | | | | | 230 | | | | | 235 | | | | | 240 | |
| caa | ggc | aat | tat | ccg | gcg | aca | gaa | cgc | atc | ctg | gag | gtt | gtt | gaa | acg | 768 |
| Gln | Gly | Asn | Tyr | Pro | Ala | Thr | Glu | Arg | Ile | Leu | Glu | Val | Val | Glu | Thr | |

```
                    245              250              255
gga tta gcg cag ggc acc agc agc ggt tat gac gcc gaa gct cgg gcg     816
Gly Leu Ala Gln Gly Thr Ser Ser Gly Tyr Asp Ala Glu Ala Arg Ala
            260              265              270 ttt ggc gaa ctg gcg atg acg cca caa tcg cag gcg ctg cgt agt atc     864
Phe Gly Glu Leu Ala Met Thr Pro Gln Ser Gln Ala Leu Arg Ser Ile
        275              280              285 ttt ttt gcc agt acg gac gtg aag aaa gat ccc ggc agt gat gcg ccg     912
Phe Phe Ala Ser Thr Asp Val Lys Lys Asp Pro Gly Ser Asp Ala Pro
    290              295              300 cct gcg cca tta aac agc gtg ggg att tta ggt ggt ggc ttg atg ggc     960
Pro Ala Pro Leu Asn Ser Val Gly Ile Leu Gly Gly Gly Leu Met Gly
305              310              315              320 ggc ggt att gct tat gtc act gct tgt aaa gcg ggg att ccg gtc aga    1008
Gly Gly Ile Ala Tyr Val Thr Ala Cys Lys Ala Gly Ile Pro Val Arg
            325              330              335 att aaa gat atc aac ccg cag ggc ata aat cat gcg ctg aag tac agt    1056
Ile Lys Asp Ile Asn Pro Gln Gly Ile Asn His Ala Leu Lys Tyr Ser
        340              345              350 tgg gat cag ctg gag ggc aaa gtt cgc cgt cgt cat ctc aaa gcc agc    1104
Trp Asp Gln Leu Glu Gly Lys Val Arg Arg Arg His Leu Lys Ala Ser
    355              360              365 gaa cgt gac aaa cag ctg gca tta atc tcc gga acg acg gac tat cgc    1152
Glu Arg Asp Lys Gln Leu Ala Leu Ile Ser Gly Thr Thr Asp Tyr Arg
370              375              380 ggc ttt gcc cat cgc gat ctg att att gaa gcg gtg ttt gaa aat ctc    1200
Gly Phe Ala His Arg Asp Leu Ile Ile Glu Ala Val Phe Glu Asn Leu
385              390              395              400 gaa ttg aaa caa cag atg gtg gcg gaa gtt gag caa aat tgc gcc gct    1248
Glu Leu Lys Gln Gln Met Val Ala Glu Val Glu Gln Asn Cys Ala Ala
            405              410              415 cat acc atc ttt gct tcg aat acg tca tct tta ccg att ggt gat atc    1296
His Thr Ile Phe Ala Ser Asn Thr Ser Ser Leu Pro Ile Gly Asp Ile
        420              425              430 gcc gct cac gcc acg cga cct gag caa gtt atc ggc ctg cat ttc ttc    1344
Ala Ala His Ala Thr Arg Pro Glu Gln Val Ile Gly Leu His Phe Phe
    435              440              445 agt ccg gtg gaa aaa atg ccg ctg gtg gag att att cct cat gcg ggg    1392
Ser Pro Val Glu Lys Met Pro Leu Val Glu Ile Ile Pro His Ala Gly
450              455              460 aca tcg gcg caa acc atc gct acc aca gta aaa ctg gcg aaa aaa cag    1440
Thr Ser Ala Gln Thr Ile Ala Thr Thr Val Lys Leu Ala Lys Lys Gln
465              470              475              480 ggt aaa acg cca att gtc gtg cgt gac aaa gcc ggt ttt tac gtc aat    1488
Gly Lys Thr Pro Ile Val Val Arg Asp Lys Ala Gly Phe Tyr Val Asn
            485              490              495 cgc atc tta gcg cct tac att aat gaa gct atc cgc atg ttg acc caa    1536
Arg Ile Leu Ala Pro Tyr Ile Asn Glu Ala Ile Arg Met Leu Thr Gln
        500              505              510 ggt gaa cgg gta gag cac att gat gcc gcg cta gtg aaa ttt ggt ttt    1584
Gly Glu Arg Val Glu His Ile Asp Ala Ala Leu Val Lys Phe Gly Phe
    515              520              525 ccg gta ggc cca atc caa ctt ttg gat gag gta gga atc gac acc ggg    1632
Pro Val Gly Pro Ile Gln Leu Leu Asp Glu Val Gly Ile Asp Thr Gly
530              535              540 act aaa att att cct gta ctg gaa gcc gct tat gga gaa cgt ttt agc    1680
Thr Lys Ile Ile Pro Val Leu Glu Ala Ala Tyr Gly Glu Arg Phe Ser
545              550              555              560 gcg cct gca aat gtt gtt tct tca att ttg aac gac gat cgc aaa ggc    1728
Ala Pro Ala Asn Val Val Ser Ser Ile Leu Asn Asp Asp Arg Lys Gly
```

|     |     |     |     |     |     |     |     |     |     |     |     |     |     |     |     | |
|---|---|---|---|---|---|---|---|---|---|---|---|---|---|---|---|---|
|     |     |     | 565 |     |     |     | 570 |     |     |     | 575 |     |     |     |     | |
| aga | aaa | aat | ggc | cgg | ggt | ttc | tat | ctt | tat | ggt | cag | aaa | ggg | cgt | aaa | 1776 |
| Arg | Lys | Asn | Gly | Arg | Gly | Phe | Tyr | Leu | Tyr | Gly | Gln | Lys | Gly | Arg | Lys |     |
|     |     |     | 580 |     |     |     | 585 |     |     |     | 590 |     |     |     |     |     |
| agc | aaa | aaa | cag | gtc | gat | ccc | gcc | att | tac | ccg | ctg | att | ggc | aca | caa | 1824 |
| Ser | Lys | Lys | Gln | Val | Asp | Pro | Ala | Ile | Tyr | Pro | Leu | Ile | Gly | Thr | Gln |     |
|     | 595 |     |     |     |     | 600 |     |     |     |     | 605 |     |     |     |     |     |
| ggg | cag | ggg | cga | atc | tcc | gca | ccg | cag | gtt | gct | gaa | cgg | tgt | gtg | atg | 1872 |
| Gly | Gln | Gly | Arg | Ile | Ser | Ala | Pro | Gln | Val | Ala | Glu | Arg | Cys | Val | Met |     |
| 610 |     |     |     |     | 615 |     |     |     |     | 620 |     |     |     |     |     |     |
| ttg | atg | ctg | aat | gaa | gca | gta | cgt | tgt | gtt | gat | gag | cag | gtt | atc | cgt | 1920 |
| Leu | Met | Leu | Asn | Glu | Ala | Val | Arg | Cys | Val | Asp | Glu | Gln | Val | Ile | Arg |     |
| 625 |     |     |     |     | 630 |     |     |     |     | 635 |     |     |     |     | 640 |     |
| agc | gtg | cgt | gac | ggg | gat | att | ggc | gcg | gta | ttt | ggc | att | ggt | ttt | ccg | 1968 |
| Ser | Val | Arg | Asp | Gly | Asp | Ile | Gly | Ala | Val | Phe | Gly | Ile | Gly | Phe | Pro |     |
|     |     |     |     | 645 |     |     |     |     | 650 |     |     |     |     | 655 |     |     |
| cca | ttt | ctc | ggt | gga | ccg | ttc | cgc | tat | atc | gat | tct | ctc | ggc | gcg | ggc | 2016 |
| Pro | Phe | Leu | Gly | Gly | Pro | Phe | Arg | Tyr | Ile | Asp | Ser | Leu | Gly | Ala | Gly |     |
|     |     |     | 660 |     |     |     |     | 665 |     |     |     |     | 670 |     |     |     |
| gaa | gtg | gtt | gca | ata | atg | caa | cga | ctt | gcc | acg | cag | tat | ggt | tcc | cgt | 2064 |
| Glu | Val | Val | Ala | Ile | Met | Gln | Arg | Leu | Ala | Thr | Gln | Tyr | Gly | Ser | Arg |     |
|     |     | 675 |     |     |     |     | 680 |     |     |     |     | 685 |     |     |     |     |
| ttt | acc | cct | tgc | gag | cgt | ttg | gtc | gag | atg | ggc | gcg | cgt | ggg | gaa | agt | 2112 |
| Phe | Thr | Pro | Cys | Glu | Arg | Leu | Val | Glu | Met | Gly | Ala | Arg | Gly | Glu | Ser |     |
|     | 690 |     |     |     |     | 695 |     |     |     |     | 700 |     |     |     |     |     |
| ttt | tgg | aaa | aca | act | gca | act | gac | ctg | caa | taa |     |     |     |     |     | 2145 |
| Phe | Trp | Lys | Thr | Thr | Ala | Thr | Asp | Leu | Gln |     |     |     |     |     |     |     |
| 705 |     |     |     |     | 710 |     |     |     |     |     |     |     |     |     |     |     |

<210> SEQ ID NO 38
<211> LENGTH: 714
<212> TYPE: PRT
<213> ORGANISM: Escherichia coli

<400> SEQUENCE: 38

Met Glu Met Thr Ser Ala Phe Thr Leu Asn Val Arg Leu Asp Asn Ile
1               5                   10                  15

Ala Val Ile Thr Ile Asp Val Pro Gly Glu Lys Met Asn Thr Leu Lys
            20                  25                  30

Ala Glu Phe Ala Ser Gln Val Arg Ala Ile Ile Lys Gln Leu Arg Glu
        35                  40                  45

Asn Lys Glu Leu Arg Gly Val Val Phe Val Ser Ala Lys Pro Asp Asn
    50                  55                  60

Phe Ile Ala Gly Ala Asp Ile Asn Met Ile Gly Asn Cys Lys Thr Ala
65                  70                  75                  80

Gln Glu Ala Glu Ala Leu Ala Arg Gln Gly Gln Gln Leu Met Ala Glu
                85                  90                  95

Ile His Ala Leu Pro Ile Gln Val Ile Ala Ala Ile His Gly Ala Cys
            100                 105                 110

Leu Gly Gly Gly Leu Glu Leu Ala Leu Ala Cys His Gly Arg Val Cys
        115                 120                 125

Thr Asp Asp Pro Lys Thr Val Leu Gly Leu Pro Glu Val Gln Leu Gly
    130                 135                 140

Leu Leu Pro Gly Ser Gly Gly Thr Gln Arg Leu Pro Arg Leu Ile Gly
145                 150                 155                 160

Val Ser Thr Ala Leu Glu Met Ile Leu Thr Gly Lys Gln Leu Arg Ala
                165                 170                 175

Lys Gln Ala Leu Lys Leu Gly Leu Val Asp Asp Val Val Pro His Ser

```
            180                 185                 190
Ile Leu Leu Glu Ala Ala Val Glu Leu Ala Lys Lys Glu Arg Pro Ser
            195                 200                 205

Ser Arg Pro Leu Pro Val Arg Glu Arg Ile Leu Ala Gly Pro Leu Gly
            210                 215                 220

Arg Ala Leu Leu Phe Lys Met Val Gly Lys Lys Thr Glu His Lys Thr
225                 230                 235                 240

Gln Gly Asn Tyr Pro Ala Thr Glu Arg Ile Leu Glu Val Val Glu Thr
            245                 250                 255

Gly Leu Ala Gln Gly Thr Ser Ser Gly Tyr Asp Ala Glu Ala Arg Ala
            260                 265                 270

Phe Gly Glu Leu Ala Met Thr Pro Gln Ser Gln Ala Leu Arg Ser Ile
            275                 280                 285

Phe Phe Ala Ser Thr Asp Val Lys Lys Asp Pro Gly Ser Asp Ala Pro
            290                 295                 300

Pro Ala Pro Leu Asn Ser Val Gly Ile Leu Gly Gly Leu Met Gly
305                 310                 315                 320

Gly Gly Ile Ala Tyr Val Thr Ala Cys Lys Ala Gly Ile Pro Val Arg
            325                 330                 335

Ile Lys Asp Ile Asn Pro Gln Gly Ile Asn His Ala Leu Lys Tyr Ser
            340                 345                 350

Trp Asp Gln Leu Glu Gly Lys Val Arg Arg His Leu Lys Ala Ser
            355                 360                 365

Glu Arg Asp Lys Gln Leu Ala Leu Ile Ser Gly Thr Thr Asp Tyr Arg
            370                 375                 380

Gly Phe Ala His Arg Asp Leu Ile Ile Glu Ala Val Phe Glu Asn Leu
385                 390                 395                 400

Glu Leu Lys Gln Gln Met Val Ala Glu Val Glu Gln Asn Cys Ala Ala
            405                 410                 415

His Thr Ile Phe Ala Ser Asn Thr Ser Ser Leu Pro Ile Gly Asp Ile
            420                 425                 430

Ala Ala His Ala Thr Arg Pro Glu Gln Val Ile Gly Leu His Phe Phe
            435                 440                 445

Ser Pro Val Glu Lys Met Pro Leu Val Glu Ile Ile Pro His Ala Gly
            450                 455                 460

Thr Ser Ala Gln Thr Ile Ala Thr Thr Val Lys Leu Ala Lys Lys Gln
465                 470                 475                 480

Gly Lys Thr Pro Ile Val Val Arg Asp Lys Ala Gly Phe Tyr Val Asn
            485                 490                 495

Arg Ile Leu Ala Pro Tyr Ile Asn Glu Ala Ile Arg Met Leu Thr Gln
            500                 505                 510

Gly Glu Arg Val Glu His Ile Asp Ala Ala Leu Val Lys Phe Gly Phe
            515                 520                 525

Pro Val Gly Pro Ile Gln Leu Leu Asp Glu Val Gly Ile Asp Thr Gly
            530                 535                 540

Thr Lys Ile Ile Pro Val Leu Glu Ala Ala Tyr Gly Glu Arg Phe Ser
545                 550                 555                 560

Ala Pro Ala Asn Val Val Ser Ser Ile Leu Asn Asp Asp Arg Lys Gly
            565                 570                 575

Arg Lys Asn Gly Arg Gly Phe Tyr Leu Tyr Gly Gln Lys Gly Arg Lys
            580                 585                 590

Ser Lys Lys Gln Val Asp Pro Ala Ile Tyr Pro Leu Ile Gly Thr Gln
            595                 600                 605
```

```
Gly Gln Gly Arg Ile Ser Ala Pro Gln Val Ala Glu Arg Cys Val Met
        610             615                 620

Leu Met Leu Asn Glu Ala Val Arg Cys Val Asp Glu Gln Val Ile Arg
625                 630                 635                 640

Ser Val Arg Asp Gly Asp Ile Gly Ala Val Phe Gly Ile Gly Phe Pro
                645                 650                 655

Pro Phe Leu Gly Gly Pro Phe Arg Tyr Ile Asp Ser Leu Gly Ala Gly
            660                 665                 670

Glu Val Ala Ile Met Gln Arg Leu Ala Thr Gln Tyr Gly Ser Arg
        675                 680                 685

Phe Thr Pro Cys Glu Arg Leu Val Glu Met Gly Ala Arg Gly Glu Ser
        690                 695                 700

Phe Trp Lys Thr Thr Ala Thr Asp Leu Gln
705                 710

<210> SEQ ID NO 39
<211> LENGTH: 1311
<212> TYPE: DNA
<213> ORGANISM: Escherichia coli
<220> FEATURE:
<221> NAME/KEY: CDS
<222> LOCATION: (1)..(1308)

<400> SEQUENCE: 39 atg ggt cag gtt tta ccg ctg gtt acc cgc cag ggc gat cgt atc gcc      48
Met Gly Gln Val Leu Pro Leu Val Thr Arg Gln Gly Asp Arg Ile Ala
1               5                   10                  15 att gtt agc ggt tta cgt acg cct ttt gcc cgt cag gcg acg gct ttt      96
Ile Val Ser Gly Leu Arg Thr Pro Phe Ala Arg Gln Ala Thr Ala Phe
                20                  25                  30 cat ggc att ccc gcg gtt gat tta ggg aag atg gtg gta ggc gaa ctg     144
His Gly Ile Pro Ala Val Asp Leu Gly Lys Met Val Val Gly Glu Leu
            35                  40                  45 ctg gca cgc agc gag atc ccc gcc gaa gtg att gaa caa ctg gtc ttt     192
Leu Ala Arg Ser Glu Ile Pro Ala Glu Val Ile Glu Gln Leu Val Phe
        50                  55                  60 ggt cag gtc gta caa atg cct gaa gcc ccc aac att gcg cgt gaa att     240
Gly Gln Val Val Gln Met Pro Glu Ala Pro Asn Ile Ala Arg Glu Ile
65                  70                  75                  80 gtt ctc ggt acg gga atg aat gta cat acc gat gct tac agc gtc agc     288
Val Leu Gly Thr Gly Met Asn Val His Thr Asp Ala Tyr Ser Val Ser
                85                  90                  95 cgc gct tgc gct acc agt ttc cag gca gtt gca aac gtc gca gaa agc     336
Arg Ala Cys Ala Thr Ser Phe Gln Ala Val Ala Asn Val Ala Glu Ser
                100                 105                 110 ctg atg gcg gga act att cga gcg ggg att gcc ggt ggg gca gat tcc     384
Leu Met Ala Gly Thr Ile Arg Ala Gly Ile Ala Gly Gly Ala Asp Ser
            115                 120                 125 tct tcg gta ttg cca att ggc gtc agt aaa aaa ctg gcg cgc gtg ctg     432
Ser Ser Val Leu Pro Ile Gly Val Ser Lys Lys Leu Ala Arg Val Leu
        130                 135                 140 gtt gat gtc aac aaa gct cgt acc atg agc cag cga ctg aaa ctc ttc     480
Val Asp Val Asn Lys Ala Arg Thr Met Ser Gln Arg Leu Lys Leu Phe
145                 150                 155                 160 tct cgc ctg cgt ttg cgc gac tta atg ccc gta cca cct gcg gta gca     528
Ser Arg Leu Arg Leu Arg Asp Leu Met Pro Val Pro Pro Ala Val Ala
                165                 170                 175 gaa tat tct acc ggc ttg cgg atg ggc gac acc gca gag caa atg gcg     576
Glu Tyr Ser Thr Gly Leu Arg Met Gly Asp Thr Ala Glu Gln Met Ala
                180                 185                 190
```

| | | |
|---|---|---|
| aaa acc tac ggc atc acc cga gaa cag caa gat gca tta gcg cac cgt<br>Lys Thr Tyr Gly Ile Thr Arg Glu Gln Gln Asp Ala Leu Ala His Arg<br>     195                    200                    205 | 624 |
| tcg cat cag cgt gcc gct cag gca tgg tca gac gga aaa ctc aaa gaa<br>Ser His Gln Arg Ala Ala Gln Ala Trp Ser Asp Gly Lys Leu Lys Glu<br>210                    215                    220 | 672 |
| gag gtg atg act gcc ttt atc cct cct tat aaa caa ccg ctt gtc gaa<br>Glu Val Met Thr Ala Phe Ile Pro Pro Tyr Lys Gln Pro Leu Val Glu<br>225                  230                  235                  240 | 720 |
| gac aac aat att cgc ggt aat tcc tcg ctt gcc gat tac gca aag ctg<br>Asp Asn Asn Ile Arg Gly Asn Ser Ser Leu Ala Asp Tyr Ala Lys Leu<br>                  245                    250                    255 | 768 |
| cgc ccg gcg ttt gat cgc aaa cac gga acg gta acg gca gca aac agt<br>Arg Pro Ala Phe Asp Arg Lys His Gly Thr Val Thr Ala Ala Asn Ser<br>         260                    265                    270 | 816 |
| acg ccg ctg acc gat ggc gcg gca gcg gtg atc ctg atg act gaa tcc<br>Thr Pro Leu Thr Asp Gly Ala Ala Ala Val Ile Leu Met Thr Glu Ser<br>             275                    280                    285 | 864 |
| cgg gcg aaa gaa tta ggg ctg gtg ccg ctg ggg tat ctg cgc agc tac<br>Arg Ala Lys Glu Leu Gly Leu Val Pro Leu Gly Tyr Leu Arg Ser Tyr<br>290                    295                    300 | 912 |
| gca ttt act gcg att gat gtc tgg cag gac atg ttg ctc ggt cca gcc<br>Ala Phe Thr Ala Ile Asp Val Trp Gln Asp Met Leu Leu Gly Pro Ala<br>305                  310                  315                  320 | 960 |
| tgg tca aca ccg ctg gcg ctg gag cgt gcc ggt ttg acg atg agc gat<br>Trp Ser Thr Pro Leu Ala Leu Glu Arg Ala Gly Leu Thr Met Ser Asp<br>                  325                    330                    335 | 1008 |
| ctg aca ttg atc gat atg cac gaa gcc ttt gca gct cag acg ctg gcg<br>Leu Thr Leu Ile Asp Met His Glu Ala Phe Ala Ala Gln Thr Leu Ala<br>             340                    345                    350 | 1056 |
| aat att cag ttg ctg ggt agt gaa cgt ttt gct cgt gaa gca ctg ggg<br>Asn Ile Gln Leu Leu Gly Ser Glu Arg Phe Ala Arg Glu Ala Leu Gly<br>355                  360                  365 | 1104 |
| cgt gca cat gcc act ggc gaa gtg gac gat agc aaa ttt aac gtg ctt<br>Arg Ala His Ala Thr Gly Glu Val Asp Asp Ser Lys Phe Asn Val Leu<br>370                    375                    380 | 1152 |
| ggc ggt tcg att gct tac ggg cat ccc ttc gcg gcg acc ggc gcg cgg<br>Gly Gly Ser Ile Ala Tyr Gly His Pro Phe Ala Ala Thr Gly Ala Arg<br>385                  390                  395                  400 | 1200 |
| atg att acc cag aca ttg cat gaa ctt cgc cgt cgc ggc ggt gga ttt<br>Met Ile Thr Gln Thr Leu His Glu Leu Arg Arg Arg Gly Gly Gly Phe<br>                  405                    410                    415 | 1248 |
| ggt tta gtt acc gcc tgt gct gcc ggt ggg ctt ggc gcg gca atg gtt<br>Gly Leu Val Thr Ala Cys Ala Ala Gly Gly Leu Gly Ala Ala Met Val<br>         420                    425                    430 | 1296 |
| ctg gag gcg gaa taa<br>Leu Glu Ala Glu<br>         435 | 1311 |

<210> SEQ ID NO 40
<211> LENGTH: 436
<212> TYPE: PRT
<213> ORGANISM: Escherichia coli

<400> SEQUENCE: 40

Met Gly Gln Val Leu Pro Leu Val Thr Arg Gln Gly Asp Arg Ile Ala
1                  5                        10                       15

Ile Val Ser Gly Leu Arg Thr Pro Phe Ala Arg Gln Ala Thr Ala Phe
                  20                       25                       30

His Gly Ile Pro Ala Val Asp Leu Gly Lys Met Val Val Gly Glu Leu
         35                    40                       45

Leu Ala Arg Ser Glu Ile Pro Ala Glu Val Ile Glu Gln Leu Val Phe
        50                  55                  60

Gly Gln Val Val Gln Met Pro Glu Ala Pro Asn Ile Ala Arg Glu Ile
 65                  70                  75                  80

Val Leu Gly Thr Gly Met Asn Val His Thr Asp Ala Tyr Ser Val Ser
                85                  90                  95

Arg Ala Cys Ala Thr Ser Phe Gln Ala Val Ala Asn Val Ala Glu Ser
            100                 105                 110

Leu Met Ala Gly Thr Ile Arg Ala Gly Ile Ala Gly Gly Ala Asp Ser
        115                 120                 125

Ser Ser Val Leu Pro Ile Gly Val Ser Lys Lys Leu Ala Arg Val Leu
    130                 135                 140

Val Asp Val Asn Lys Ala Arg Thr Met Ser Gln Arg Leu Lys Leu Phe
145                 150                 155                 160

Ser Arg Leu Arg Leu Arg Asp Leu Met Pro Val Pro Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Gln Gln Asp Ala Leu Ala His Arg
        195                 200                 205

Ser His Gln Arg Ala Ala Gln Ala Trp Ser Asp Gly Lys Leu Lys Glu
    210                 215                 220

Glu Val Met Thr Ala Phe Ile Pro Pro Tyr Lys Gln Pro Leu Val Glu
225                 230                 235                 240

Asp Asn Asn Ile Arg Gly Asn Ser Ser Leu Ala Asp Tyr Ala Lys Leu
                245                 250                 255

Arg Pro Ala Phe Asp Arg Lys His Gly Thr Val Thr Ala Ala Asn Ser
            260                 265                 270

Thr Pro Leu Thr Asp Gly Ala Ala Val Ile Leu Met Thr Glu Ser
        275                 280                 285

Arg Ala Lys Glu Leu Gly Leu Val Pro Leu Gly Tyr Leu Arg Ser Tyr
    290                 295                 300

Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Met Ser Asp
                325                 330                 335

Leu Thr Leu Ile Asp Met His Glu Ala Phe Ala Ala Gln Thr Leu Ala
            340                 345                 350

Asn Ile Gln Leu Leu Gly Ser Glu Arg Phe Ala Arg Glu Ala Leu Gly
        355                 360                 365

Arg Ala His Ala Thr Gly Glu Val Asp Asp Ser Lys Phe Asn Val Leu
    370                 375                 380

Gly Gly Ser Ile Ala Tyr Gly His Pro Phe Ala Ala Thr Gly Ala Arg
385                 390                 395                 400

Met Ile Thr Gln Thr Leu His Glu Leu Arg Arg Arg Gly Gly Phe
                405                 410                 415

Gly Leu Val Thr Ala Cys Ala Ala Gly Gly Leu Gly Ala Ala Met Val
            420                 425                 430

Leu Glu Ala Glu
        435

<210> SEQ ID NO 41
<211> LENGTH: 44
<212> TYPE: DNA

```
<213> ORGANISM: Artificial sequence
<220> FEATURE:
<223> OTHER INFORMATION: 5'-primer for fadIJ

<400> SEQUENCE: 41
gtgtgtgtga attctgtaaa aaaatggtta agactatgat cagg              44

<210> SEQ ID NO 42
<211> LENGTH: 44
<212> TYPE: DNA
<213> ORGANISM: Artificial sequence
<220> FEATURE:
<223> OTHER INFORMATION: 3'-primer for fadIJ

<400> SEQUENCE: 42
gtgtgtgtaa gctttgcctt atccattcac cgaatgaaac gctg              44
```